(12) United States Patent
Suzuki

(10) Patent No.: US 6,363,134 B1
(45) Date of Patent: Mar. 26, 2002

(54) X-RAY COMPUTED TOMOGRAPHY APPARATUS

(75) Inventor: Tatsuro Suzuki, Utsunomiya (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/480,949

(22) Filed: Jan. 11, 2000

(30) Foreign Application Priority Data

| Jan. 13, 1999 | (JP) | 11-006450 |
| Jan. 13, 1999 | (JP) | 11-006452 |
| Jan. 13, 1999 | (JP) | 11-006457 |

(51) Int. Cl.$^7$ ................................................. A61B 6/03
(52) U.S. Cl. ............................................. 378/15; 378/4
(58) Field of Search .......................... 378/4, 17, 20, 378/98, 901, 15

(56) References Cited

U.S. PATENT DOCUMENTS

| 5,218,623 A | * 6/1993 | Toki et al. ................... 378/15 |
| 5,224,135 A | * 6/1993 | Toki ............................ 378/15 |
| 5,262,946 A | * 11/1993 | Heuscher ..................... 378/15 |

FOREIGN PATENT DOCUMENTS

JP        11-267119        10/1999

* cited by examiner

Primary Examiner—Drew Dunn
(74) Attorney, Agent, or Firm—Oblon, Spivak, McClelland, Maier & Neustadt, P.C.

(57) ABSTRACT

Upon successively acquiring a plurality of tomographic images of an identical patient, and displaying them time-serially, the display mode of images is changed. More specifically, the display order of images is switched in correspondence with the standing position of the observer. The standing position of the observer can be automatically detected. The aperture width of a precollimator is controlled in accordance with the setups of images of interest/non-interest, and data from predetermined detection element arrays are bundled in accordance with the setups. At least one of a plurality of reconstructed tomographic images and a specific image undergo a differential process to generate and display a differential image. The pixel values of at least one of a plurality of reconstructed tomographic images are compared with a predetermined threshold value to generate and display an image consisting of only pixels that have exceeded the threshold value.

49 Claims, 49 Drawing Sheets

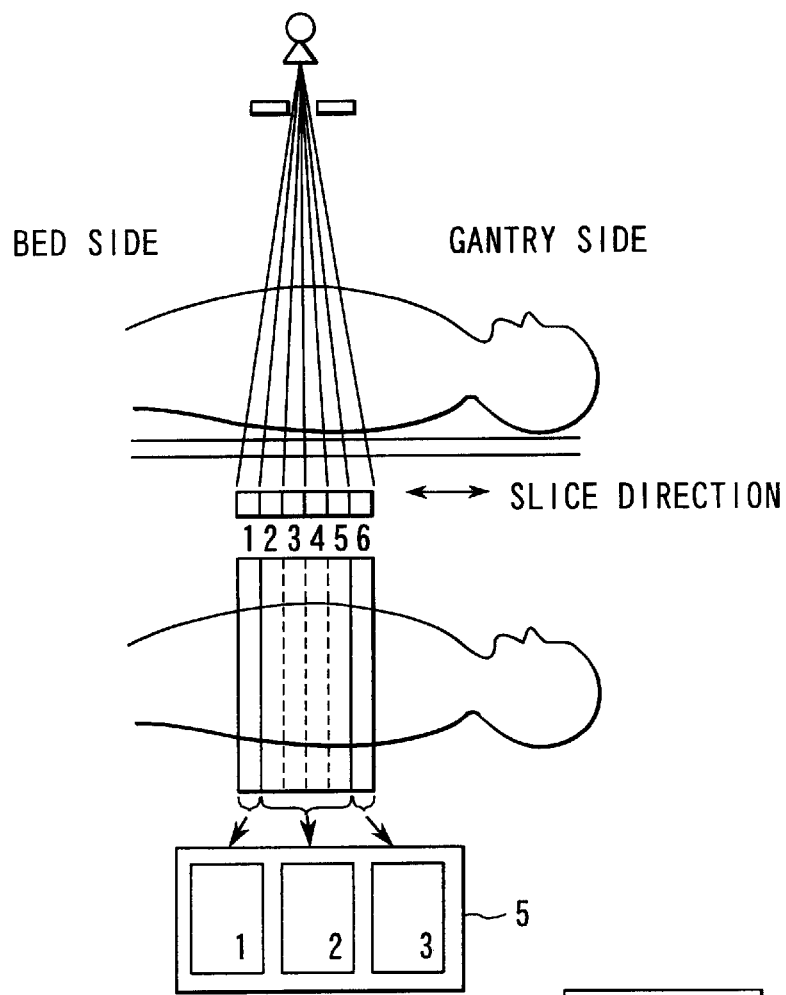
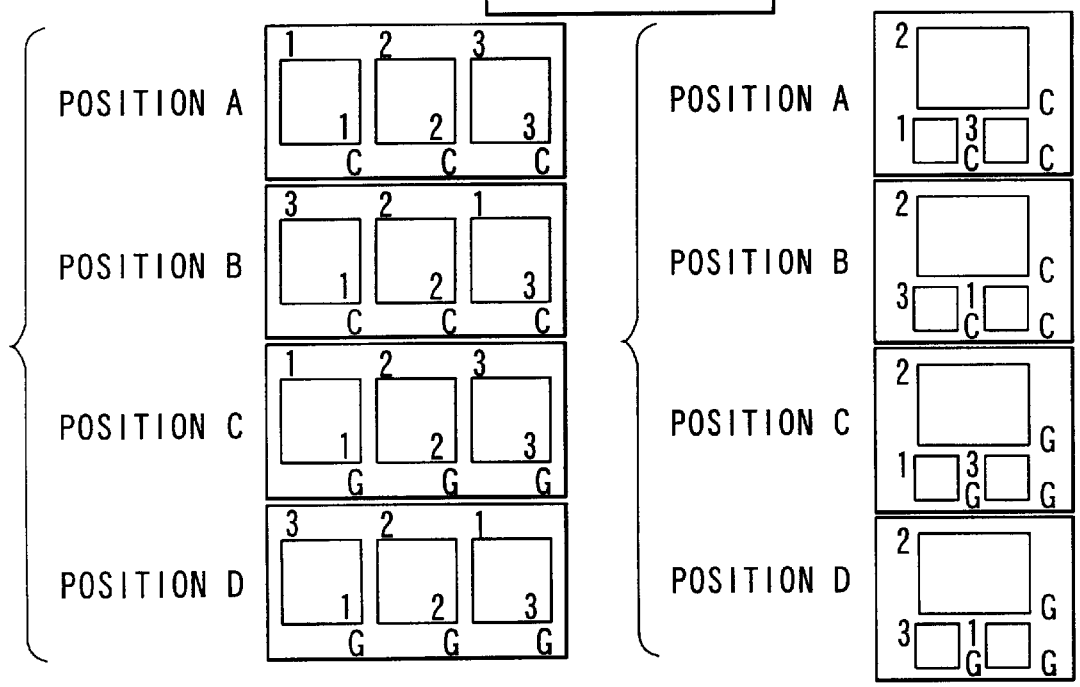
FIG. 9A
FIG. 9B
FIG. 9C
FIG. 9D

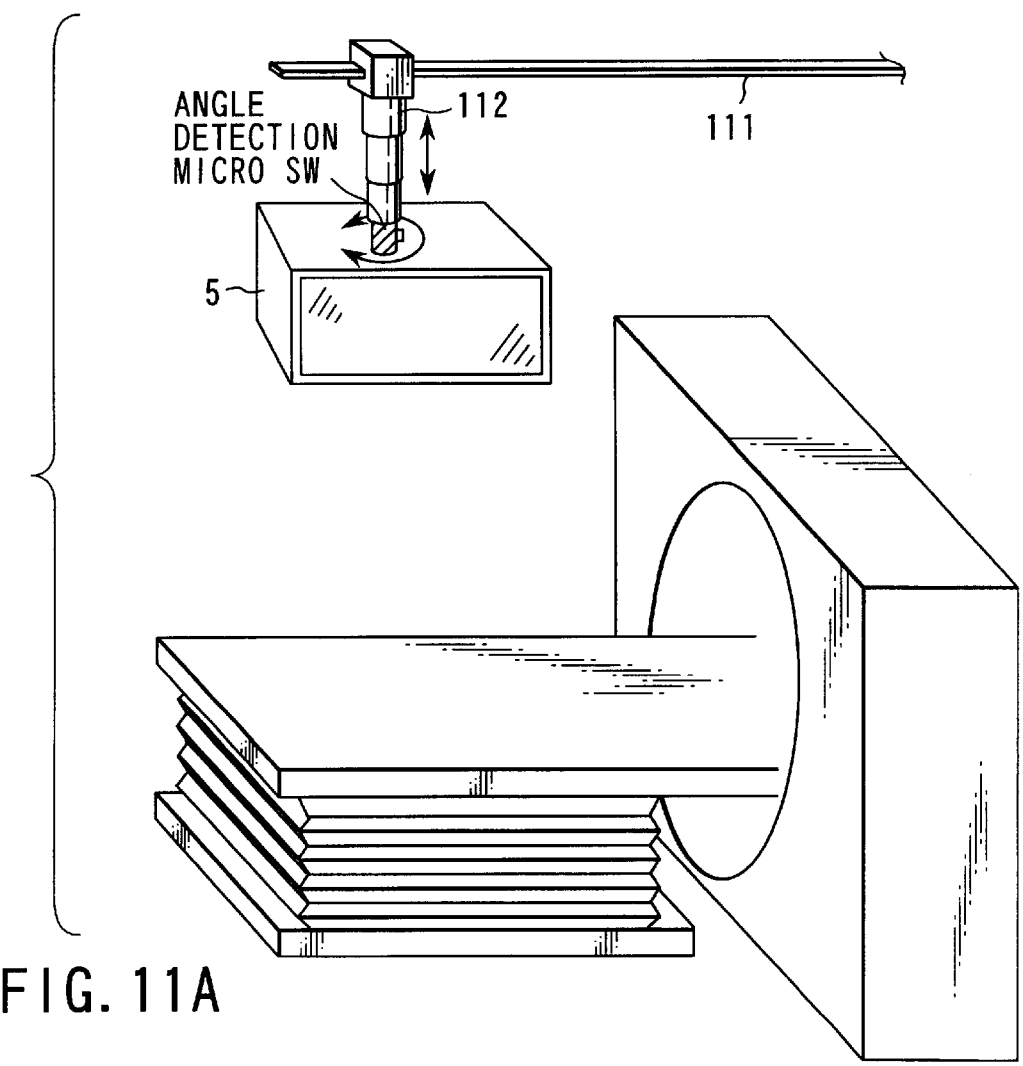
FIG. 11A
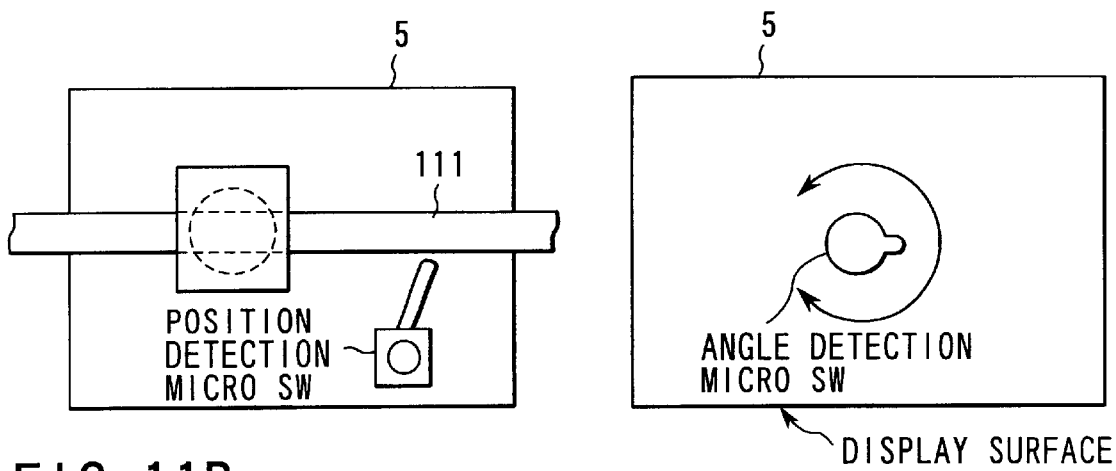
FIG. 11B
FIG. 11C

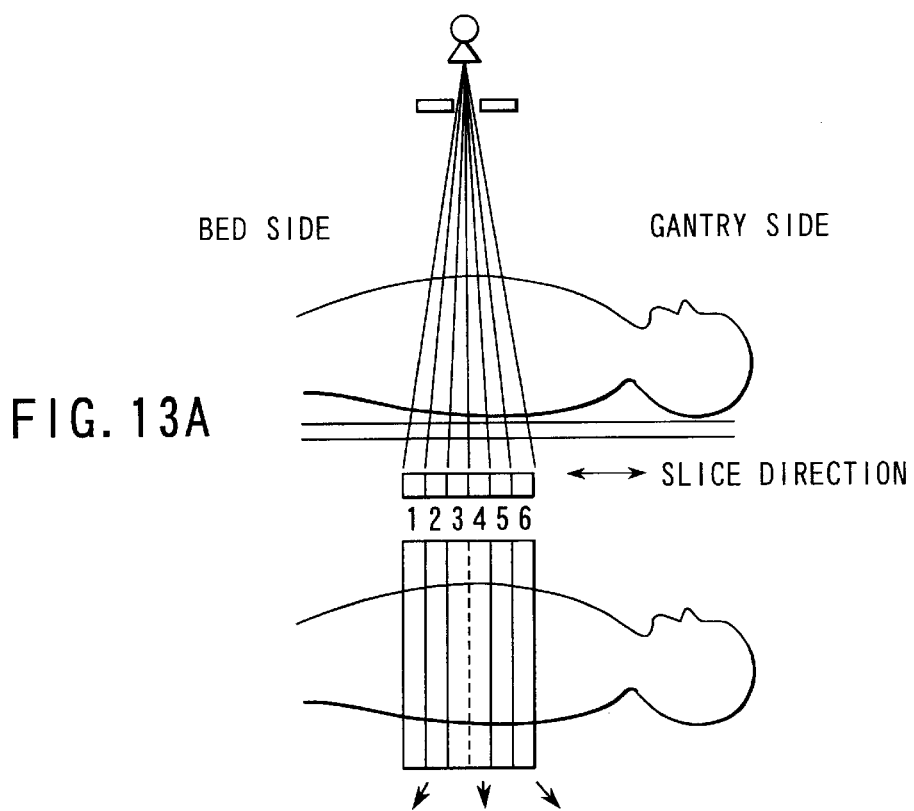
FIG. 13A
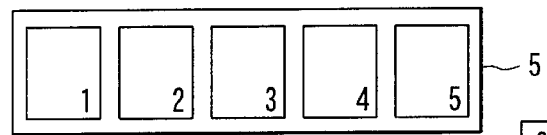
FIG. 13B
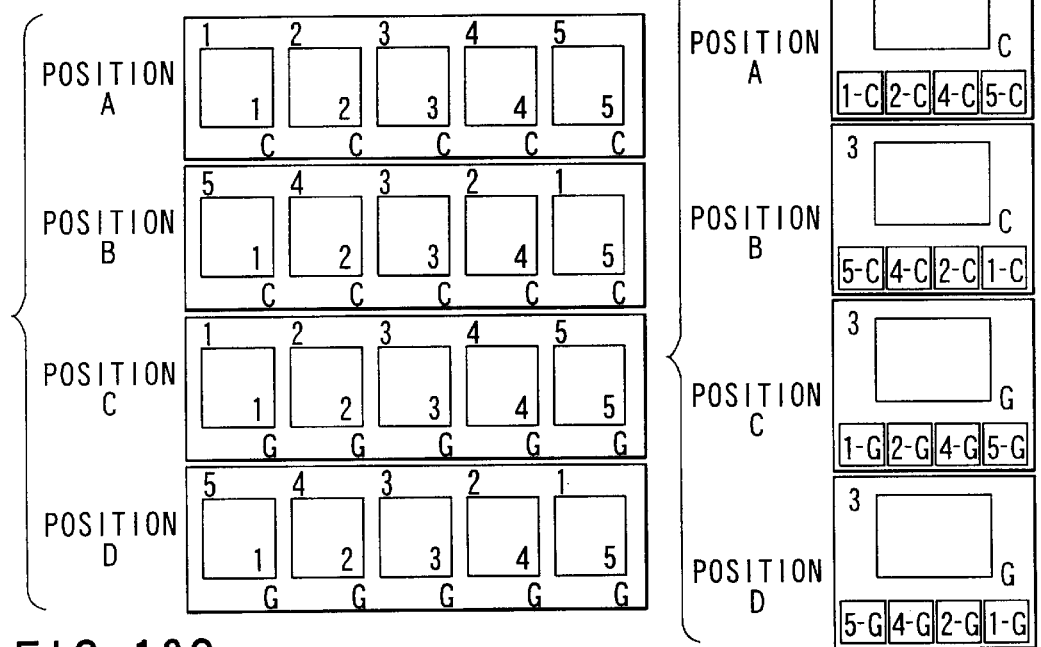
FIG. 13C
FIG. 13D

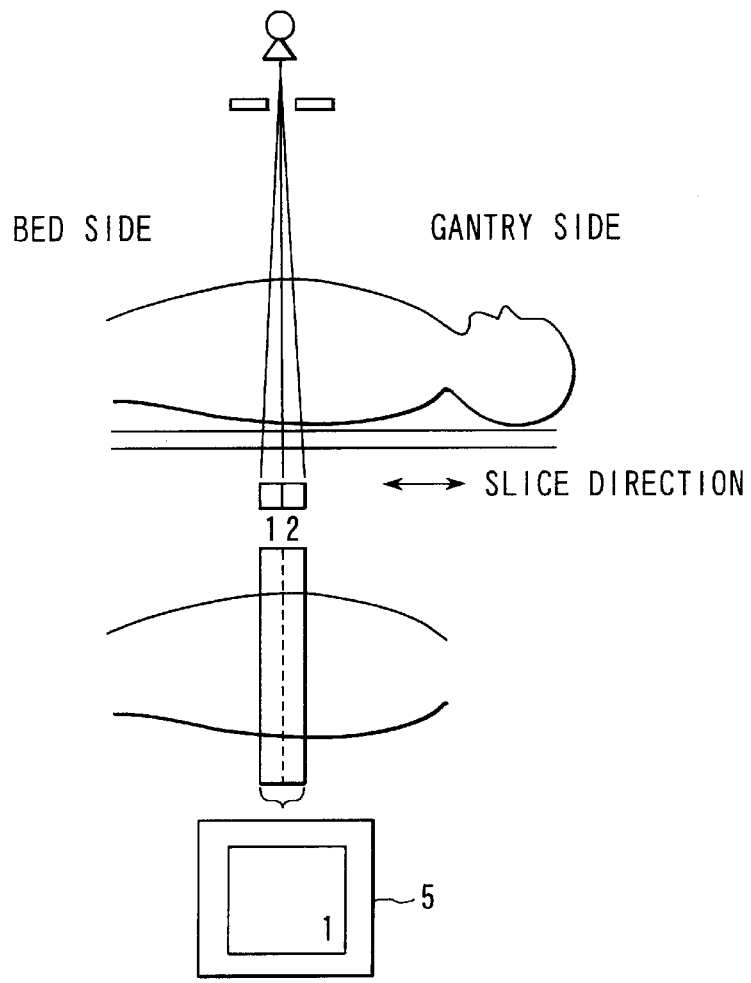
FIG. 15A
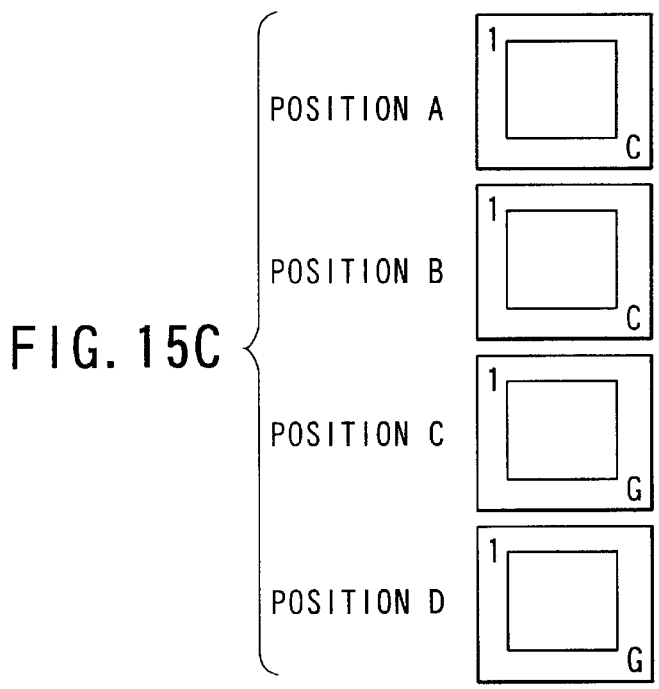
FIG. 15B
FIG. 15C

FIG. 16
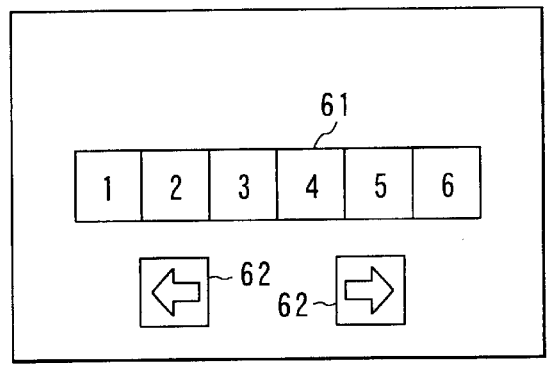
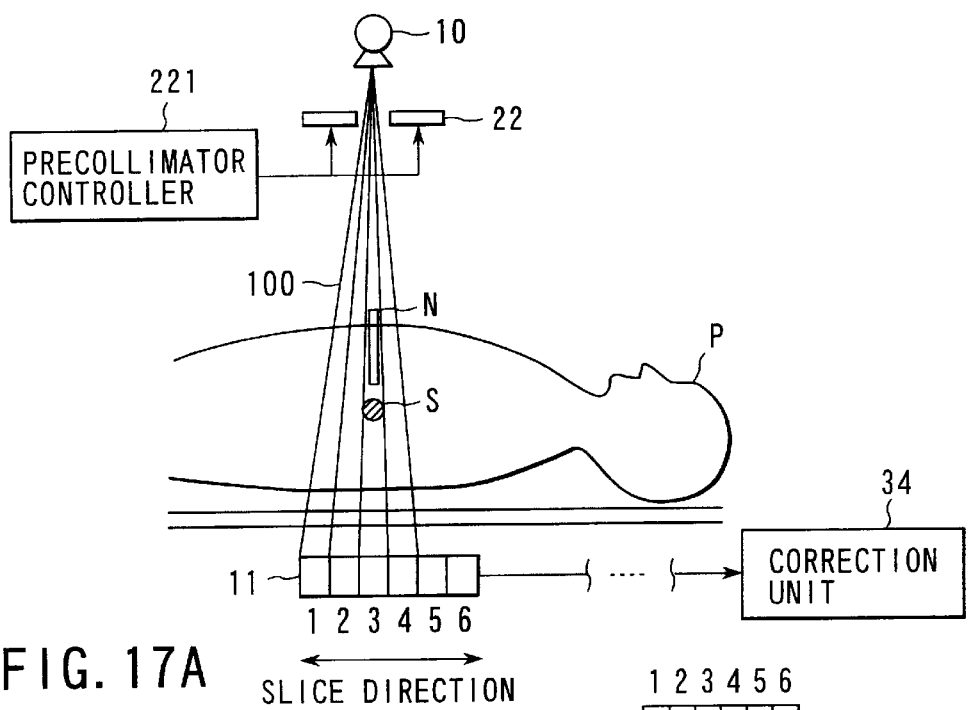
FIG. 17A
SLICE DIRECTION
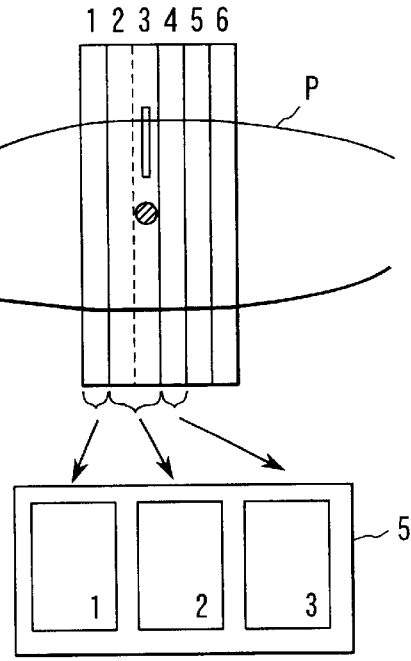
FIG. 17B

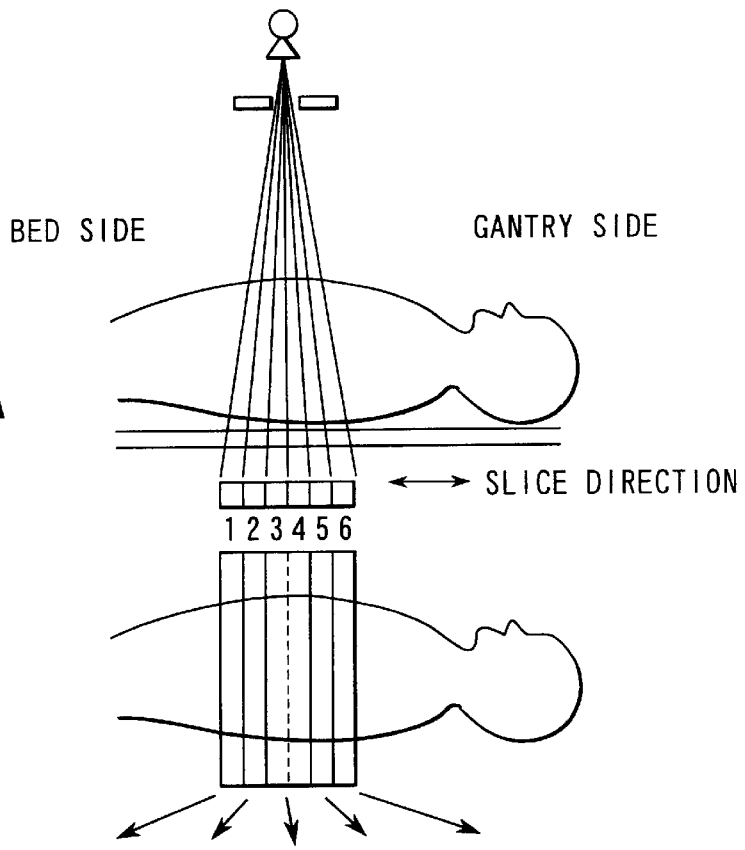
FIG. 47A
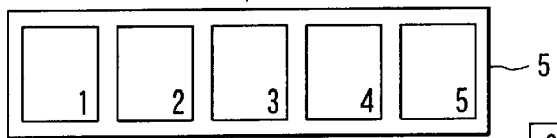
FIG. 47B
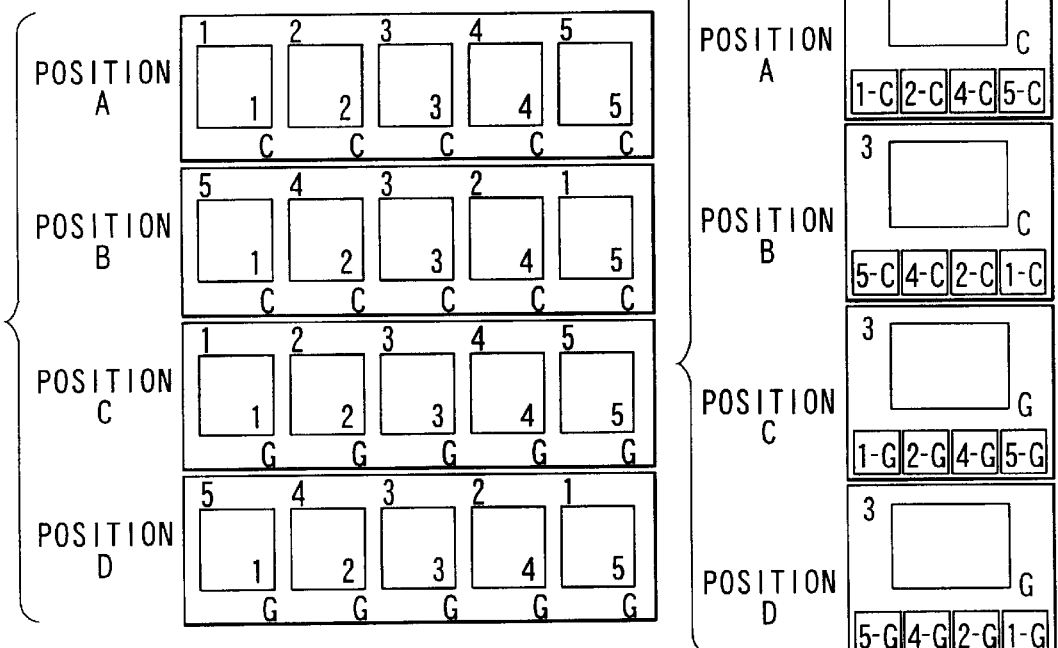
FIG. 47C
FIG. 47D

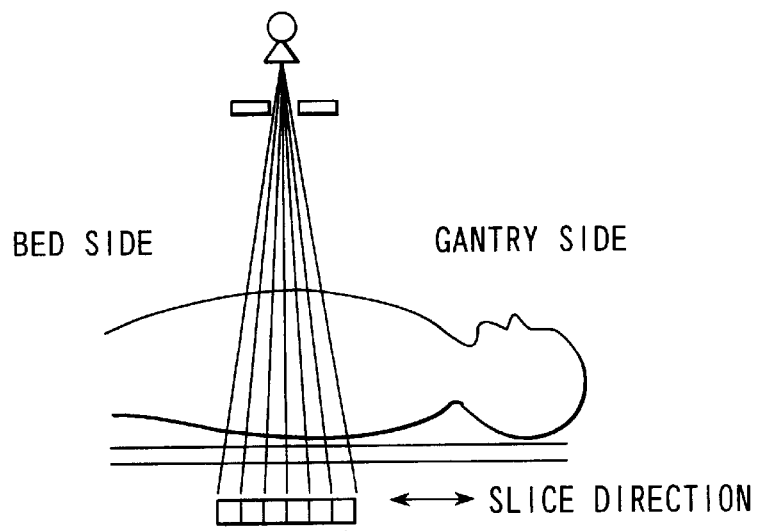
FIG. 48A
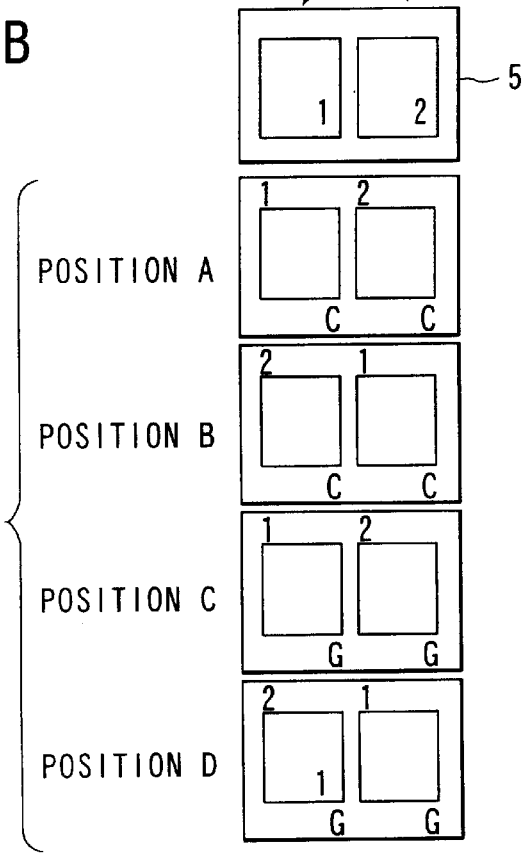
FIG. 48B
FIG. 48C

X-RAY COMPUTED TOMOGRAPHY APPARATUS

BACKGROUND OF THE INVENTION

The present invention relates to an x-ray computed tomography apparatus for successively acquiring images of a plurality of slices of a given patient body and time-serially displaying the acquired images. The present invention also relates to an x-ray computed tomography apparatus which has a detector consisting of a plurality of arrays, reconstructs a plurality of images on the basis of detector data within a shorter period of time than the time required per scan, and displays the reconstructed images in real time.

Multi-slice CT is known as CT that can simultaneously reconstruct a plurality of tomographic images (the number of which does not always correspond to the number of detector arrays) within a shorter period of time than the time required per scan, and can display them approximately in real time (CT fluoroscopy).

In so-called conventional single-slice CT, only one tomographic image can undergo fluoroscopy. However, in multi-slice CT, a plurality of images (plurality of slices) can undergo CT fluoroscopy at the same time. In CT scan, tomographic images are displayed approximately in real time.

Since multi-slice CT fluoroscopy allows to observe a plurality of tomographic images at the same time, it is effective for various diagnoses, such as deviation detection of a biopsy needle in, e.g., biopsies and the like.

For example, in conventional multi-slice CT having a multi-slice detector consisting of three detector arrays, X-rays (radiation) radiated by an X-ray tube are collimated by a precollimator to a thickness corresponding to three slices. The collimated X-rays are transmitted through a patient body and then enter the multi-slice detector. Images corresponding to the individual detector arrays are independently displayed on a display.

During centesis procedures or the like, the operator of a centesis needle stands near a gantry, and works with the needle while observing a display equipped near the gantry.

The conventional X-ray computed tomography apparatus that allows multi-slice CT fluoroscopy suffers the following problems.

(1) Problem of Image Display Order

A case will be examined below wherein images reconstructed in correspondence with detector arrays 1, 2, and 3 are displayed in the order of images 1, 2, and 3 from the left, as shown in FIG. 50. As shown in FIG. 51, when the observer stands at position A, since the actual order of tomographic images in the slice direction when viewed from the observer matches the display order on the display, the observer can manipulate the centesis needle without any problems.

However, when the observer is located at position B shown in FIG. 52, the actual order of tomographic images when viewed from the observer is opposite to the display order on the display. As a result, the observer must imaginarily re-arrange the images, and has hard time manipulating the centesis needle.

Not only in the centesis procedures but also upon normally observing fluoroscopic images, the observer often mistakes the order of images with respect to the patient position. In this example, the display is disposed near a patient. However, the same problem is posed for, e.g., a display placed on a console.

Also, the same problem is posed when the observer stands on the gantry side, as indicated by positions C and D shown in FIG. 52.

(2) Obverse/reverse Problem of Image

Furthermore, positions A and C of the observer in FIG. 52 are compared. The observer at position A observes a section of the patient as if he or she were seeing the patient from the bed side (a direction in which the top of the head of the patient is seen from his or her toe side). At this time, an image seen from the foot side (bed side) must be displayed.

On the other hand, the observer at position C observes a section of the patient as if he or she were seeing the patient from the head side. At this time, an image seen from the head side (gantry side) must be displayed. The same applies to positions B and D of the observer.

For example, in the centesis procedures, the observer must manipulate the centesis needle while considering whether the image displayed on the display is seen from the bed side or the head (gantry) side. The observer may mistake the centesis direction, resulting in inefficient and long centesis. Not only in the centesis procedures but also upon observing fluoroscopic images, a wrong diagnosis is likely to be made.

In multi-slice CT fluoroscopy, when reconstructed images are merely displayed in a line, since the observer is forced to simultaneously observe a large number of images, it becomes hard for him or her to quickly and adequately grasp the current circumstance. Especially, this problem becomes more conspicuous with increasing number of fluoroscopic images.

For example, in the centesis procedures, three images are displayed in a line, a centesis needle is inserted along the central image, and the images at the two ends are normally used in deviation detection of the centesis needle.

However, it is a considerable burden even on a skilled person to simultaneously observe three images in detail, and he or she cannot recognize deviation of the insertion route of the centesis needle in time. To prevent this, if the centesis is slowly done over a long period of time, not only the centesis time becomes longer but also the dose on the patient increases.

Therefore, a new mechanism that allows an appropriate and quick surgical procedure such as a centesis or the like using multi-slice CT fluoroscopy is conventionally demanded.

Also the following problem is posed.

In multi-slice CT fluoroscopy, when reconstructed images are merely displayed in a line, the individual images are inevitably displayed in a reduced scale, and the observer can hardly observe them in detail. For example, when three images are displayed in a line at the same time, the image size is reduced to ⅓ compared to a case wherein only one image is displayed.

Upon making a surgical procedure such as a centesis or the like, circumstantial observation is especially required near a target portion. If the operator mistakes the distal end position of the centesis needle, tissue which is not the target portion may be sampled in, e.g., biopsies.

Furthermore, in conventional multi-slice CT having a multi-slice detector consisting of three detection element arrays, as shown in FIG. 53, the dose on the patient becomes larger than single-slice CT fluoroscopy since the beam width is increased in the slice direction.

BRIEF SUMMARY OF THE INVENTION

The present invention has been made in consideration of the above situation, and has as its object to provide an X-ray computed tomography apparatus for displaying images of a plurality of slices by appropriately setting the display order or the obverse/reverse side of images in accordance with the observation position or the like of the observer.

It is another object of the present invention to provide an X-ray computer tomography apparatus which allows an appropriate and quick surgical procedure such as a centesis or the like using multi-slice CT fluoroscopy.

It is still another object of the present invention to provide an X-ray computer tomography apparatus which can reduce the dose on a patient in multi-slice CT fluoroscopy.

According to the present invention, there is provided the following X-ray computed tomography apparatuses.

A first X-ray computed tomography apparatus according to the present invention comprises: a detection unit for detecting a transmitted X-ray beam which is emitted by an X-ray generation unit and transmitted through an object to be examined; a reconstruction unit for reconstructing a plurality of images associated with different slices of the object to be examined on the basis of detection data obtained by the detection unit; a display unit for displaying images reconstructed by the reconstruction unit in a line; and a display control unit for controlling the display unit to change a display mode of the images.

A second X-ray computed tomography apparatus according to the present invention comprises: a detection unit for detecting a transmitted X-ray beam which is emitted by an X-ray generation unit and transmitted through an object to be examined; a reconstruction unit for reconstructing a tomographic image of the object to be examined on the basis of detection data obtained by the detection unit; a display unit for displaying a plurality of tomographic images reconstructed by the reconstruction unit in a line; and changing means for changing the way the plurality of tomographic images line up in the display unit in accordance with a standing position of an observer with respect to the object to be examined.

A third X-ray computed tomography apparatus according to the present invention comprises: a detection unit which is constructed by a plurality of detection element arrays each having a plurality of detection channels in a slice direction, and in which the respective detection channels detect X-rays; a reconstruction unit for reconstructing tomographic images of an object to be examined in units of a predetermined number of detection element arrays on the basis of detection data detected by the detection unit; a display unit for displaying the tomographic images in units of a predetermined number of detection element arrays in a line; and a display control unit for controlling the display unit to display a first tomographic image of the plurality of tomographic images in a display mode different from a second tomographic image.

A fourth X-ray computed tomography apparatus according to the present invention comprises: an X-ray generation unit; a detection unit which is constructed by a plurality of detection element arrays each having a plurality of detection channels in a slice direction, and in which the respective detection channels detect X-rays emitted by the X-ray generation unit; a reconstruction unit for reconstructing tomographic images of an object to be examined in units of a predetermined number of detection element arrays on the basis of detection data detected by the detection unit; slice thickness changing means for setting a slice thickness of an image of interest of the tomographic images reconstructed by the reconstruction unit to be larger than a slice thickness of an image of non-interest; and a display unit for displaying in a line the tomographic images, the slice thicknesses of which have been changed by the slice thickness control means.

A fifth X-ray computed tomography apparatus according to the present invention comprises: a detection unit for detecting a transmitted X-ray beam which is emitted by an X-ray generation unit and transmitted through an object to be examined; a reconstruction unit for reconstructing a tomographic image of the object to be examined on the basis of detection data obtained by the detection unit; a display unit for displaying a plurality of tomographic images reconstructed by the reconstruction unit in a line; and a display control unit for displaying a first tomographic image having a first slice thickness at a substantially center of the display unit, and displaying a second tomographic image having a second slice thickness smaller than the first slice thickness at an end portion of the first tomographic image.

A sixth X-ray computed tomography apparatus according to the present invention comprises: an X-ray generation unit for generating X-rays; a detection unit which is constructed by a plurality of detection element arrays each having a plurality of detection channels in a slice direction, and in which the respective detection channels detect X-rays emitted by the X-ray generation unit; generation means for generating a tomographic image of an object to be examined by bundling data from the detection element arrays; and changing means for changing at least one of an incident width of an X-ray beam that hits the detection element arrays and the bundle of data during a scan period.

A seventh X-ray computed tomography apparatus according to the present invention comprises: an X-ray generation unit for generating X-rays; a detection unit which is constructed by a plurality of detection element arrays each having a plurality of detection channels in a slice direction, and in which the respective detection channels detect X-rays emitted by the X-ray generation unit; a reconstruction unit for reconstructing a tomographic image of an object to be examined on the basis of detection data detected by the detection unit; and an image processing unit for generating a differential image by differentially processing a specific image and at least one of a plurality of tomographic images reconstructed by the reconstruction unit.

An eighth X-ray computed tomography apparatus according to the present invention comprises: an X-ray generation unit for generating X-rays; a detection unit which is constructed by a plurality of detection element arrays each having a plurality of detection channels in a slice direction, and in which the respective detection channels detect X-rays emitted by the X-ray generation unit; a reconstruction unit for reconstructing a tomographic image of an object to be examined on the basis of detection data detected by the detection unit; and a threshold process unit for comparing a pixel value of at east one of a plurality of tomographic images reconstructed by the reconstruction unit with a predetermined threshold value, and generating a threshold image consisting of pixel values that have exceeded the threshold value.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9A is a view showing multi-slice CT fluoroscopy according to the first embodiment of the present invention, particularly the X-ray radiation state on a patient;

FIG. 9B is a view showing multi-slice CT fluoroscopy according to the first embodiment of the present invention, particularly a plurality of slices of a patient and their displayed images;

FIG. 9C is a view showing multi-slice CT fluoroscopy according to the first embodiment of the present invention, particularly an example of display according to the standing position of the observer;

FIG. 9D is a view showing multi-slice CT fluoroscopy according to the first embodiment of the present invention, particularly another example of display according to the standing position of the observer;

FIG. 11A is a perspective view showing a mechanism for detecting the standing position of the observer according to the second embodiment of the present invention;

FIG. 11B is a view showing a position detection micro switch of the mechanism for detecting the standing position of the observer according to the second embodiment of the present invention;

FIG. 11C is a view showing an angle detection micro switch of the mechanism for detecting the standing position of the observer according to the second embodiment of the present invention;

FIG. 13A is a view showing a case in which a 5-image fluoroscopy mode is set, and the X-ray radiation state onto a patient according to a modification of the present invention;

FIG. 13B is a view showing the case in which the 5-image fluoroscopy mode is set, and a plurality of slices of the patent and their displayed images according to the modification of the present invention;

FIG. 13C is a view showing the case in which the 5-image fluoroscopy mode is set, and an example of display according to the standing position of the observer according to the modification of the present invention;

FIG. 13D is a view showing the case in which the 5-image fluoroscopy mode is set, and another example of display according to the standing position of the observer according to the modification of the present invention;

FIG. 15A is a view showing a case wherein the present invention is applied to single-slice CT, and the X-ray radiation state onto a patient;

FIG. 15B is a view showing a case wherein the present invention is applied to single-slice CT, and a slice of the patient and its displayed image;

FIG. 15C is a view showing a case wherein the present invention is applied to single-slice CT, and an example of display according to the standing position of the observer;

FIG. 16 is a view showing the arrangement of a designation means for designating an image of interest;

FIG. 17A is a side view of a state wherein X-rays radiated from an X-ray tube toward the patient enter a multi-slice detector;

FIG. 17B is a view showing the way the image of interest and image of non-interest are displayed;

FIG. 47A is a view showing another example of image bundling, and the X-ray radiation state onto a patient;

FIG. 47B is a view showing another example of image bundling, and a plurality of slices of the patient and their displayed images;

FIG. 47C is a view showing another example of image bundling, and an example of image display according to the standing position of the observer;

FIG. 47D is a view showing another example of image bundling, and another example of image display according to the standing position of the observer;

FIG. 48A is a view showing still another example of image bundling, and the X-ray radiation state onto a patient;

FIG. 48B is a view showing still another example of image bundling, and a plurality of slices of the patient and their displayed images;

FIG. 48C is a view showing still another example of image bundling, and an example of image display according to the standing position of the observer;

DETAILED DESCRIPTION OF THE INVENTION

The preferred embodiments of the present invention will be described hereinafter with reference to the accompanying drawings.

Figure 1:
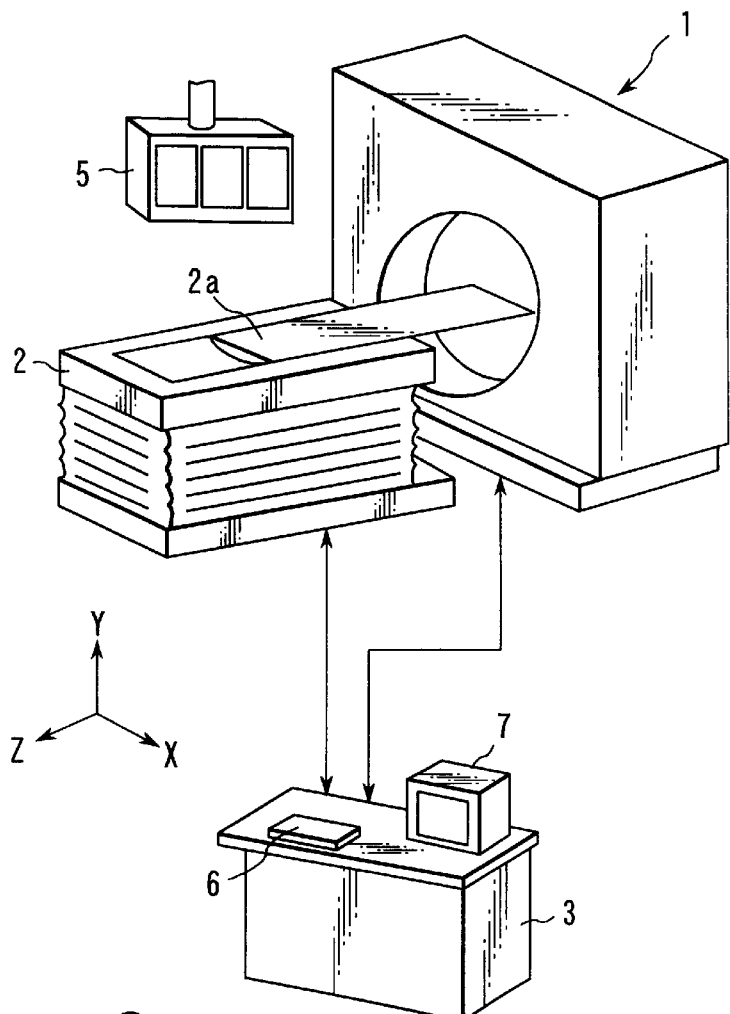
FIG. 1 is a perspective view showing the outer appearance of a multi-slice CT system according to an embodiment of the present invention.
Figure 2:
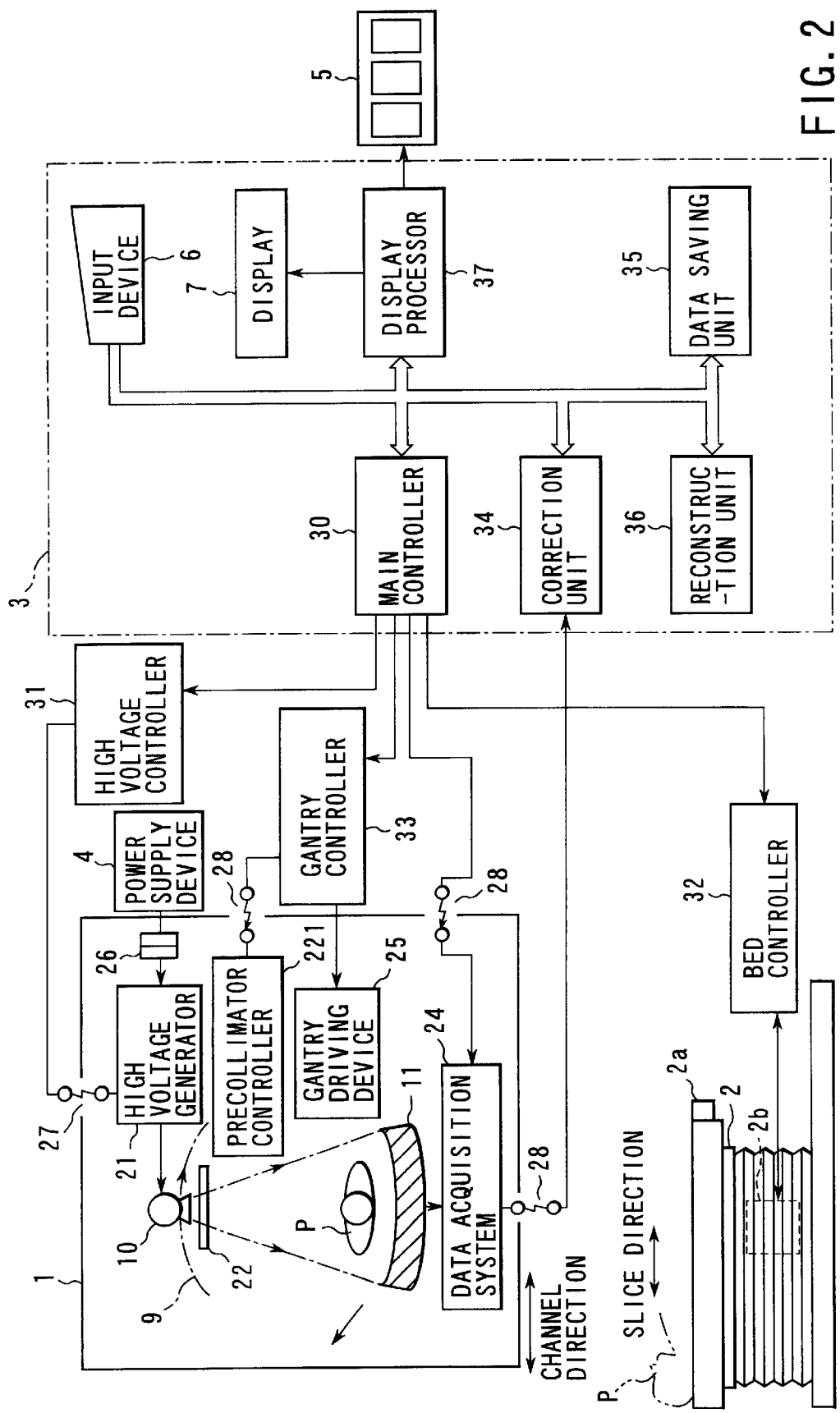
FIG. 2 is a block diagram showing a schematic arrangement of a multi-slice CT system according to the embodiment of the present invention.

FIG. 1 is a perspective view showing the outer appearance of a multi-slice CT fluoroscopy system according to an embodiment of an X-ray computer tomography apparatus of the present invention, and FIG. 2 is a block diagram showing a schematic arrangement of this system.

As shown in FIGS. 1 and 2, the multi-slice CT fluoroscopy system comprises a gantry 1, bed 2, control cabinet 3, input device 6, power supply 4, displays 5 and 7, and various controllers 31 to 33, and is driven by, e.g., an R-R system. As the controllers, a high-voltage controller 31, gantry controller 33, and bed controller 32 are equipped.

As shown in FIG. 1, the longitudinal direction of the bed 2 is defined to be a slice direction (or a rotation axis direction) Z, and two directions perpendicular to that direction are defined to be a channel direction X and X-ray beam radiation direction Y, respectively.

A top plate 2a is supported on the upper surface of the bed 2 to be slidable in its longitudinal direction (slice direction Z), and a patient P lies down on the upper surface of the top plate 2a. The top plate 2a is inserted into a diagnostic opening of the gantry 1 to be free to move back and forth upon being driven by a bed driving device 2b represented by a servo motor. The bed driving device 2b receives a driving signal from the controller 32. The bed 2 comprises a position detector (not shown) such as an encoder or the like for detecting the position of the top plate 2a in the longitudinal direction of the bed as an electrical signal, and sends the detection signal to the controller 32 as a bed control signal.

The gantry 1 has an approximately cylindrical rotary frame therein. The aforementioned diagnostic opening is located inside the rotary frame. On the rotary frame, an X-ray tube 10 and multi-slice detector 11 are provided to face each other with the patient inserted into the diagnostic opening therebetween, as shown in FIG. 2. A high-voltage generator 21, precollimator 22, precollimator controller 221, data acquisition system (DAS) 24, and gantry driving device 25 are equipped at predetermined positions on the rotary frame.

The precollimator 22 has a variable aperture in the slice direction, and defines the beam width of X-rays emitted by the X-ray tube 10 in the slice direction, and this variable aperture width is controlled by the precollimator controller 221.

The X-ray tube 10 serving as an X-ray source has, e.g., the structure of a rotary anode X-ray tube, in which a filament is heated by supplying a current from the high-voltage generator 21 to the filament, and hot electrons are emitted toward a target. The hot electrons impinge against the target surface to form an effective focal point, and an X-ray beam (fan beam) is radiated from the portion of the effective focal point of the target surface.

The high-voltage generator 21 receives a low-voltage power supply from the power supply device 4 via a low-voltage slip ring 26, and also receives an X-ray radiation control signal from the high-voltage controller 31 via an optical signal transmission system 27. Thus, the high-voltage generator 21 generates a high voltage from the received low-voltage power supply, generates a pulse-shaped tube voltage from the high voltage in accordance with the control signal, and supplies it to the X-ray tube 10.

Figure 3:
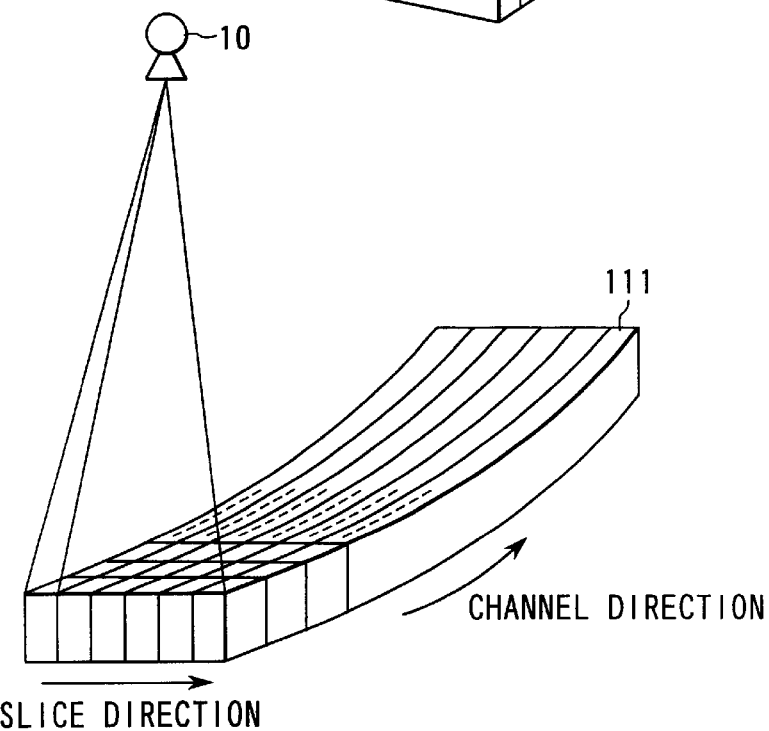
FIG. 3 is a perspective view showing the arrangement of a multi-slice detector according to the embodiment of the present invention.

The multi-slice detector 11 comprises a two-dimensional detector obtained by arranging in the slice direction a plurality of (six) detector arrays 111 each having a plurality of detection channels, as shown in FIG. 3.

The X-ray tube 10 and X-ray detector 11 are rotatable about the rotation central axis of the diagnostic opening in the axial direction in the gantry 1 upon rotation of the rotary frame. Each detection element of the multi-slice detector 11 has a solid-state detector structure including a scintillator and photodiode for converting incoming transmitted X-rays into a corresponding current signal. A weak current signal detected by this detector 11 is sent to the DAS 24.

The DAS 24 amplifies and A/D converts the weak current signal as the detection signal of transmitted X-rays sent from the detector 11, and sends that data as acquired data to a data transmission unit 28. To attain this, the DAS 24 comprises a data selection unit for selecting detection signals for one array in units of channels from "n channels×f element arrays" detection signals (n and f are positive integers larger than "1") in accordance with an array select signal, and bundling them, and a data acquisition unit which amplifies and A/D converts the detection signals selected by the data selection unit (neither units are shown as the detector 11 is a two-dimensional detector). The array select signal is supplied from, e.g., a main controller (to be described later).

The data transmission unit 28 connects rotary- and stationary-side signal paths in the gantry 1, and uses, for example, an optical transmission system that transmits signals in a non-contact manner.

A correction unit 34 performs various correction processes of acquired digital data sent from the DAS 24 in accordance with a process command from a main controller 30. The acquired data that has undergone the correction processes is temporarily stored and saved in a data saving unit 35 in response to a write command from the main controller 30. The saved data is read out from the data saving unit 35 in accordance with a read command from the main controller 30 at a desired timing, and is transferred to a reconstruction unit 36. Under the control of the main controller 30, the reconstruction unit 36 executes a reconstruction process in units of slices on the basis of, e.g., a convolution back-projection method when it receives acquired data to be reconstructed, thus generating tomographic images.

Under the control of the main controller 30, tomographic image data is saved in the data saving unit 35 as needed and is also sent to a display processor 37. The display processor 37 performs required processes such as a color conversion process, a superposing process of annotation data and scan information, and the like for the tomographic image data, and supplies the processed data to the display 5. The display 5 D/A-converts the image data and displays it as a tomographic image. The input device 6 is a means at which the operator makes various kinds of designation of scan conditions (including the number and locations of detector arrays of the detector, scan portion and position, slice thickness, X-ray tube voltage and current, scan direction with respect to the patient, and the like), image display conditions, and the like.

The system of this embodiment can implement multi-slice CT fluoroscopy, i.e., the aforementioned reconstruction unit 36 reconstructs at least one or a plurality of (which do not always correspond to the number of detector arrays) images (tomographic images) including an image of interest and image of non-interest within a time shorter than the time required per scan. The reconstructed images are displayed on the display 5 nearly in real time.

When a biopsy such as a so-called centesis is made, the operator (doctor) of a centesis needle stands near the gantry 1 and works with it while observing images displayed on the display 5.

(First Embodiment)

The first embodiment relates to a multi-slice CT fluoroscopy system which can manually switch the display order of images in accordance with the standing position of the observer.

In the system of this embodiment, the number of images to be displayed corresponding to slice positions, and the slice thickness of each image can be arbitrarily set. More specifically, for example, data from four central (second to fifth) detector arrays are bundled to obtain a single image, the second image is obtained from data of the first detector array, and the third image is obtained from data of the sixth detector array, thus executing a fluoroscopy mode by a total of three images.

[First Input Device]

Figure 4:
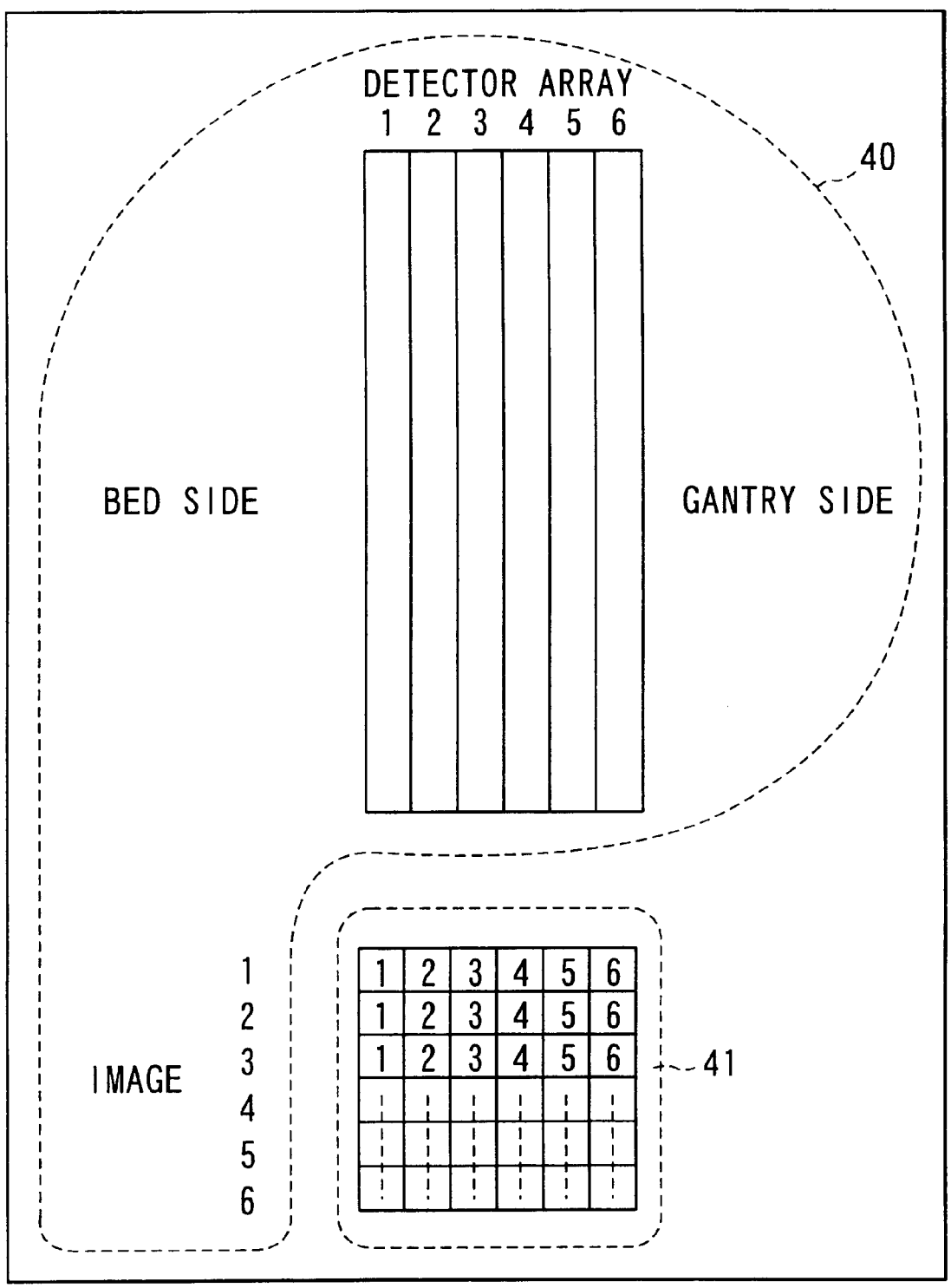
FIG. 4 is a view showing a first input device according to the first embodiment of the present invention.

FIG. 4 is a view showing the first input device. The first input device is a means for designating detector arrays used, and image bundling, and is arranged in the input device 6. Note that the input device 6 is provided to the gantry 1 or bed 2, or on the control cabinet 3, as shown in FIG. 1.

Referring to FIG. 4, reference numeral 40 denotes icons (iconic symbols) that indicate the numbers of detector arrays, gantry side and bed side, and image numbers; and 41, a plurality of buttons which include LEDs and make the detector array numbers correspond to the image numbers.

When the operator presses one of the buttons 41, an LED inside that button is turned on, and with this operation, a required detector array can be assigned to each image.

When a plurality of detector arrays are selected for a single image, data acquired from these detector arrays are bundled to form a single image (image bundling).

Figure 5:
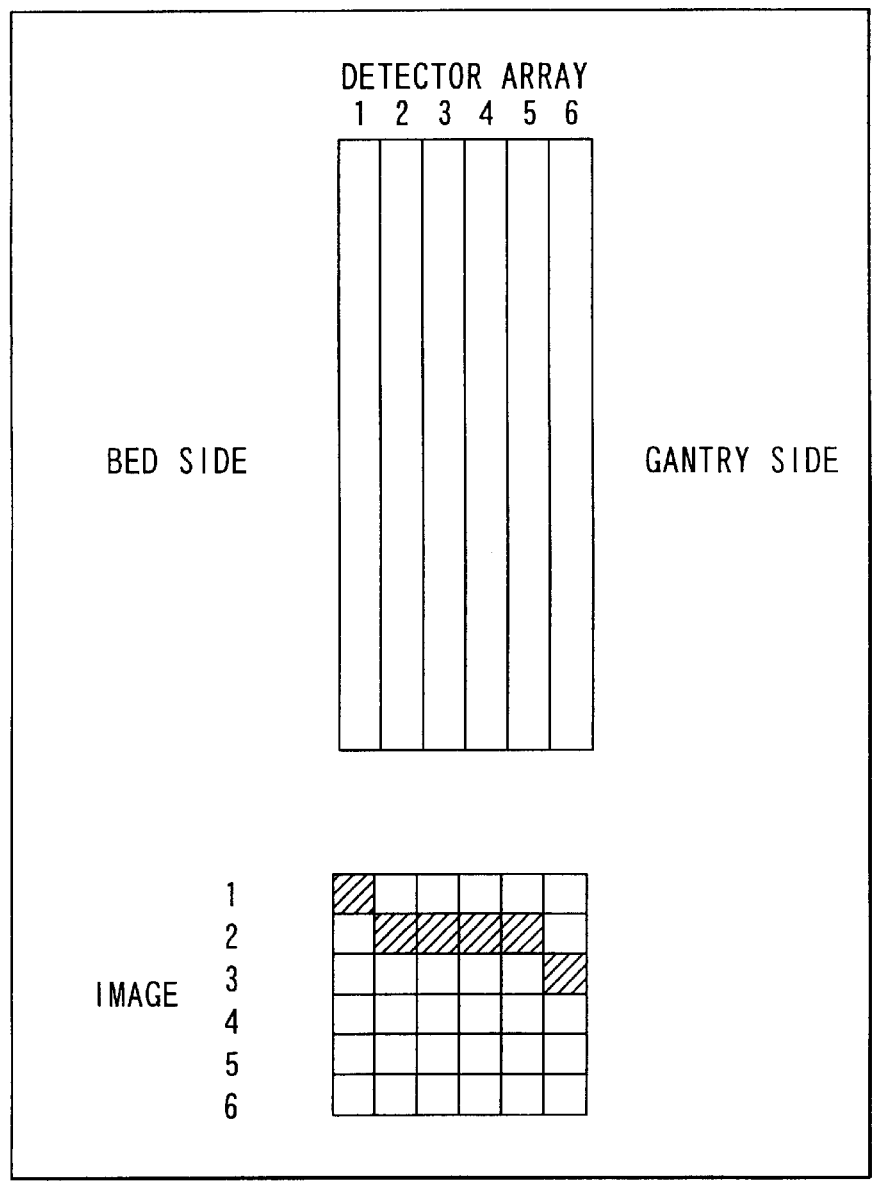
FIG. 5 is a view showing an example of designation by the first input device according to the first embodiment of the present invention.

FIG. 5 shows an example of designation by this first input device.

ON buttons (indicated by hatching) mean that those buttons have been pressed by the operator. Note that the aforementioned conditions are designated by the buttons but such designation may be implemented by a display and touch panel, or a mouse cursor which is moved to a predetermined location on the display screen and is clicked may be used in place of the touch panel.

A signal that represents depression information of the buttons on the first input device is sent to the main controller 30.

[Second Input Device]

Figure 6:
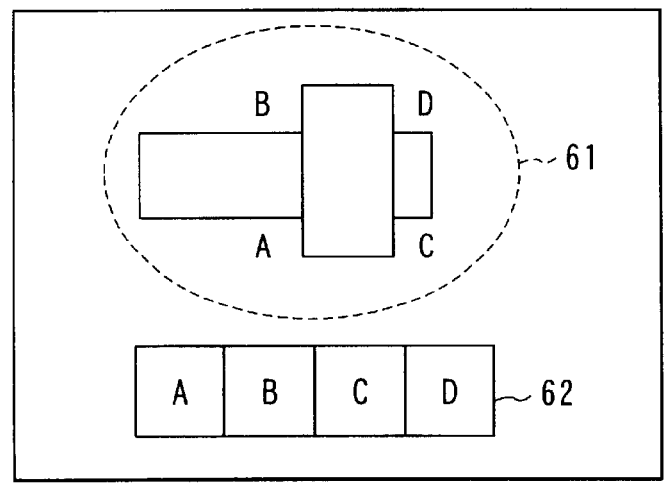
FIG. 6 is a view showing a second input device according to the first embodiment of the present invention.

FIG. 6 is a view showing a second input device. The second input device is a means for designating the standing position of the observer, and is provided in the input device 6 as in the first input device. That is, the input device 6 is provided to the gantry 1 or bed 2, or on the control cabinet 3, as shown in FIG. 1.

Referring to FIG. 6, reference numeral 60 denotes icons (iconic symbols) indicating the gantry, bed, and standing positions (A, B, C, and D) of the observer; and 61, a switch for designating to switch the image display method in accordance with the standing position of the observer. The switch 61 comprises a plurality of switches which correspond to standing positions A, B, C, and D of the observer in the icons 60, and incorporate LEDs.

When the operator presses one of the switches 61, a display method corresponding to one of standing positions A, B, C, and D indicated by the icons 61 can be designated.

Depression information of the switch 61 is sent to the main controller 30. The main controller 30 switches the image display method on the basis of this depression information. In this case, the main controller 30 controls the display processor 37 to change the display order of images along the slice direction.

Figure 7:
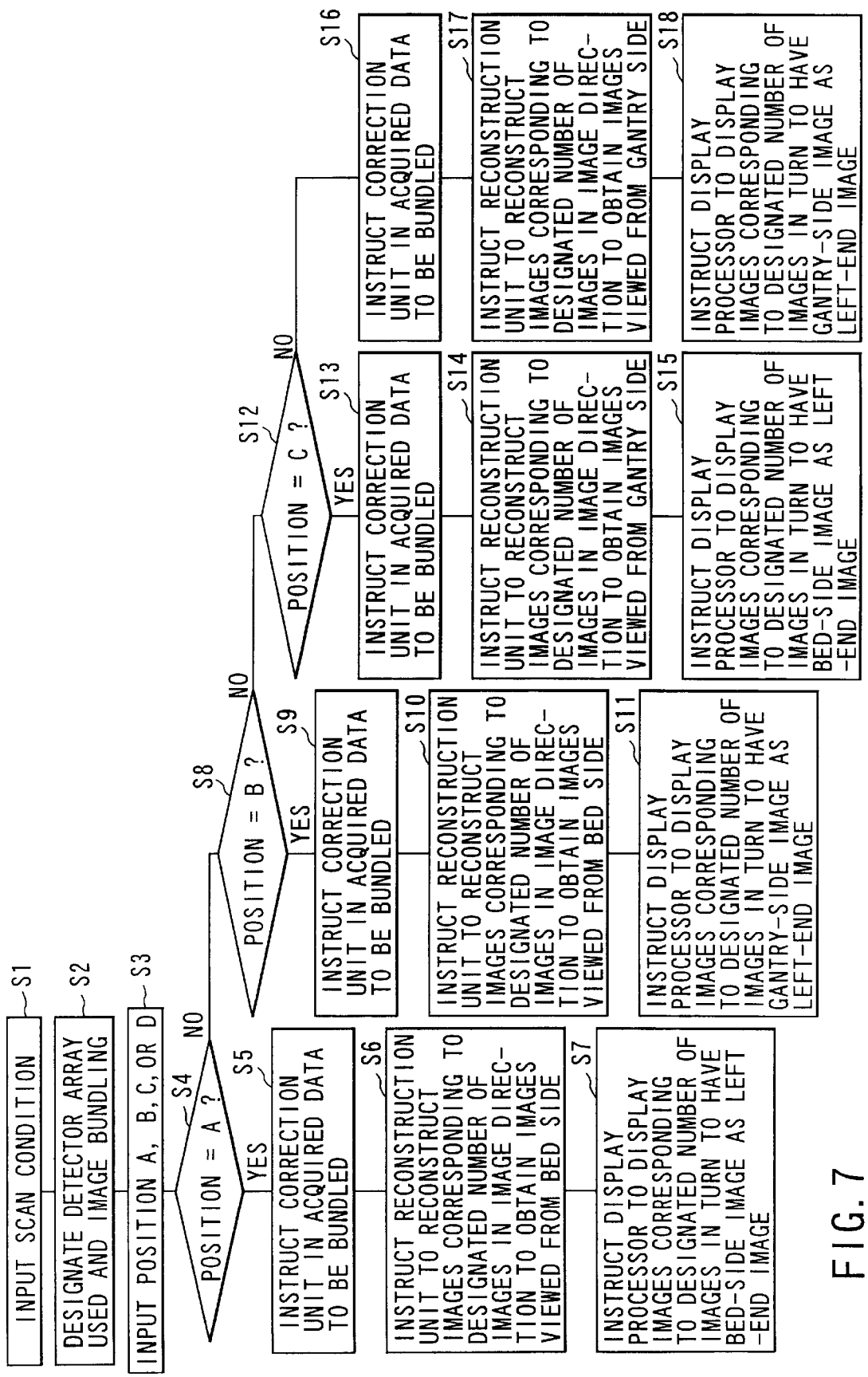
FIG. 7 is a flow chart showing the flow of a display order switching control method according to the first embodiment of the present invention.

FIG. 7 is a flow chart showing the flow of the image display order switching control method. This flow chart includes decision processes and the like implemented by the main controller 30 upon receiving a signal from the second input device (the designated standing position of the observer).

As shown in step S1, scan conditions are input. In step S2, designation that pertains to detector arrays used and images are bundled using the first input device described above.

In step S3, one of positions A, B, C, and D is input from the second input device.

In step S4, the input position is checked. That is, if the position input in step S3 is "A", the flow advances to step S5; otherwise, the flow advances to step S8.

If the flow advances to step S5, the main controller instructs the correction unit 34 in the way acquired data are bundled. In step S6, the main controller instructs the reconstruction unit 36 in the way images are reconstructed. In this case, since position "A" is selected, the main controller instructs to reconstruct images corresponding to the designated number of images in an image direction to obtain images viewed from the bed side. In step S7, the main controller instructs the display processor 37 in the display method. That is, the main controller instructs to display images corresponding to the designated number of images in turn to have an image on the bed side as the left-end image.

Note that the "image direction to obtain images viewed from the bed side" is a direction in which the top of the head of the patient is seen from his or her toe side, and conversely, an "image direction to obtain images viewed from the gantry side (to be described later)" is a direction in which the toe side of the patient is seen from the top of his or her head. When image directions are different in such cases, the right and left of the object are reversed on the display screen (the obverse/reverse side of a tomographic image).

On the other hand, if the flow advances from step S4 to step S8, the input position is further checked. That is, if the position input in step S3 is "B", the flow advances to step S9; otherwise, the flow advances to step S12.

If the flow advances to step S9, the main controller instructs the correction unit 34 in the way acquired data are bundled. In step S10, the main controller instructs the reconstruction unit 36 in the way images are reconstructed. In this case, since position "B" is selected, the main controller instructs to reconstruct images corresponding to the designated number of images in the image direction to obtain images viewed from the bed side. In step S11, the main controller instructs the display processor 37 in the display method. That is, the main controller instructs to display images corresponding to the designated number of images in turn to have an image on the gantry side as the left-end image.

On the other hand, if the flow advances from step S8 to step S12, the input position is further checked. That is, if the position input in step S3 is "C", the flow advances to step S13; otherwise, the flow advances step S16.

If the flow advances to step S13, the main controller instructs the correction unit 34 in the way acquired data are bundled. In step S14, the main controller instructs the reconstruction unit 36 in the way images are reconstructed. In this case, since position "C" is selected, the main controller instructs to reconstruct images corresponding to the designated number of images in the image direction to obtain images viewed from the gantry side. In step S15, the main controller instructs the display processor 37 in the display method. That is, the main controller instructs to display images corresponding to the designated number of images in turn to have an image on the bed side as the left-end image.

If the flow advances to step S16, the main controller instructs the correction unit 34 in the way acquired data are bundled. In step S17, the main controller instructs the reconstruction unit 36 in the way images are reconstructed. In this case, since position "D" is selected, the main controller instructs to reconstruct images corresponding to the designated number of images in the image direction to obtain images viewed from the gantry side. In step S18, the main controller instructs the display processor 37 in the display method. That is, the main controller instructs to display images corresponding to the designated number of images in turn to have an image on the gantry side as the left-end image.

Figure 8A:
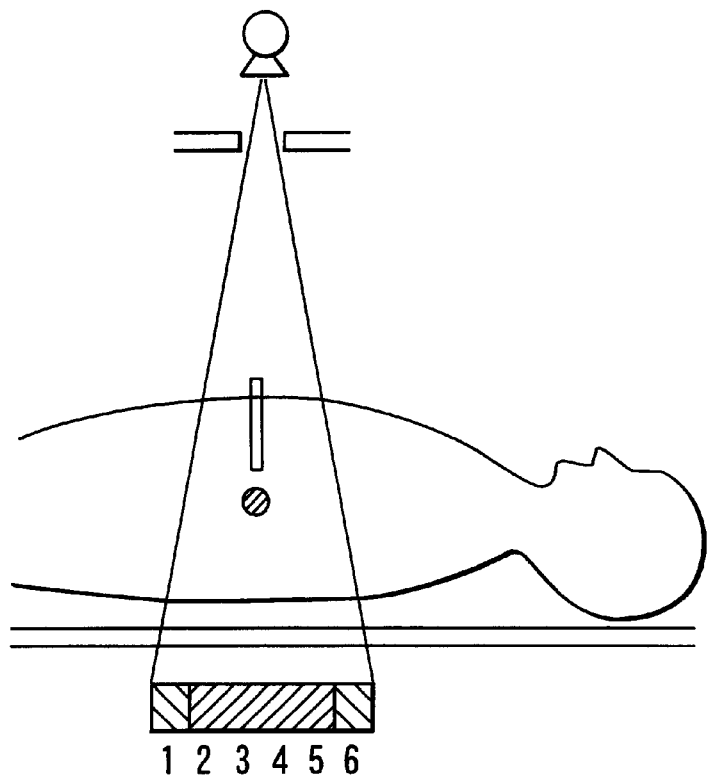
FIG. 8A is a view showing an initial state at the beginning of multi-slice CT fluoroscopy, and the aperture of a precollimator according to the first embodiment of the present invention.
Figure 8B:
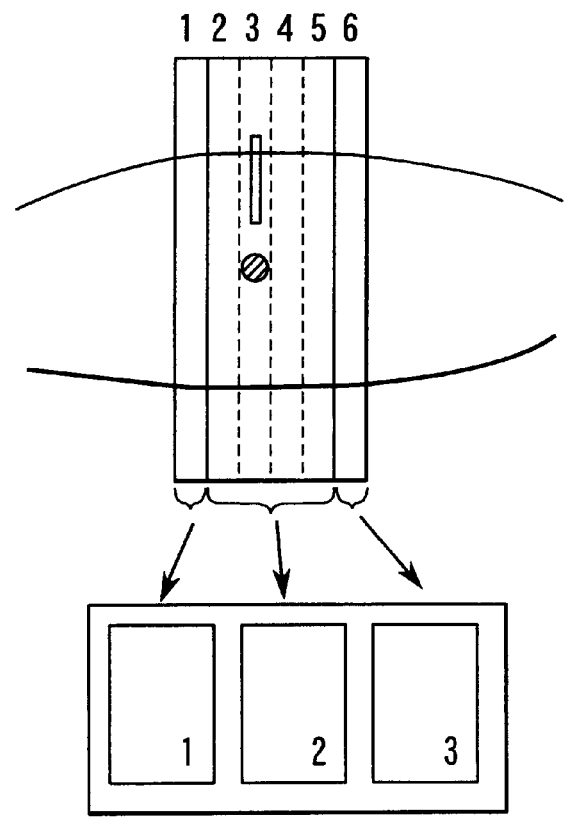
FIG. 8B is a view showing an initial state at the beginning of multi-slice CT fluoroscopy, and a plurality of slices of a patient and their displayed images according to the first embodiment of the present invention.

An initial state shown in FIGS. 8A and 8B will be examined below.

As shown in FIG. 9A, the precollimator 22 sets an aperture width corresponding to six detector arrays, and multi-slice CT fluoroscopy is started.

At this time, acquired data for six arrays are directly sent to the correction unit 34, and the data for four central arrays are bundled to obtain acquired data corresponding to three images, as shown in FIG. 9B. Three images are reconstructed within a time shorter than the time required per scan in the designated image direction in accordance with the instruction from the main controller 30, and are sent to the display processor 37.

[Display on Display]

The display processor 37 displays on the display 5 in accordance with the display order instruction from the main controller 30. In this case, images are displayed, as shown in FIG. 9C.

That is, when position A (bed C side) is designated and input at the second input device, three tomographic images line up and are displayed in turn. On the other hand, when position B (bed C side) is designated, three tomographic images line up and are displayed in the order opposite to that order.

Likewise, when position C (gantry G side) is designated and input at the second input device, three tomographic images line up and are displayed in turn. On the other hand, when position D (gantry G side) is designated and input, three tomographic images line up and are displayed in the order opposite to that order.

As described above, according to the first embodiment, even when the observer observes from any of directions A, B, C, and D, since images are displayed in an appropriate order to agree with the direction and location in which tomographic images of the patient are present, the operator can be prevented from mistaking upon making a centesis procedure. As a result, the centesis procedure can be efficiently done, and time required for the procedure can be shortened. As a result, not only in centesis procedures but also upon normally observing a fluoroscopic image, diagnosis errors can be prevented.

Note that the display 5 is laid out near the patient in this embodiment. Even when the display order control is executed for a display or the like placed on the control cabinet 3, the same effect can be obtained.

(Second Embodiment)

In the second embodiment, a means for automatically detecting the standing position of the observer is added to the system described in the first embodiment.

[Overall Arrangement]

Figure 10:
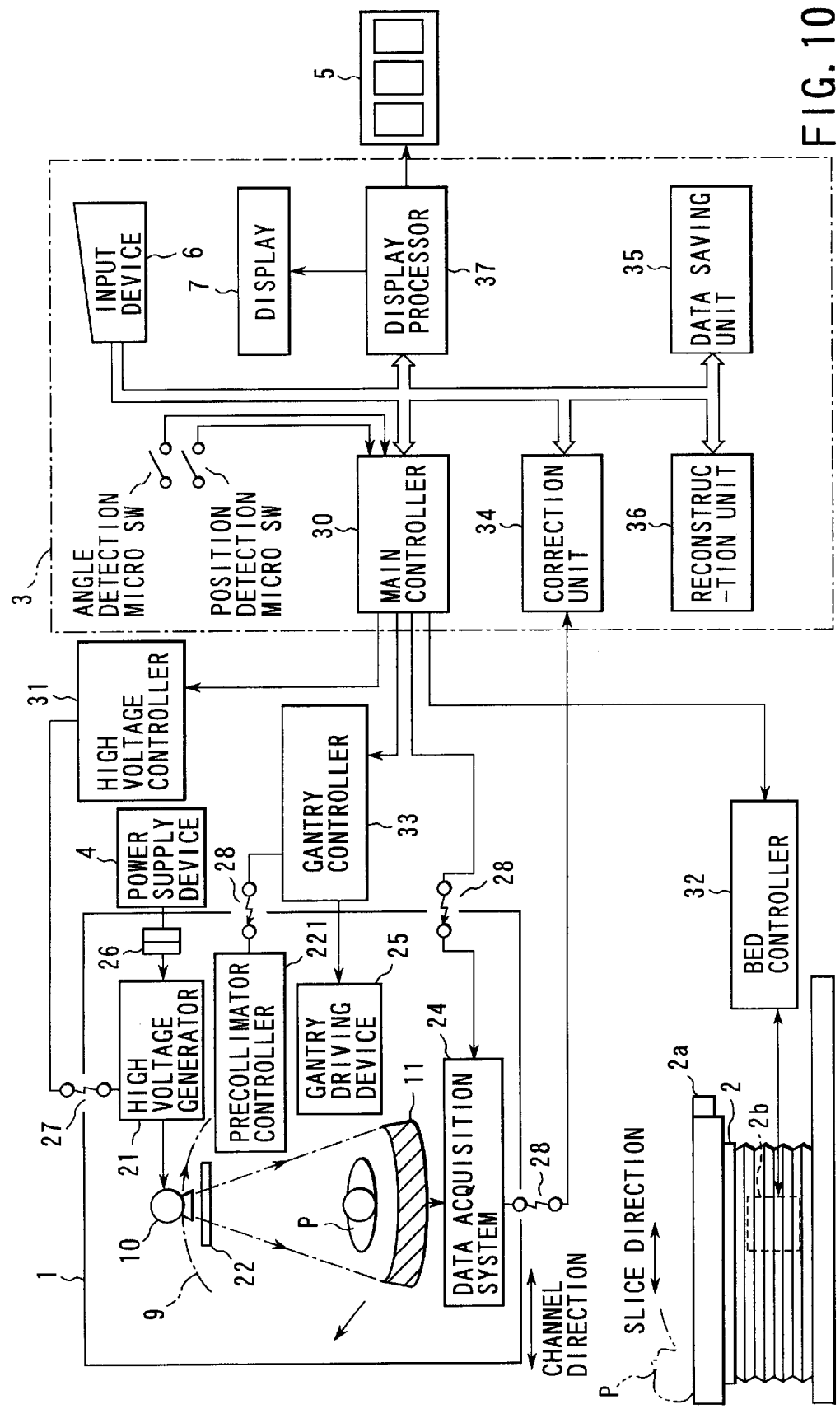
FIG. 10 is a block diagram showing a schematic arrangement of a multi-slice CT fluoroscopy system according to the second embodiment of the present invention.

FIG. 10 is a block diagram showing a schematic arrangement of a multi-slice CT fluoroscopy system according to the second embodiment of the present invention. This arrangement is substantially the same as that of the first embodiment, except that an angle detection micro switch (SW) and position detection micro switch (SW) for detecting the standing position of the observer are added, and the second input device shown in FIG. 6 is omitted.

[Detection of Standing Position of Observer]

FIG. 11 is a view showing a mechanism for detecting the standing position of the observer according to a characteristic feature of this embodiment.

The display 5 is suspended from a guide rail 111 (the guide rail 111 is arranged on the central axis), and is movable in the rotation axis direction. The display 5 comprises a member 112 which telescopes in the vertical direction, and can be set at an appropriate level by telescoping the member 112.

Also, to set a display direction in which the observer is easy to see, the display 5 is rotatable 360° about the telescopic member 112.

The position detection micro SW is provided to the display 5. This switch is means for detecting whether the display 5 is located in front of or on the back side of the gantry and, in this embodiment, a means for detecting if the display 5 is located at position A or B, or position C or D described above.

The angle detection micro SW is attached to a connecting portion between the display 5 and telescopic member 112. This switch is fixed to the display 5, and rotates integrally with the display 5. The angle detection micro SW is a means for detecting a direction in which the display 5 faces and, in this embodiment, a means for detecting based on its rotation angle whether the display 5 is located at position A or C mentioned above.

Figure 12:
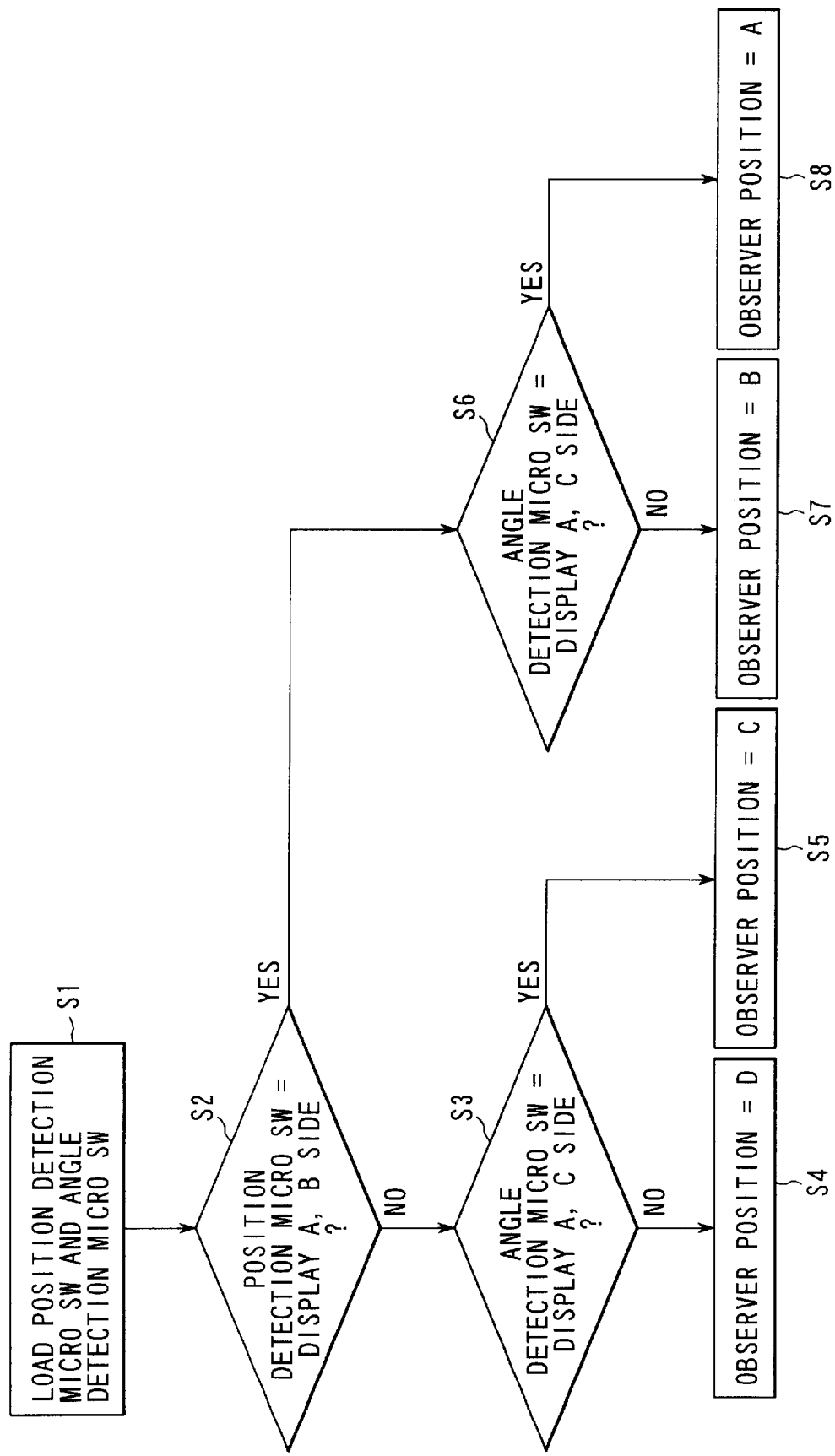
FIG. 12 is a flow chart showing a method of automatically detecting the standing position of the observer according to the second embodiment of the present invention.
Figure 14A:
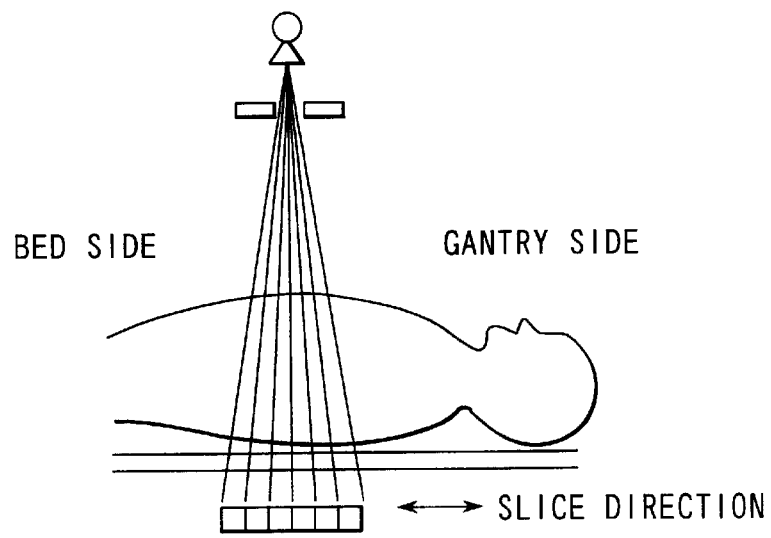
FIG. 14A is a view showing a case wherein a fluoroscopy mode of a total of two images is set, and the X-ray radiation state onto a patient according to a modification of the present invention.
Figure 14B:
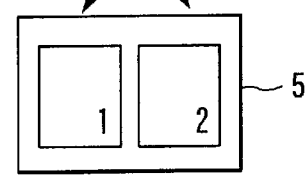
FIG. 14B is a view showing the case wherein the fluoroscopy mode of a total of two images is set, and a plurality of slices of the patient and their displayed images according to the modification of the present invention.
Figure 14C:
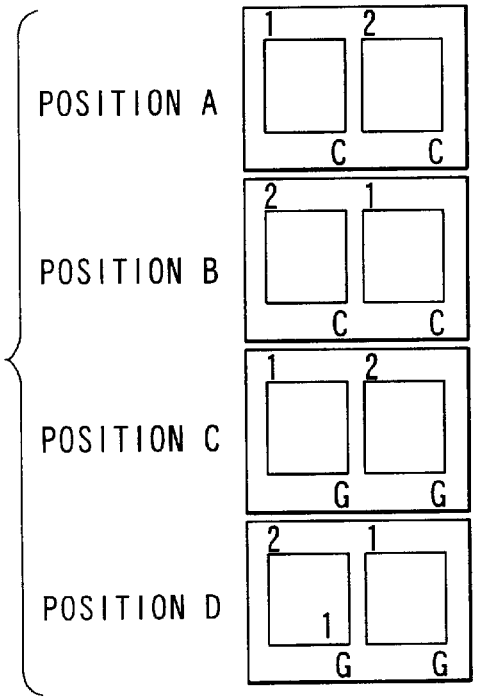
FIG. 14C is a view showing the case wherein the fluoroscopy mode of a total of two images is set, and an example of display according to the standing position of the observer according to the modification of the present invention.

According to these two micro SWs, position A, B, C, or D of the observer can be selectively and automatically detected. The flow of such automatic detection is shown in the flow chart in FIG. 12.

In step S1, detection information is loaded from the position detection micro SW and angle detection micro SW.

The flow advances to step S2 to check based on the detected position from the position detection micro SW if the display 5 is located on the side of position A or B.

If it is determined that the display 5 is located on the side of position A or B, the flow advances to step S6; otherwise, the flow advances to step S3.

It is then checked in step S3 based on the detected angle from the angle detection micro SW if the display 5 faces the side of position A or C.

If the display 5 faces the side of position A or C, it is detected that the position of the observer is "C" (step S5); otherwise, it is detected that the position of the observer is "D" (step S4).

On the other hand, if the flow advances from step S2 to S6, it is checked in step S6 based on the detected angle from the angle detection micro SW if the display 5 faces the side of position A or C, as in step S3.

If the display 5 faces the side of position A or C, it is detected that the position of the observer is "A" (step S8); otherwise, it is detected that the position of the observer is "B" (step S7).

In this manner, the standing position of the observer can be automatically detected.

The main controller 30 switches the image display method on the basis of the detected standing position information of the observer. This operation is the same as that in the first embodiment.

As described above, according to the second embodiment, fluoroscopic images can be arranged and displayed in an appropriate order in consideration of the obverse/reverse side and observation direction of tomographic images, as in the first embodiment.

Furthermore, since the standing position of the observer is automatically detected, the need for inputting the standing position of the observer using the input device, that has been explained in the first embodiment, can be obviated.

A modification of the second embodiment will be described below.

[Modifications Relating to Another Detection of Standing Position of Observer]

In the second embodiment, two micro SWs are provided to the display for the purpose of detecting the standing position of the observer. However, an arrangement for implementing equivalent detection is not limited to these micro SWs, and other means may be used.

For example, a photodetector for directly detecting the observer may be used, or non-contact detectors that emit laser beams into a space and receive reflected laser beams using photodiodes or the like may be attached in the vicinity of positions A, B, C, and D, and the standing position may be detected by detecting interception of a laser beam by the observer using the photodiodes.

Also, since a person normally "moves", motion detectors may be provided near positions A, B, C, and D. With this arrangement, the way the display is set becomes free from any limitations, and a monitor may be placed on a frame with rollers, thus reducing the setting cost of the display.

Various modifications of the first and second embodiments mentioned above will be explained below.

[Number of Images to be Displayed]

The number of images to be displayed and their slice thicknesses can be arbitrarily set. For example, the present invention can be applied to a case wherein a fluoroscopy mode of a total of five images is set by forming a single image by bundling data from two central arrays (detector arrays 3 and 4) in addition to four images formed based on data from two end arrays each (detector arrays 1 and 2, and 5 and 6). FIGS. 13A to 13D show an embodiment in this case.

Also, for example, the present invention can also be applied to a case wherein a fluoroscopy mode of a total of two images is set by bundling data from three end arrays each (detector examples 1 to 3, and 4 to 6) to form two images. FIGS. 14A to 14D show an embodiment in this case.

[Enlargement of Image of Interest]

In addition to the image order control according to the aforementioned principle of the present invention, an image of interest (central image) may be displayed in an enlarged scale, as shown in FIG. 9D or 13D.

The image of interest displayed near the center of the screen may be selectable from all images. Images other than the selected image are displayed in turn to have the bed- or gantry-side image as the left-end image. In this manner, since the image of interest is displayed in an enlarged scale while all images are displayed, images can be observed more easily, thus improving the diagnostic performance and operability.

[Display Method]

In the above embodiments, all images are displayed on a single display. However, the present invention is not limited to such specific image display method. For example, a plurality of images may be respectively displayed on independent displays. In this manner, the individual images can be displayed in an enlarged scale.

Also, a projector type large-scale display may be used. In such case, images can be displayed in an enlarged scale and can be observed more easily.

Furthermore, images may be displayed on a head-mounted display. Since images are displayed within the range of the field of view independently of the direction in which the operator faces, the operator need not look back to observe the display during, e.g., centesis procedures, thus improving operability.

[Application to Single-slice CT]

FIG. 15 shows an application example to single-slice CT. In this case, a single image viewed from the bed side is displayed at position A or B, and a single image viewed from the gantry side is displayed at position C or D. Since the obverse/reverse side of the image can be normally displayed, mistakes and diagnosis errors can be prevented.

[Type of CT]

In the above embodiments, third-generation CT (the X-ray source and detector synchronously move around the patient) has been exemplified, but the present invention is not limited to such specific CT. The present invention can also be applied to fourth-generation CT (the detector is laid out in a cylindrical pattern, and the X-ray generation source rotates), and to fifth-generation CT (an electron beam impinges against a fixed target laid out in a ring or cylindrical pattern to generate X-rays, which are received by a fixed detector).

[Type of Detector (50 Arrays, Surface Detector)]

In the above embodiments, CT having six detector arrays has been exemplified. However, the number of detector arrays is not limited to six. For example, the present invention can be applied to CT having a multi-slice CT having 50 arrays, and can also be applied to that using a surface detector represented by an image intensifier.

[Reconstruction Condition]

The reconstruction conditions for only some images may be set to be superior to or different from those for other images. For example, like the image of interest shown in FIG. 9D or 13D, different reconstruction conditions may be set among images by setting a 512×512 reconstruction matrix for only the image to be displayed in an enlarged scale, and a 256×256 reconstruction matrix for other images. Alternatively, longer image updating intervals other than that of the image of interest may be set to positively lower the temporal resolution. As a result, the reconstruction conditions of images other than the designated image are relaxed, and the computation power of the reconstruction unit can be reduced. Hence, cost of the reconstruction device can be reduced.

[Reconstruction Method]

The present invention does not depend on any specific image reconstruction method. For example, a reconstruction method that makes normal filter back-projection regardless of the angle of a beam (cone angle) in the rotation axis direction may be used, or a reconstruction method that reconstructs by back-projecting acquired data in accordance with their acquisition route in accordance with the angle of the beam in the rotation axis direction (proposed by Feldkamp et al.) may be used. Upon executing this Feldkamp reconstruction, acquired data of the respective arrays are not bundled by the aforementioned correction unit, but an image with a designated slice thickness is reconstructed upon reconstruction. According to this reconstruction method, image quality of reconstructed images obtained using a larger number of detector arrays can be improved.

[Location of Bundling]

In the above embodiments, a unit for bundling data is the correction unit. However, the unit for bundling data is not limited to the correction unit. For example, the data acquisition system (DAS) 24 may bundle data, the reconstruction device may bundle data before reconstructing an image, or images may be bundled after the reconstruction device reconstructs individual images. Even with these modifications, the same effect can be obtained by the apparatus as a whole.

To recapitulate, according to the first and second embodiments, an X-ray computed tomography apparatus which displays fluoroscopic images of individual slices by setting an appropriate display order or obverse/reverse side of images in accordance with the observation position of the observer in multi-slice CT fluoroscopy can be provided.

(Third Embodiment)

The third embodiment of the present invention will be described below. A characteristic feature of the third embodiment lies in precollimator aperture control and "bundling" of detector data in accordance with the setups of images of interest/non-interest. Other arrangements are the same as those in the first or second embodiment described above.

FIG. 16 is a view showing the arrangement of a designation means for designating the image of interest. This designation means is provided to any one of the gantry 1, bed 2, and control cabinet 3, and the input device 6 corresponds to this means in this embodiment.

As described above, the number of detection element arrays of the multi-slice detector 11 of this embodiment is six, and an image-of-interest designation switch 61 having six buttons with built-in LEDs is equipped accordingly. The individual buttons correspond to the detection element arrays, and when the operator presses the button of the detection element array corresponding to the image of interest via the switch 61, the LED in the pressed button is turned on. As a result, the image of interest can be designated. That is, the position and slice thickness of the image of interest along the slice direction can be designated.

Also, an image-of-interest shift switch 62 for entirely shifting the position of the image of interest by one array to the left or right along the slice direction is equipped.

The designation results of these switches 61 and 62 are sent to the main controller 30.

The main controller 30 computes the positions and slice thicknesses of the image of interest and images of non-interest on the basis of the designation results of the switches 61 and 62. The precollimator 221 controls the aperture width of the collimator 22 to include the image of interest and images of non-interest using the computation results.

FIG. 17A is a side view of a state in which X-rays emitted from the X-ray tube toward the patient enter the multi-slice detector. In FIG. 17A, reference symbol N denotes a needle endermically inserted into the patient P; and S, living body tissue to be examined.

An X-ray beam 100 generated by the X-ray tube 10 is transmitted through the patient P after its beam width in the slice direction is controlled by the precollimator 22, and then enters the multi-slice detector 11. FIG. 17A illustrates a case wherein the beam width of the X-ray beam 100 is limited by the precollimator 22 in accordance with the designation results of the switches 61 and 62 and, as a result, no X-rays enter the fifth and sixth detection element arrays of the multi-slice detector 11.

The precollimator 22 controls the beam width under the control of the precollimator controller 221. Note that the precollimator controller 221 controls the aperture width of the precollimator 22 in the slice direction so that the slice thickness of each image of non-interest becomes smaller than that of the image of interest.

Detection data from the respective detection element arrays are sent to the correction unit 34 via the DAS 24 and the like. The correction unit 34 bundles data for the image of interest from a plurality of detection element arrays of the multi-slice detector 11 based on the first number of data to be bundled, and bundles data for the images of non-interest from a plurality of detection element arrays of the multi-slice detector 11 by the second number of data to be bundled smaller than the first number of data to be bundled.

In case of the example shown in FIG. 17, data from the second and third detection element arrays of the multi-slice detector 11 are bundled for the image of interest, and the bundled data is output to the reconstruction unit 36. Also, as for the images of non-interest, data from the first and fourth detection element arrays of that detector 11 are directly output to the reconstruction unit 36 without being bundled.

The bundled data is sent to the reconstruction unit 36. The reconstruction unit 36 reconstructs the image of interest (tomographic image) roughly in real time on the basis of the bundled data, and also reconstructs the images of non-interests (tomographic images) in real time. The reconstructed images are supplied to the display 5 via the display processor 37, and are displayed in real time.

FIG. 17B is a view showing the way the image of interest and images of non-interest are displayed.

The image of interest reconstructed based on data obtained by bundling the second and third detection data is displayed on the second display area of the display 5.

The image of non-interest reconstructed based on the detection data from the first detection element array (one of two images on the two sides of the image of interest) is displayed on the first display area of the display 4.

The image of non-interest reconstructed based on the detection data from the fourth detection element array (the other of two images on the two sides of the image of interest) is displayed on the third display area of the display 4.

Upon setting the precollimator aperture and bundling, the main controller 30 of this embodiment operates as follows.

Figure 18:
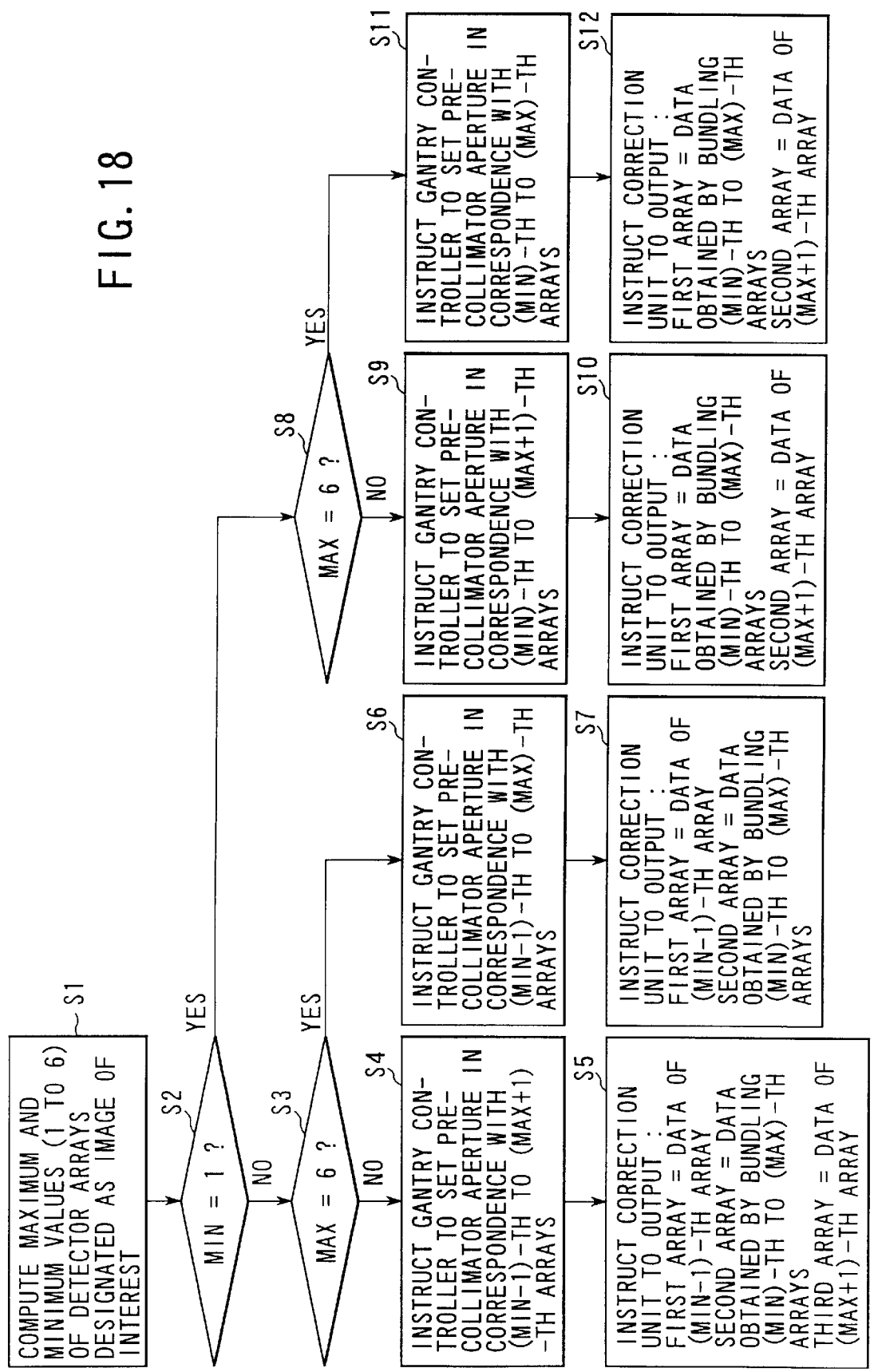
FIG. 18 is a flow chart showing the operation for setting the precollimator aperture and bundling.

FIG. 18 is a flow chart showing the operation for setting the precollimator aperture and bundling.

In step S1, the maximum and minimum values of the detection element arrays designated as the image of interest are substituted in variables MAX and MIN. Note that each of variables MAX and MIN assumes a value ranging from 1 to 6.

It is checked in step S2 if the value MIN is 1.

If the value MIN is not 1, the flow advances to step S3; if MIN=1, the flow advances to step S8.

It is checked in step S3 if the value MAX is 6.

If it is determined in step S3 that the value MAX is not 6, the main controller 30 operates as follows. That is, the main controller instructs the gantry controller 33 to set the aperture of the precollimator 22 in correspondence with (MIN−1)-th to (MAX+1)-th arrays (step S4), and also instructs the correction unit 34 to output:

first array=data of (MIN−1)-th array second array=data obtained by bundling (MIN)-th to (MAX)-th arrays third array=data of (MAX+1)-th array On the other hand, if it is determined in step S3 that MAX=6, the flow advances to step S6, and the main controller instructs the gantry controller 33 to set the aperture of the precollimator 22 in correspondence with (MIN−1)-th to (MAX)-th arrays, and also instructs the correction unit 34 to output:

first array=data of (MIN−1)-th array second array =data obtained by bundling (MIN)-th to (MAX)-th arrays If it is determined in previous step S2 that the value MIN is 1, and the flow advances to step S8, it is checked if the value MAX is 6.

Figure 19:
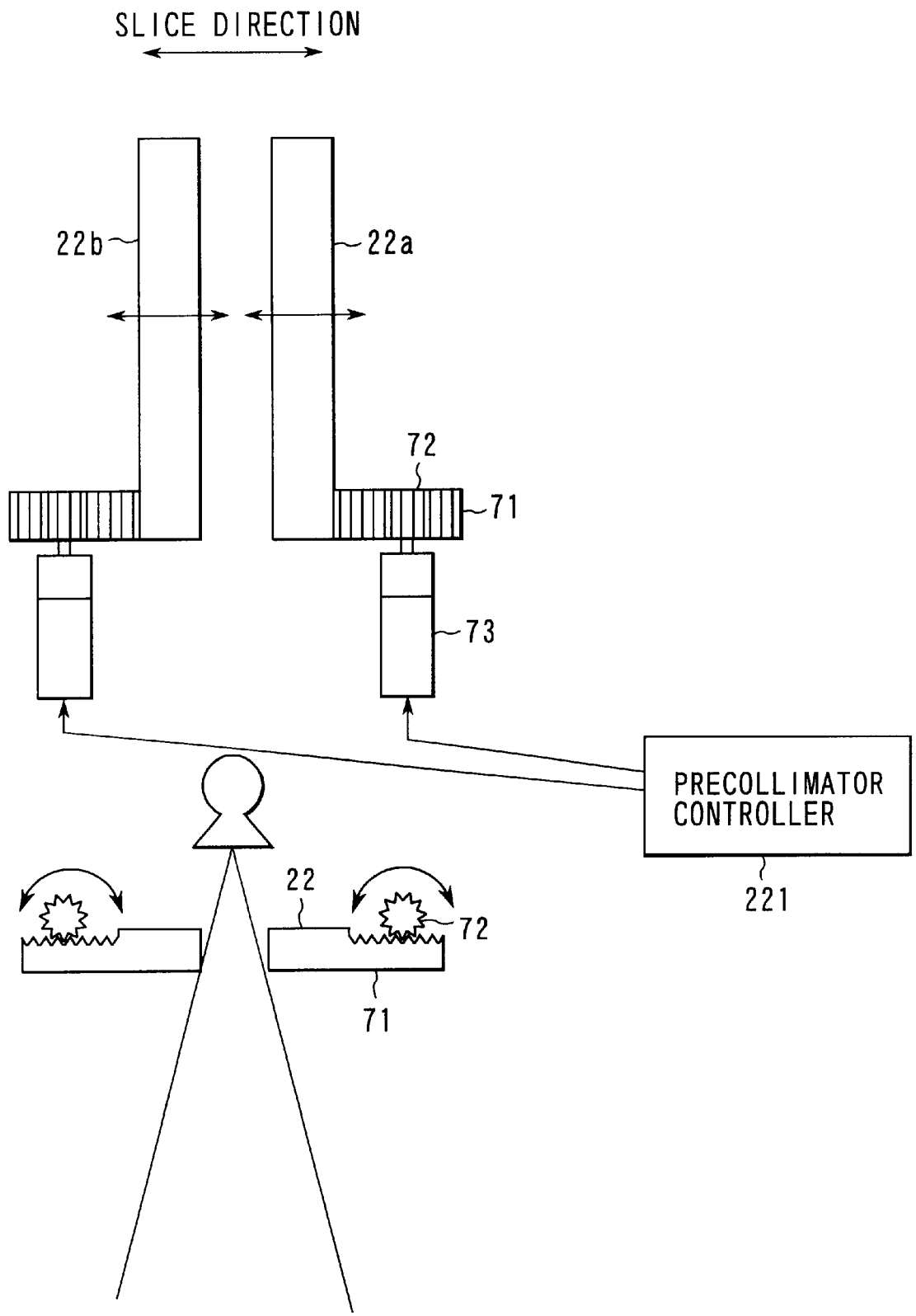
FIG. 19 is a view showing a control mechanism of the aperture width of the precollimator by a precollimator controller.

If the value MAX is 6, the flow advances to step S9, and the main controller instructs the gantry controller 33 to set the aperture of the precollimator 22 in correspondence with (MIN)-th to (MAX+1)-th arrays, and also instructs the correction unit 34 to output:

first array=data obtained by bundling (MIN)-th to (MAX)-th arrays second array=data of (MAX+1)-th array On the other hand, if MAX=6 in step S8, the flow advances to step S11, and the main controller instructs the gantry controller 33 to set the aperture of the precollimator 22 in correspondence with (MIN)-th to (MAX)-th arrays, and also instructs the correction unit 34 to output:

first array=data obtained by bundling (MIN)-th to (MAX)-th arrays second array=data of (MIN+1)-th array FIG. 19 is a view showing a mechanism for controlling the aperture width of the precollimator by the precollimator controller.

The precollimator controller 221 independently controls the positions of two blades 22a and 22b of the precollimator 22 in the rotation axis direction. On the other hand, the precollimator 22 outputs pulses indicating the operation positions of the two blades 22a and 22b.

Stepping motors (or servo motors) 73 drive pinion gears 72 to rotate via reduction gear mechanisms in accordance with the output pulses. The rotational forces of the pinion gears 72 are transmitted to rack gears 72 to convert rotations into linear motions, thus controlling the positions of the blades 22a and 22b of the precollimator 22.

The mechanism for controlling the aperture width of the precollimator shown in FIG. 19 is merely an example, and any other methods may be used as long as not only the aperture width but also the precollimator position can be controlled.

In this embodiment with the aforementioned arrangement, a series of operations upon executing multi-slice CT fluoroscopy will be explained below.

[Operation Under Initial Condition]

Figure 20A:
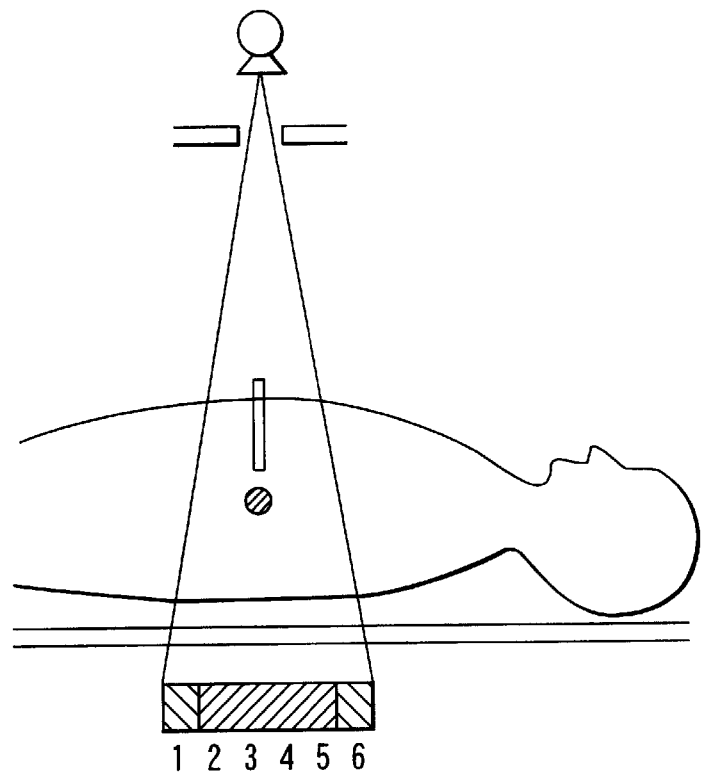
FIG. 20A is a view showing X-ray radiation onto a patient in an initial state.
Figure 20B:
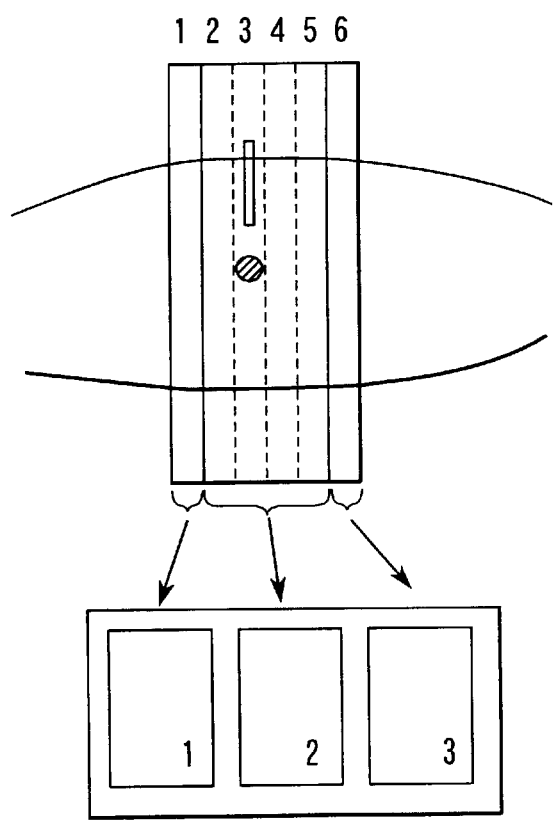
FIG. 20B is a view showing a plurality of slices of the patient in the initial state and their displayed images.

For example, assume that the aperture width corresponding to six detection element arrays is set as an initial condition of the precollimator 22, as shown in FIG. 20.

Multi-slice CT fluoroscopy under such setups is as follows. That is, acquired data for the six detection element arrays are directly sent to the correction unit 34, the data from the four central arrays are bundled to obtain data of the image of interest, and data of the first and sixth arrays respectively become data of default images of non-interest. In this manner, data corresponding to three images are obtained, and three images are reconstructed within a time shorter than the time required per scan and are displayed on the display 5 in real time.

[Operation Example 1 (1/4/1→1/3/1)]

When the currently displayed image of interest is to be observed with a smaller slice thickness in detail, the slice thickness of the image of interest can be changed by operating the image-of-interest designation switch 61 of the input device 6.

For example, three central arrays (detection element arrays 2, 3, and 4) are designated as the image of interest. Automatically, end arrays (detection element arrays 1 and 5) are respectively added as default images of non-interest, thus setting a fluoroscopy mode of a total of three images.

The operations for the collimator and bundling in this case are as follows.

Figure 21A:
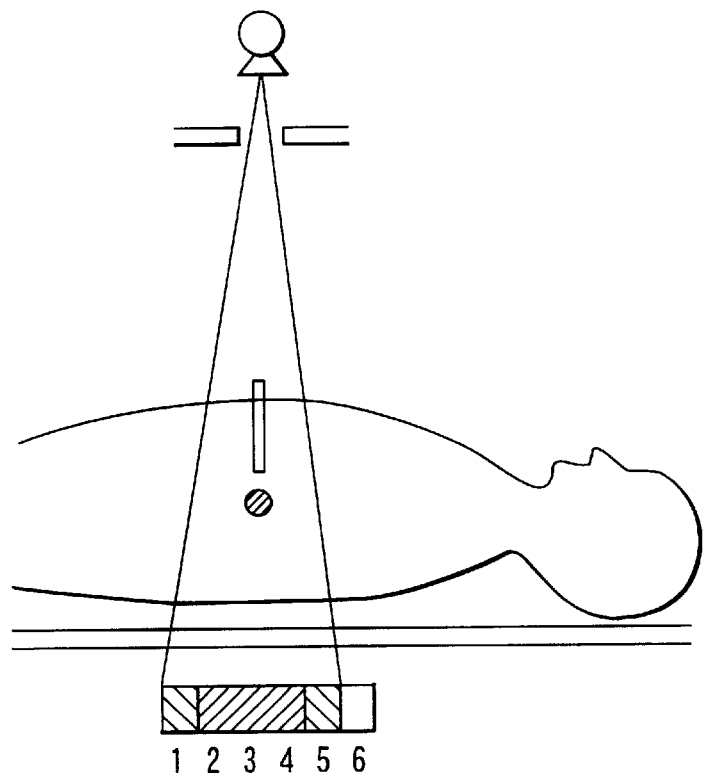
FIG. 21A is a view showing the state of the precollimator and detector in operation example 1.
Figure 21B:
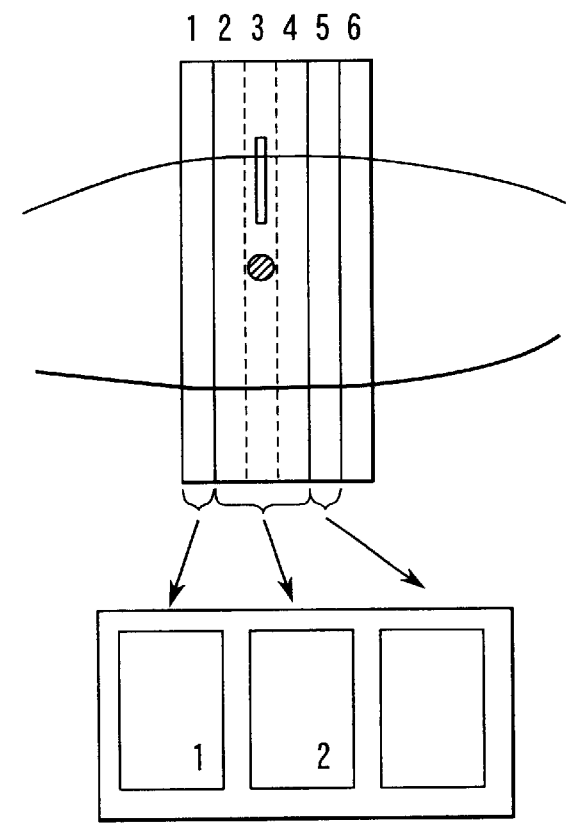
FIG. 21B is a view showing image display of a plurality of slices in operation example 1.

As shown in FIG. 21, the precollimator 22 is set to have an aperture width corresponding to five detection element arrays (detection element arrays 1 to 5), and acquired data for six arrays are directly sent to the correction unit 34. In this case, data for the sixth array is discarded. The first array, a bundle of the second, third, and fourth arrays, and the fifth array respectively generate acquired data correspond to three images, and three images are reconstructed within a time shorter than the time required per scan and are displayed on the display 5 in real time. Note that the top plate 2a may be moved so that the portion of the patient P, which corresponds to the center between detection element arrays 3 and 4 may be located at the center of the third array.

[Operation Example 2 (1/3/1→1/2/1)]

When the image of interest is to be observed with a still smaller slice thickness, the slice thickness is changed again by the image-of-interest designation switch 61 of the input device 6. For example, two central arrays (detection element arrays 3 and 4) are re-designated as the image of interest. Automatically, end arrays (detection element arrays 2 and 5) are respectively added as default images of non-interest, thus setting a fluoroscopy mode of a total of three images.

The operations for the collimator and bundling in this case are as follows.

Figure 22A:
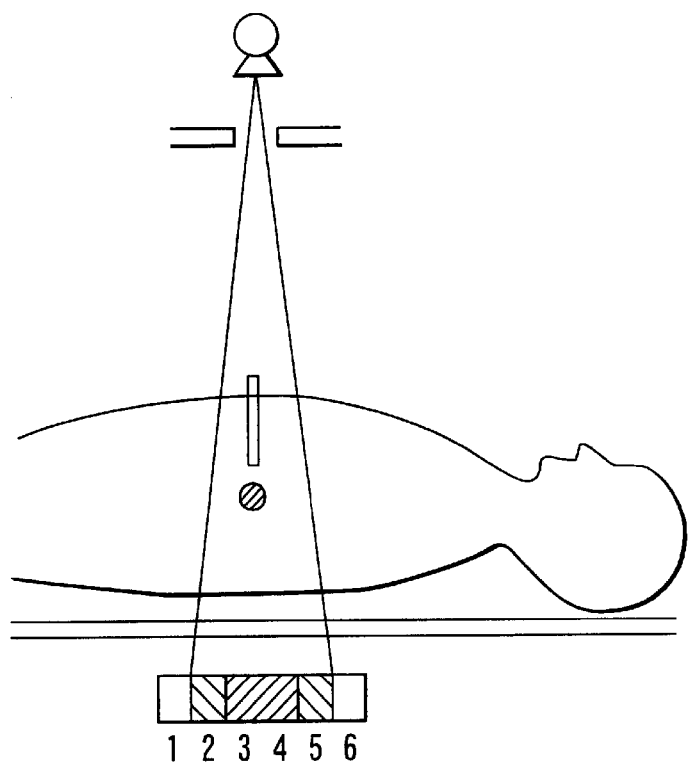
FIG. 22A is a view showing the state of the precollimator and detector in operation example 2.
Figure 22B:
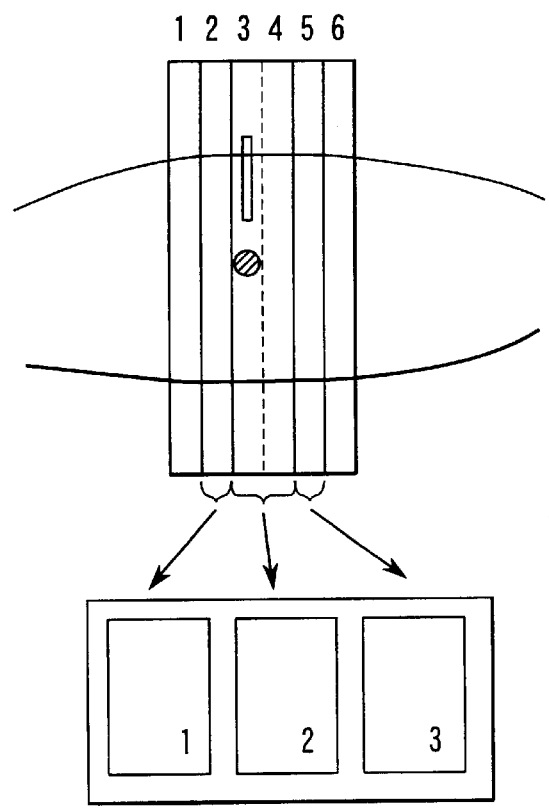
FIG. 22B is a view showing image display of a plurality of slices in operation example 2.

As shown in FIG. 22, the precollimator 22 is set to have an aperture width corresponding to four detection element arrays (detection element arrays 2 to 5), and acquired data for six arrays are directly sent to the correction unit 34. In this case, data for the first and sixth end arrays are discarded. The second array, a bundle of the third and fourth arrays, and the fifth array respectively generate acquired data corresponding to three images, and three images are reconstructed within a time shorter than the time required per scan and are displayed on the display 5 nearly in real time.

[Operation Example 3 (Shift 1 of Image of Interest with 1/2/1)]

When the image of interest is to be observed upon being shifted to the right or left position, the image-of-interest shift switch 62 is used. Alternatively, the slice thickness may be changed again using the image-of-interest designation switch 61. For example, two arrays (detection element arrays 2 and 3) are re-designated as the image of interest. Automatically, end arrays (detection element arrays 1 and 4) are added as default images of non-interest, thus setting a fluoroscopy mode of a total of three images.

Figure 23A:
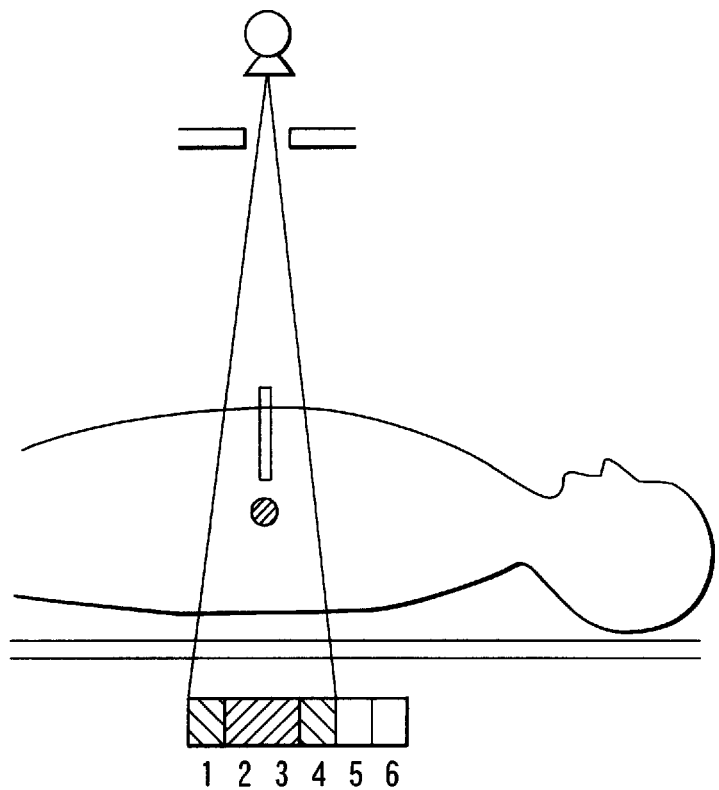
FIG. 23A is a view showing the state of the precollimator and detector in operation example 3.
Figure 23B:
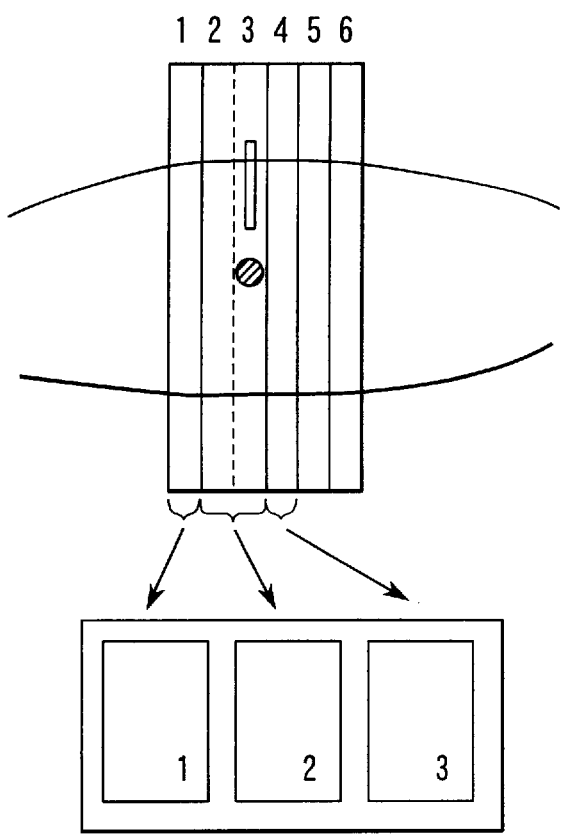
FIG. 23B is a view showing image display of a plurality of slices in operation example 3.

As shown in FIG. 23, the precollimator 22 is set at an aperture width corresponding to four detection element arrays (detection element arrays 1 to 4), and acquired data for six arrays are directly sent to the correction unit 34. In this case, the data for the fifth and sixth end arrays are discarded. The first array, a bundle of the second and third arrays, and the fourth array respectively generate acquired data corresponding to three images, and three images are reconstructed within a time shorter than the time required per scan and are displayed on the display 5 nearly in real time.

[Operation Example 4 (Shift 2 of Image of Interest with 1/2/1)]

When the image of interest is to be observed upon being further shifted laterally, the image-of-interest shift switch 62 is operated or the slice thickness is changed again using the image-of-interest designation switch 61. For example, two arrays (detection element arrays 1 and 2) are re-designated as the image of interest. Automatically, detection element array 3 is added as a default image of non-interest, thus setting a fluoroscopy mode of a total of two images.

Figure 24A:
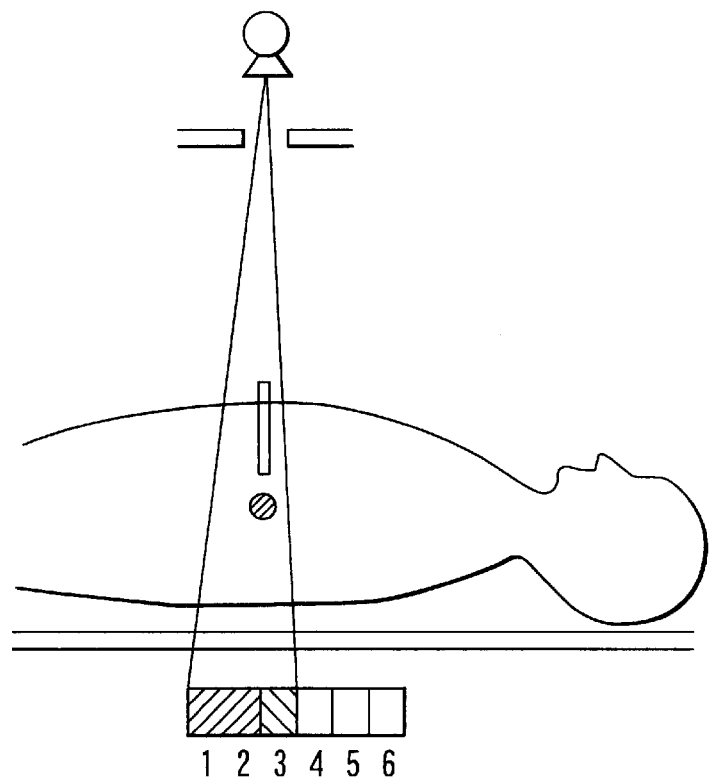
FIG. 24A is a view showing the state of the precollimator and detector in operation example 4.
Figure 24B:
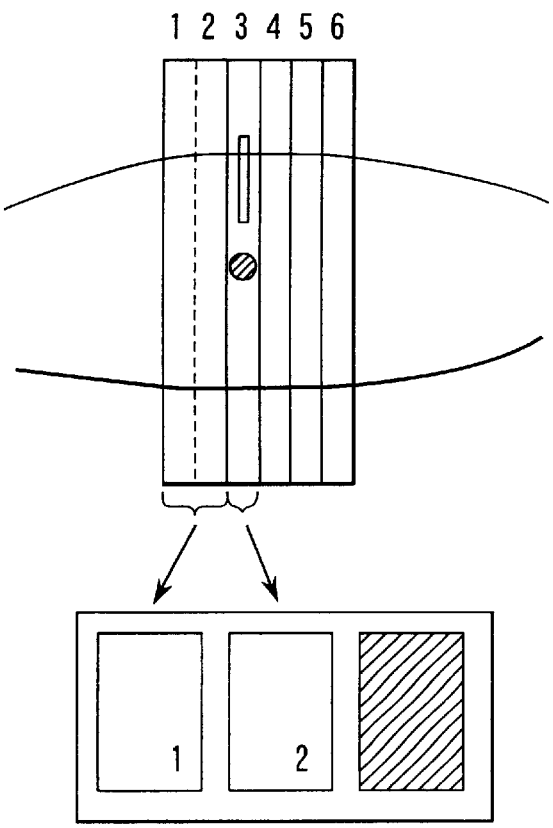
FIG. 24B is a view showing image display of a plurality of slices in operation example 4.

As shown in FIG. 24, the precollimator 22 is set at an aperture width corresponding to three detection element arrays (detection element arrays 1 to 3), and acquired data for six arrays are directly sent to the correction unit 34. In this case, the data for the fourth, fifth, and sixth end arrays are discarded. A bundle of the first and second arrays, and the third array respectively generate acquired data corresponding to two images, and two images are reconstructed within a time shorter than the time required per scan and are displayed on the display 5 nearly in real time.

Figure 25:
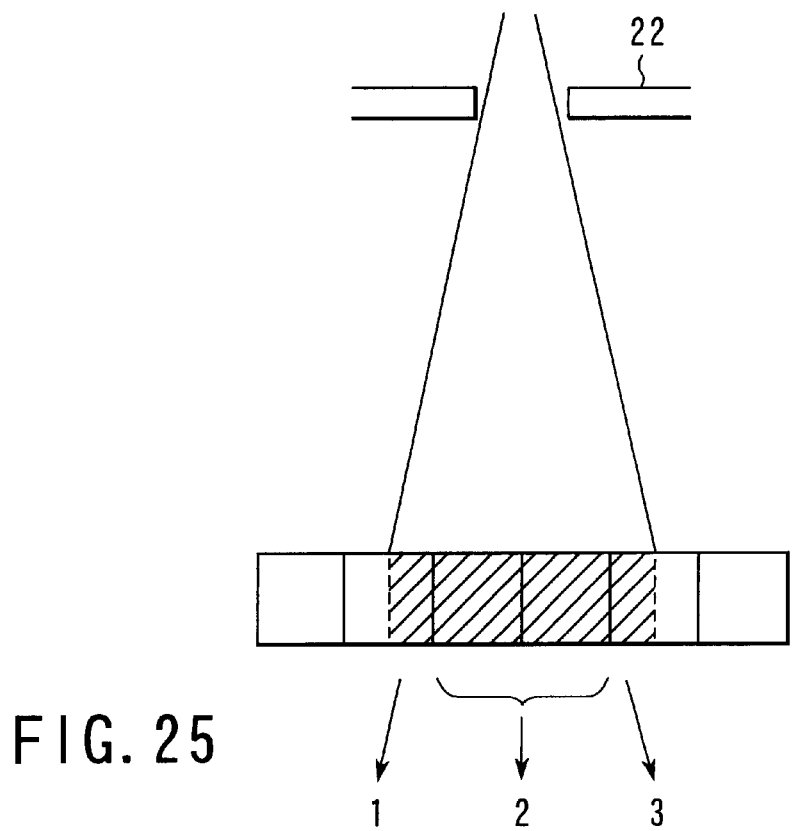
FIG. 25 is a view showing a case wherein the aperture width of the precollimator is narrowed down.

As shown in FIG. 25, the aperture width of the precollimator 22 may be controlled to narrow down the width of X-ray beam, which enters the detection element arrays corresponding to images of non-interest on the two ends of the image of interest, in the slice direction by a predetermined amount along the central direction of the image of interest.

Since the aforementioned multi-slice CT fluoroscopy system of this embodiment controls the aperture width of the recollimator 22 so that the slice thickness of each image of non-interest becomes smaller than that of the image of interest, and sets the number of detection element data to be bundled for each image of non-interest to be smaller than that for the image of interest, the dose on the patient can be reduced as the slice thickness of each image of non-interest becomes smaller than that of the image of interest.

Although the image quality of each image of non-interest deteriorates due to a decrease in slice thickness, deviation of a needle can be sufficiently confirmed. For this reason, the dose on the patient can be reduced without impairing required functions.

Various modifications of the third embodiment will be described below.

(1) Slice Thickness of Image of Non-interest

Images respectively corresponding to end arrays of the image of interest are automatically set, but the present invention is not limited to this. For example, in case of multi-slice CT having a total of 20 detection element arrays, detection element data for two arrays may be bundled to obtain a single default image of non-interest. In this manner, image noise can be reduced. Also, the number of arrays that form each default image may vary in correspondence with the size of the object to be sensed. For example, one array may be set for the image sensing condition of the head, and two arrays are set for that of the abdomen.

(2) Number of Images of Non-interest

In this embodiment, one each images before and after the image of interest are set, but the present invention is not limited to this. In case of multi-slice CT having a total of 20 detection element arrays, five images of non-interest each may be obtained before and after the slice of interest, and CT fluoroscopy in units of five images of non-interest may be made. In this manner, CT fluoroscopy that improves resolution in the slice direction can be implemented.

(3) Function of Manually Changing Displayed Image

Figure 26A:
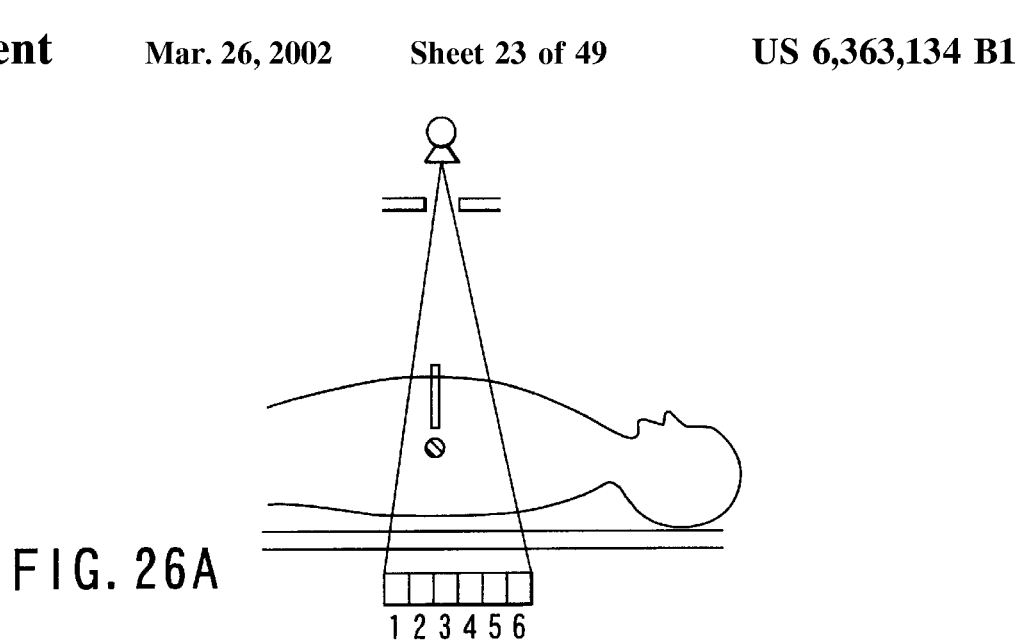
FIG. 26A is a view for explaining a manual displayed image change function, and the X-ray radiation state onto a patient.
Figure 26B:
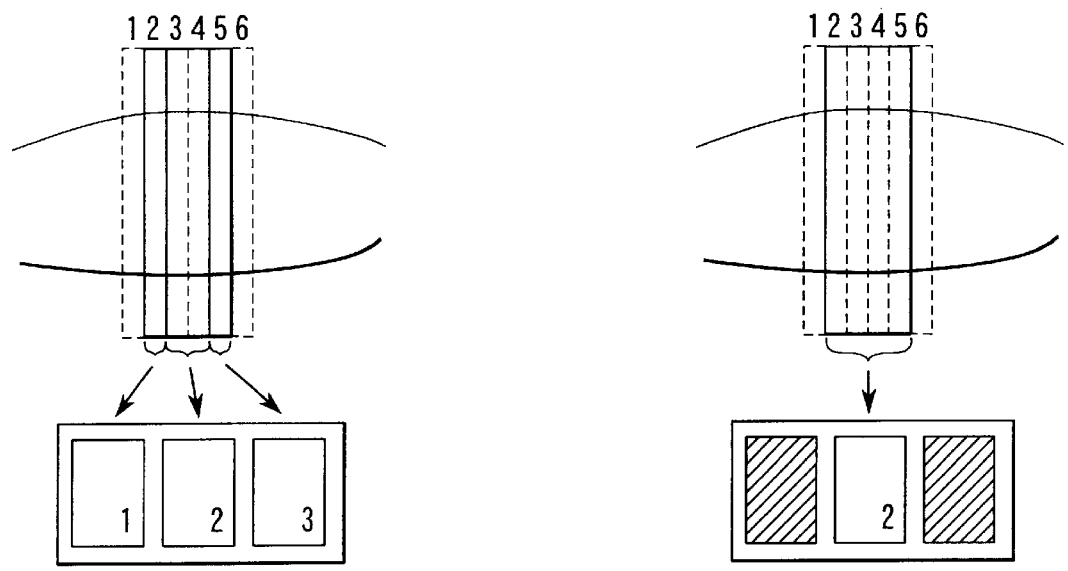
FIG. 26B is a view for explaining the manual displayed image change function, and the first display state.
Figure 26C:
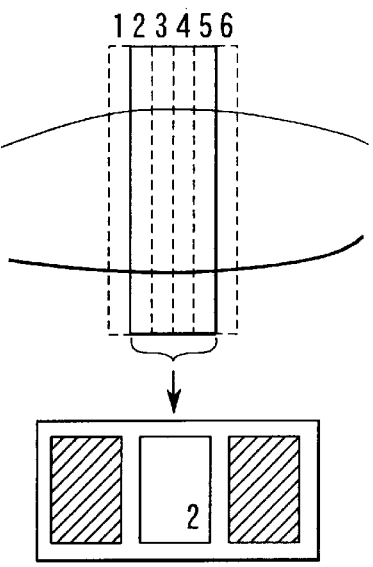
FIG. 26C is a view for explaining the manual displayed image change function, and the second display state.
Figure 26D:
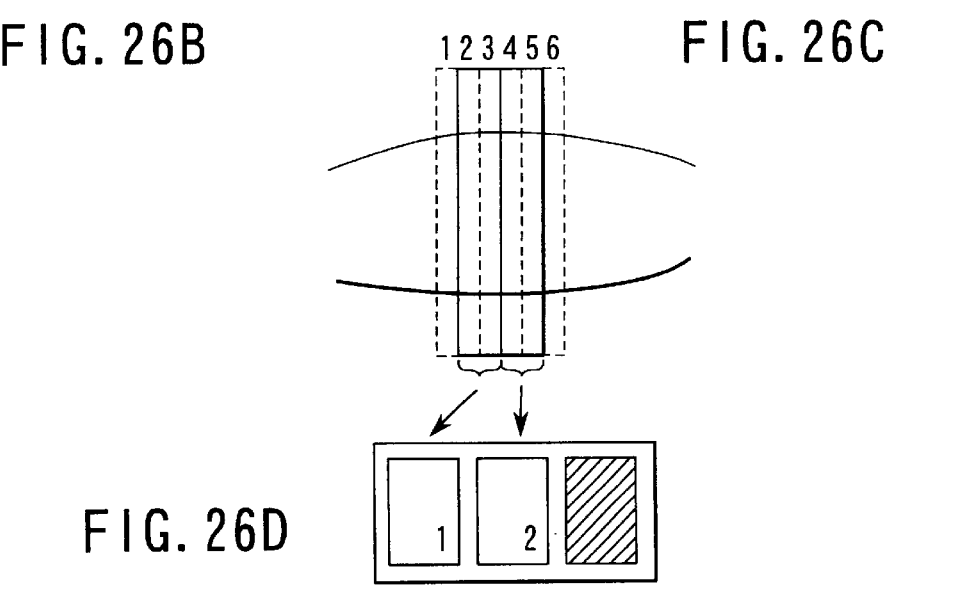
FIG. 26D is a view for explaining the manual displayed image change function, and the third display state.

The aforementioned three fluoroscopic images are default images, and the number of fluoroscopic images may be manually set. For example, three fluoroscopic images shown in FIG. 26B may be bundled into a single image, as shown in FIG. 26C, or may be bundled into two images, as shown in FIG. 26D. That is, in addition to the default setups, i.e., two end images before and after the image of interest, the number of displayed images can be arbitrary set. In this manner, the degree of freedom in fluoroscopy can improve, and various diagnostic cases can be coped with.

(4) Move Top Plate in place of Collimator (Shift with 1/2/1)

Movement of the image of interest (i.e., movement of a bundle) by changing the collimator 22 and the processing contents of the correction unit 34 upon operation of the image-of-interest shift switch 62 of the input device 6 has been explained. Instead, the top plate 2 is moved stepwise by an amount corresponding to one detection element array.

In this case, the positions of images shift relative to the patient P without changing the operations of the collimator 22 and correction unit 34, thus obtaining the same effect. This modification also has a merit of minimizing the cone angle.

Figure 27:
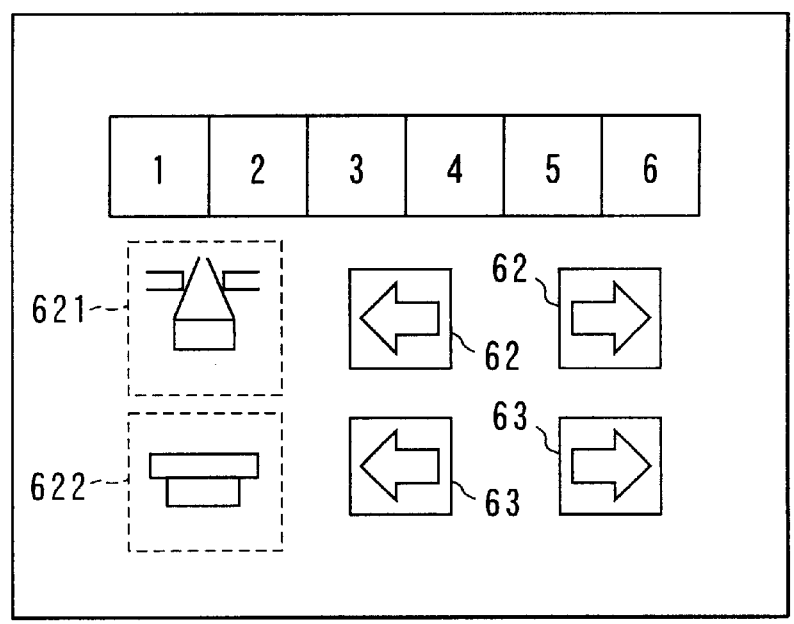
FIG. 27 is a view showing a case wherein image of interest moving switches for moving a top plate are added.

On the other hand, as shown in FIG. 27, an image-of-interest shift switch 63 for moving the top plate may be provided to the input device 6 in addition to the image-of-interest shift switch 62 for shifting the collimator and a bundle in the correction unit. Referring to FIG. 27, reference numeral 621 denotes an icon which represents the operation of the image-of-interest shift switch 62; and 622, an icon which represents the operation of the image-of-interest shift switch 63.

By selectively using the two switches, examinations can be made in different operation modes in correspondence with a case wherein the patient P must not be moved like in a surgical procedure and a case wherein the patient P can be moved like in a normal examination, thus further improving operability.

Various modifications in a broader aspect of the third embodiment will be explained below.

(1) Type of CT

In the above embodiment, third-generation CT (the X-ray source and detector synchronously move around the patient) has been exemplified, but the present invention is not limited to such specific CT. The present invention can also be applied to fourth-generation CT (the detector is laid out in a cylindrical pattern, and the X-ray generation source rotates), and to fifth-generation CT (an electron beam impinges against a fixed target laid out in a ring or cylindrical pattern to generate X-rays, which are received by a fixed detector).

(2) Type of Detector (50 Arrays, Surface Detector)

In the above embodiment, CT having six detector arrays has been exemplified. However, the number of detector arrays is not limited to six. For example, the present invention can be applied to CT having a multi-slice CT having 50 arrays, and can also be applied to that using a surface detector represented by an image intensifier, thus obtaining the same effects as in the above embodiment.

(3) Reconstruction Condition of Image of Interest

The reconstruction condition for the image of interest may be set to be superior to that for each image of non-interest or their reconstruction conditions may be set to be different from each other. For example, the image of interest may use a 512×512 reconstruction matrix, and each image of non-interest a 256×256 reconstruction matrix. Alternatively, longer image updating intervals for each image of non-interest than those for the image of interest may be set to positively lower the temporal resolution, thus relaxing the reconstruction condition to reduce the operation load on the reconstruction unit. Hence, the price (cost) of the reconstruction device can be reduced.

(4) Reconstruction Method

The present invention does not depend on any specific image reconstruction means. For example, a reconstruction method that makes normal filter back-projection regardless of the angle of a beam (cone angle) in the rotation axis direction may be used, or a reconstruction method that reconstructs by back-projecting acquired data in accordance with their acquisition route in accordance with the angle of the beam in the rotation axis direction (proposed by Feldkamp et al.) may be used. In this case, acquired data of the respective arrays are not bundled by the aforementioned correction unit, but an image with a slice thickness designated upon reconstruction is reconstructed. In this manner, image quality of reconstructed images using a larger number of detector arrays can be improved.

(5) Display Method

In the above embodiment, all images are displayed on the single display. However, the present invention is not limited to such specific image display method. For example, a plurality of images may be respectively displayed on independent displays. In this manner, the display areas of the individual images can be broadened.

Also, a projector type display may be used. In this case, images can be displayed in a very enlarged scale and can be observed more easily.

Furthermore, a head-mounted display (HMD) may be used. In such case, since images are displayed within the range of the field of view independently of the direction in which the operator faces, the operator need not look back to observe the display during, e.g., the centesis procedures, and the load on the operator can be reduced, thus improving operability.

(6) Location of Bundling

In the above embodiment, a unit for bundling data is the correction unit 34, but the present invention is not limited to such specific unit. For example, the data acquisition system (DAS) 24 may execute a process pertaining to data bundling, or image bundling may be done after individual images are reconstructed. In any case, the same effects as in the above embodiment can be obtained.

(7) Superposed Display of Image

In the above embodiment, a plurality of images are displayed in a line. However, the present invention is not limited to such specific image display method. Three images having different slice positions may be generated in correspondence with R, G, and B, and may be superposed to display a single image.

Figure 28A:
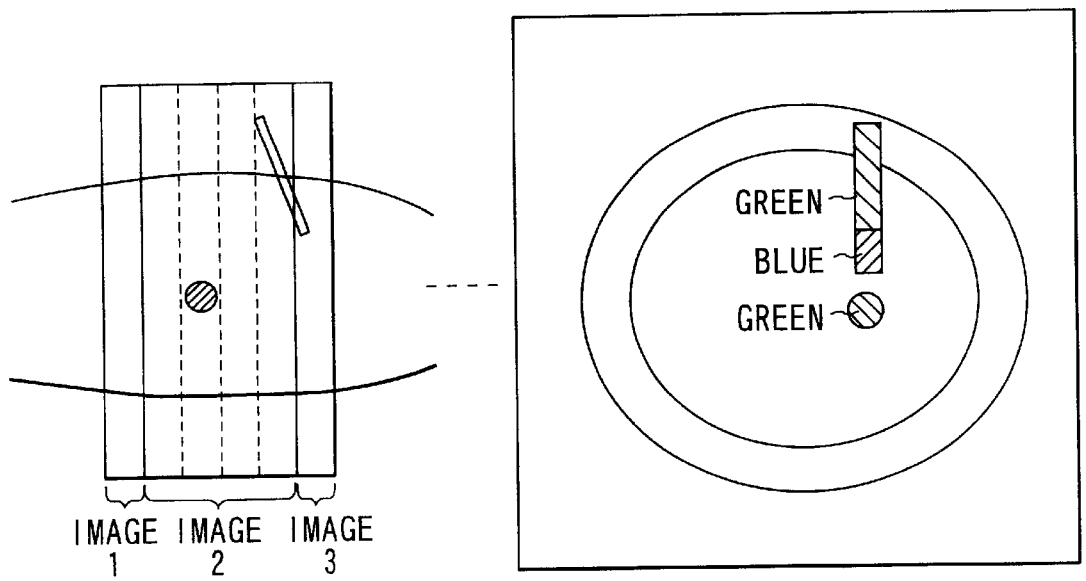
FIG. 28A is a view showing the first display state as an example of superposed display.
Figure 28B:
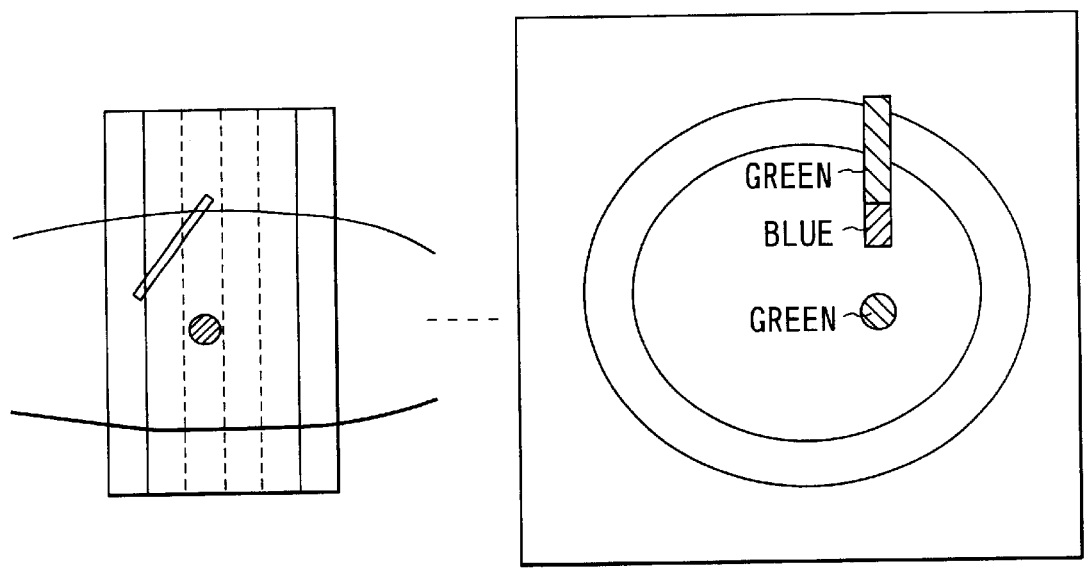
FIG. 28B is a view showing the second display state as an example of superposed display.

FIG. 28 is a view showing an example of such RGB superposed display.

Assume that image 1 is an R (red) image, image 2 a G (green) image, and image 3 a B (blue) image, and these images are set in correspondence with CT values by:

$$\text{Image 1: CT value=MIN}\rightarrow\text{MAX: RED=0}\rightarrow 255$$
$$\text{Image 2: CT value=MIN}\rightarrow\text{MAX: GREEN=0}\rightarrow 255$$
$$\text{Image 3: CT value=MIN}\rightarrow\text{MAX: BLUE=0}\rightarrow 255 \quad (1)$$

The image of interest is displayed in green. Note that MIN and MAX correspond to the window width of a CT value to be displayed, and can be arbitrarily set by the observer. As a result, the images are expressed by:

$$\text{RED=CT value (image 1)}$$
$$\text{GREEN=CT value (image 2)}$$
$$\text{BLUE=CT value (image 3)} \quad (2)$$

For example, when a needle deviates to a slice position corresponding to image 1 or 3, the color of the needle displayed changes to red or blue. That is, the operator can detect deviation of the needle on the basis of the change in color of the needle on the image.

In this case, three images are taken as an example, but the number of images is not limited to three. The present invention can be applied to two images or four or more images. In this manner, since the observer need only observe only one image, and the position of the insertion (needle) can be clearly indicated by color, the insertion can be observed more easily.

As described above, according to the third embodiment of the present invention, an X-ray computed tomography apparatus which can reduce the dose on the patient upon multi-slice CT fluoroscopy of the image of interest and images of non-interest near the image of interest can be provided.

(Fourth Embodiment)

The fourth embodiment of the present invention will be described below.

The fourth embodiment relates to multi-slice CT fluoroscopy that displays differentially processed images.

In a system of this embodiment, the number of images to be displayed corresponding to slice positions, and the slice thickness of each image can be arbitrarily set. In this system, data from the first and second arrays of the detector arrays are bundled to obtain a single image, data from the third and fourth arrays are bundled to obtain a single image, and data from the fifth and sixth arrays are bundled to obtain a single image, thus practicing a fluoroscopy mode of a total of three images.

[Input Device]

Figure 29:
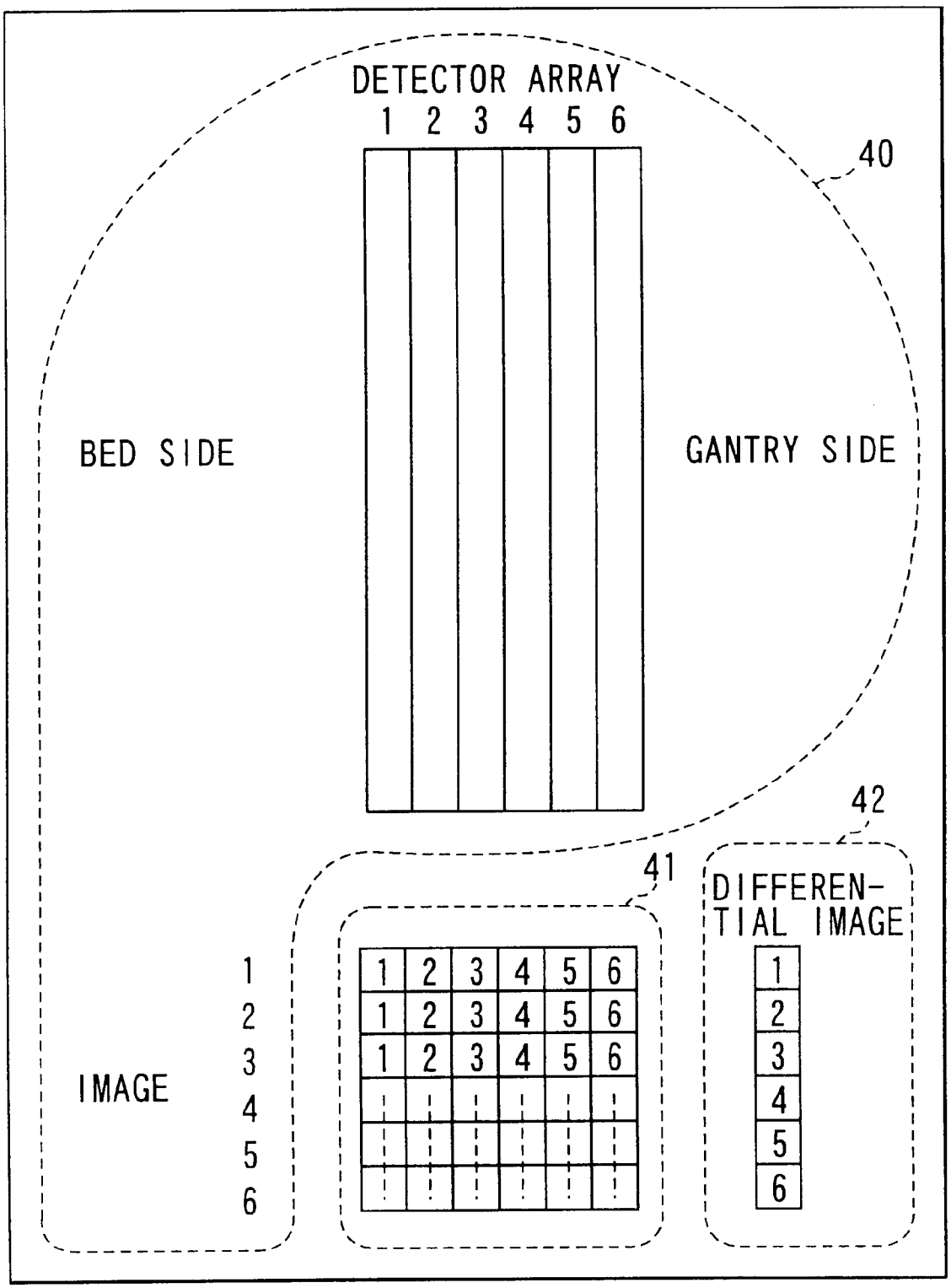
FIG. 29 is a view showing an input device according to the fourth embodiment.

FIG. 29 is a view showing an input device of this embodiment. This input device is a means for designating detector arrays to be used, image bundling, and differentially processed images, and is provided in the input device 6. Note that the input device 6 is provided to the gantry 1 or bed 2, or on the control cabinet 3, as shown in FIG. 1.

Referring to FIG. 29, reference numeral 40 denotes icons (iconic symbols) indicating the numbers of detector arrays, the gantry side and bed side, and the numbers of images; 41, a plurality of buttons which include LEDs, and make the number of detector arrays correspond to those of images; and 42, a plurality of buttons which include LEDs like in the buttons 41, and are used to designate an image to be differentially processed by its image number.

When the operator presses one of the buttons 41, the LED inside that button is turned on, and with this operation, a required detector array can be assigned to each image.

When a plurality of detector arrays are selected for a single image, acquired data from these detector arrays are bundled to form a single image (image bundling).

On the other hand, when the operator presses one of the buttons 42, the LED inside that button is turned on, and with this operation, an image to be differentially processed can be designated.

Figure 30:
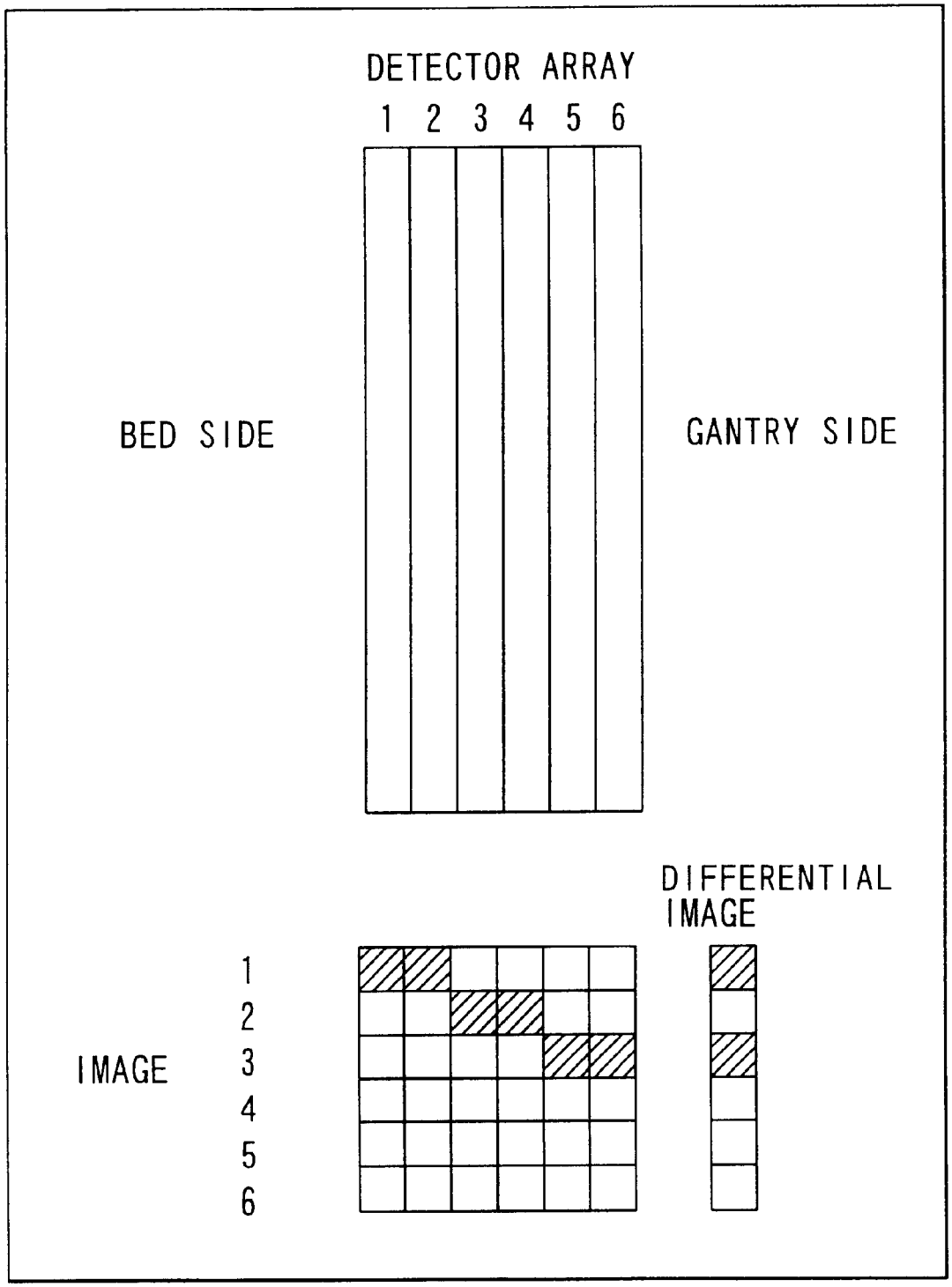
FIG. 30 is a view showing an example of designation by the input device according to the fourth embodiment.

FIG. 30 shows an example of designation by this input device 6.

ON buttons (indicated by hatching) mean that those buttons have been pressed by the operator. Note that the aforementioned conditions are designated by the buttons but such designation may be implemented by a display and touch panel, or a mouse cursor which is moved to a predetermined location on the display screen and is clicked may be used in place of the touch panel.

A signal that represents depression information of the buttons on the first input device is sent to the main controller 30. The main controller 30 operates as follows based on this depression information.

Figure 31:
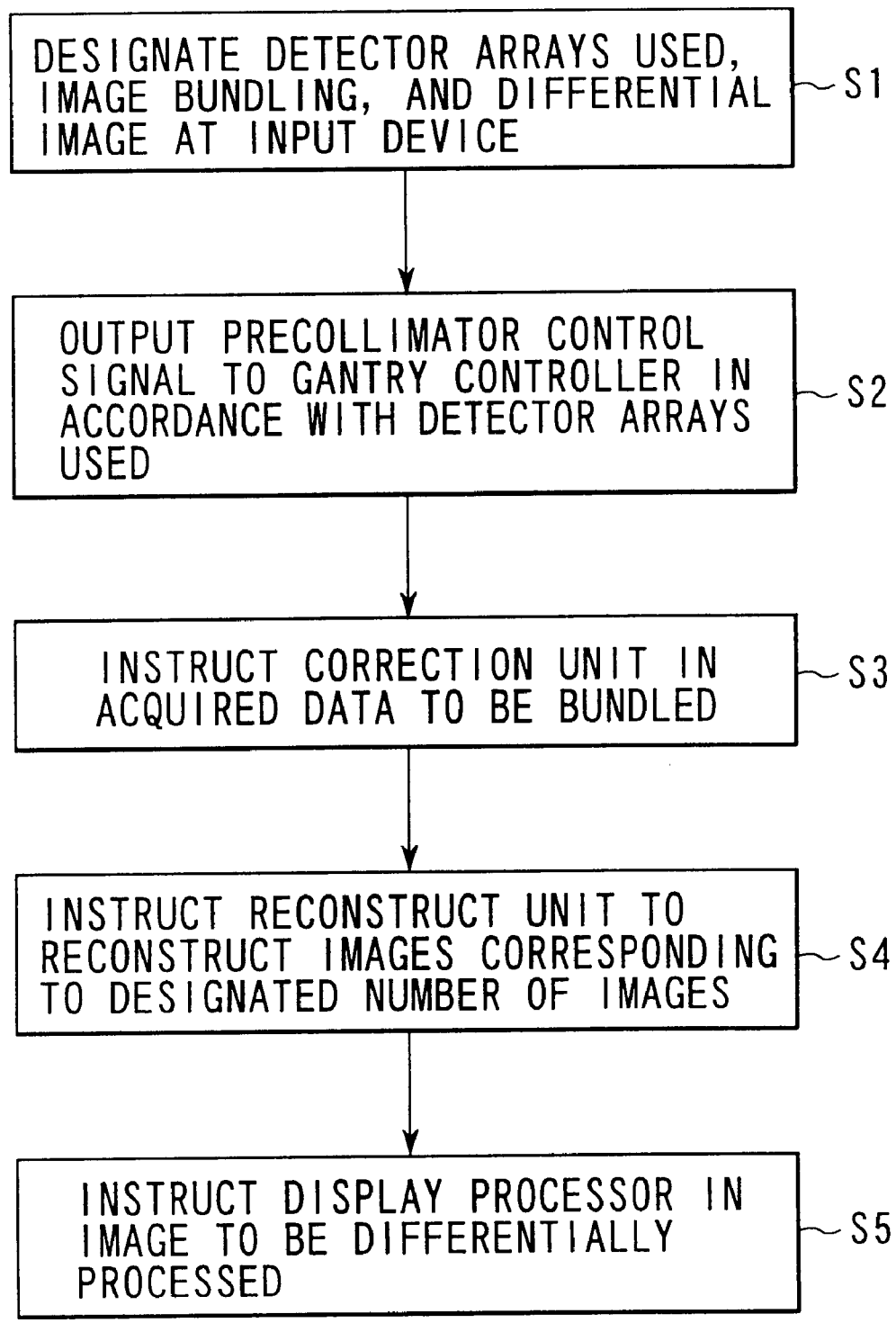
FIG. 31 is a flow chart showing the operation of a main controller 30 according to the fourth embodiment.

FIG. 31 is a flow chart showing the operation of the main controller 30. This flow chart includes decision processes and the like implemented by the main controller 30 upon receiving the designation information from the input device 6.

In step S1, the operator designates the detector arrays used, image bundling, and an image to be differentially processed using the input device 6. In step S2, a precollimator control signal is output to the gantry controller 33 in accordance with the detector arrays used. In step S3, the main controller instructs the correction unit 34 in acquired data to be bundled. Subsequently, in step S4 the main controller instructs the reconstruction unit 36 to reconstruct images corresponding to the number of designated images. Then, the main controller instructs the display processor 37 in an image to be differentially processed.

[Precollimator Aperture Control]

Figure 32:
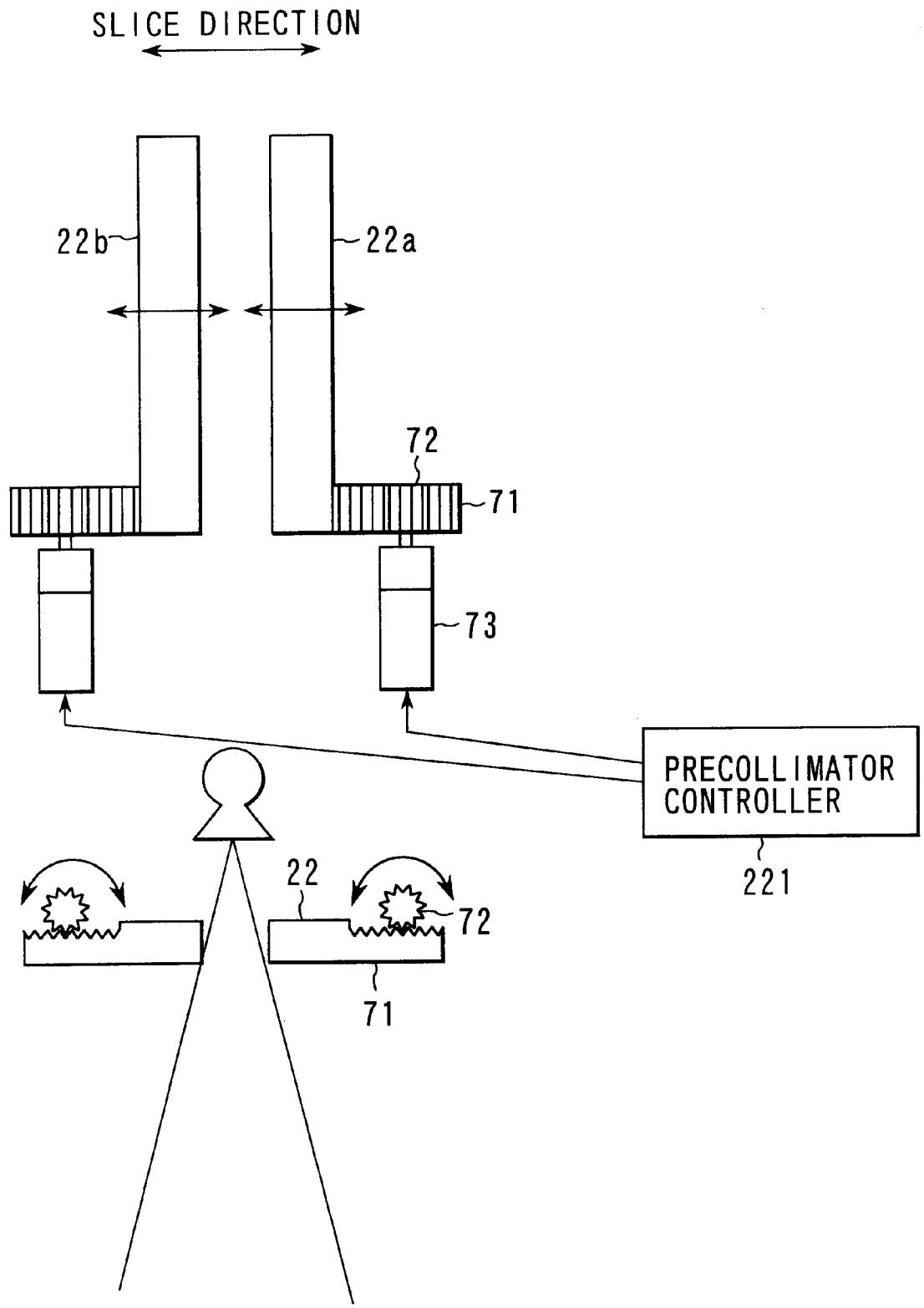
FIG. 32 is a view showing a mechanism for controlling the aperture width of a precollimator according to the fourth embodiment.

FIG. 32 is a view showing a mechanism for controlling the aperture width of the precollimator.

The precollimator controller 221 independently controls the positions of two blades 22a and 22b of the precollimator 22 in the rotation axis direction. On the other hand, the precollimator 22 outputs pulses indicating the operation positions of the two blades 22a and 22b.

Stepping motors (or servo motors) 73 drive pinion gears 72 to rotate via reduction gear mechanisms in accordance with the output pulses. The rotational forces of the pinion gears 72 are transmitted to rack gears 72 to convert rotations into linear motions, thus controlling the positions of the blades 22a and 22b of the precollimator 22.

The mechanism for controlling the aperture width of the precollimator shown in FIG. 32 is merely an example, and any other methods may be used as long as not only the aperture width but also the precollimator position can be controlled.

[Bundling Operation]

Figure 33A:
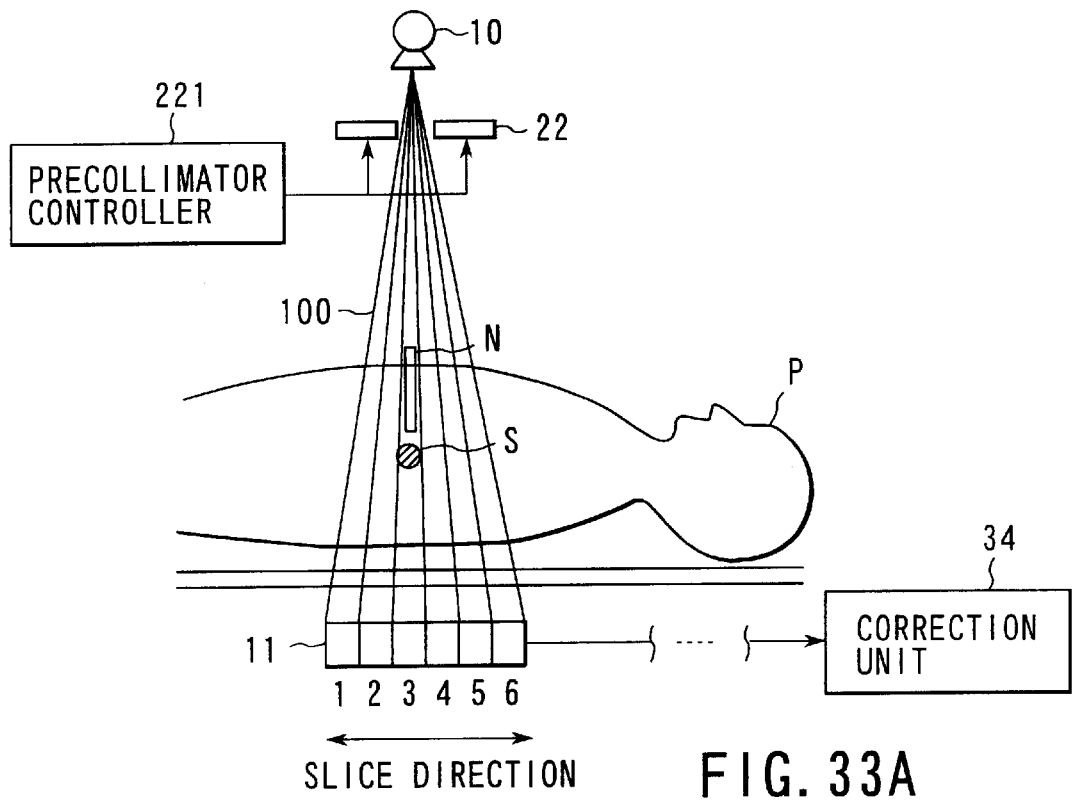
FIG. 33A is a view showing the state of multi-slice CT fluoroscopy according to the fourth embodiment, and X-ray radiation control by the precollimator.

According to the aforementioned setups, the precollimator 22 sets an aperture width corresponding six detector arrays, as shown in FIG. 33A, and multi-slice CT fluoroscopy is started.

Figure 33B:
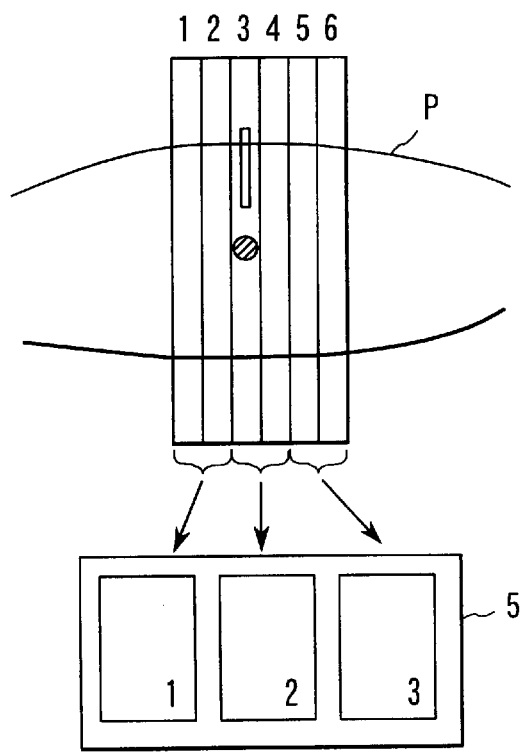
FIG. 33B is a view showing the state of multi-slice CT fluoroscopy according to the fourth embodiment, and a plurality of slices of a patient and their displayed images.

At this time, acquired data for six arrays are directly sent to the correction unit 34, and the data for four central arrays are bundled to obtain acquired data corresponding to three images, as shown in FIG. 33B. Three images are reconstructed within a time shorter than the time required per scan in the designated image direction in accordance with the instruction from the main controller 30, and are sent to the display processor 37.

[Bundling and Reconstruction]

According to the aforementioned setups, the precollimator 22 sets an aperture width corresponding six detector arrays, as shown in FIG. 33A, and multi-slice CT fluoroscopy is started.

At this time, acquired data for six arrays are directly sent to the correction unit 34, and the data from the first and second arrays, third and fourth arrays, and fifth and sixth arrays are respectively bundled to obtain acquired data corresponding to three images, as shown in FIG. 33B. Three images are reconstructed within a time shorter than the time required per scan in accordance with the instruction from the main controller 30, and are sent to the display processor 37.

[Differential Process]

The "differential process" in this embodiment is to generate a differential image by differentially processing a specific image and at least one of a plurality of tomographic images reconstructed by the reconstruction unit 36. In this case, the "specific image" is an image at an identical slice position, which was reconstructed first in image acquisition by the reconstruction unit 36.

[Display on Display]

The display processor 37 displays three reconstructed images on the display 5 in accordance with an instruction from the main controller 30. The display 5 shown in FIG. 33B corresponds to a display example in this case.

[First Display Example in Centesis Procedure: Centesis along Central Image]

FIG. 34 is a view showing the first display example in the centesis procedures using the multi-slice CT fluoroscopy system of this embodiment. This display example includes a series of display examples from when a centesis needle begins to be inserted into the patient until the centesis needle reaches a target. The operator inserts the centesis needle with respect to a target displayed in image 2 not to deviate from the slice width of image 2.

Figure 34A:
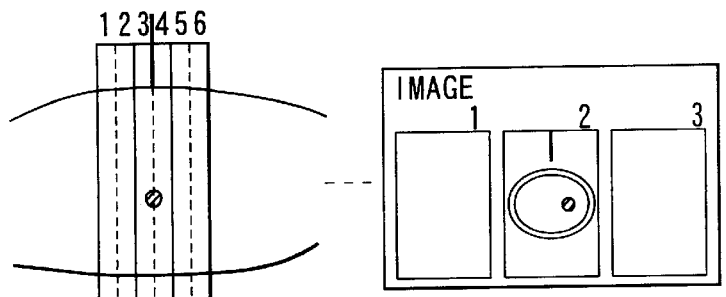
FIG. 34A is a view showing the first display example when a centesis is done using a multi-slice CT fluoroscopy system according to the fourth embodiment.

FIG. 34A shows a state immediately before insertion of the centesis needle. End images (images 1 and 3) of image 2 do not undergo a differential process yet. In this state, the operator confirms if the target and centesis needle fall within image 2.

Figure 34B:
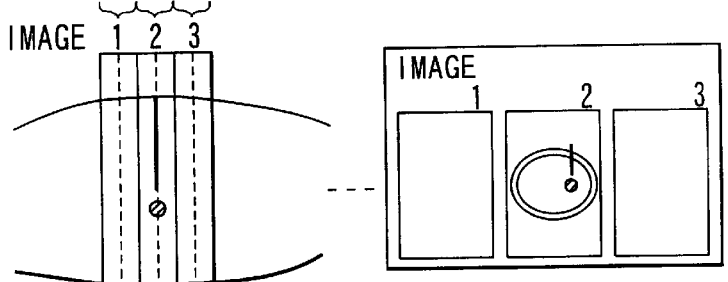
FIG. 34B is a view showing the first display example when a centesis is done using a multi-slice CT fluoroscopy system according to the fourth embodiment.

As shown in FIG. 34B, the operator starts the centesis procedures after he or she switches the display mode of end images of image 2 to differential display. The differential display mode is selected using the aforementioned input device 6.

Figure 34C:
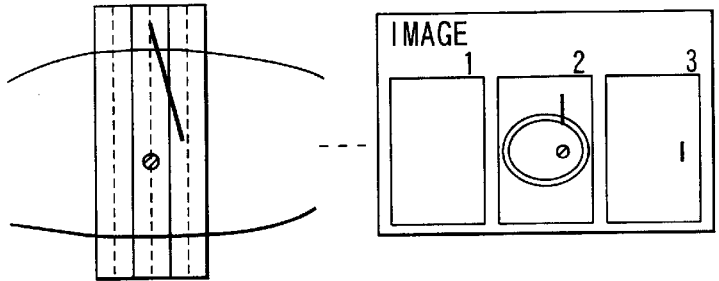
FIG. 34C is a view showing the first display example when a centesis is done using a multi-slice CT fluoroscopy system according to the fourth embodiment.

FIG. 34C shows a state wherein the distal end of the centesis needle has deviated toward image 3 side. In this state, image 3 (and image 1) has been switched to the differential display mode.

When an image reconstructed by the reconstruction unit 36 and the first image of image acquisition undergo the differential process, since no centesis needle appears in the first image, the generated differentially processed image (i.e., image 3) clearly shows only the centesis needle.

Therefore, the centesis operator can clearly confirm deviation of the insertion direction of the centesis needle in the direction of image 3 by observing image 3, and can appropriately correct the direction.

Figure 34D:
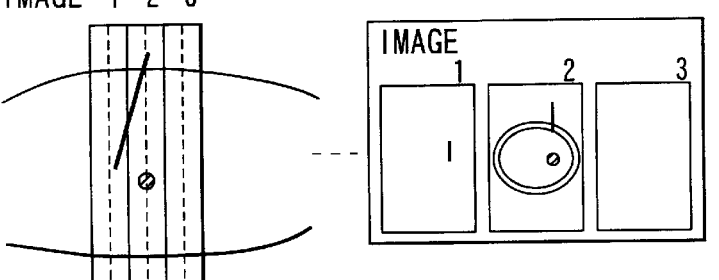
FIG. 34D is a view showing the first display example when a centesis is done using a multi-slice CT fluoroscopy system according to the fourth embodiment.

On the other hand, FIG. 34D shows a state wherein the distal end of the centesis needle has deviated toward image 1 side. In this state, image 1 has been switched to the differential display mode as in image 3. The generated differentially processed image (in this case, image 1) clearly shows only the centesis needle as in image 3. For this reason, the centesis operator can clearly recognize deviation of the insertion direction of the centesis needle in the direction of image 1 by observing image 1, and can appropriately correct the direction.

Figure 34E:
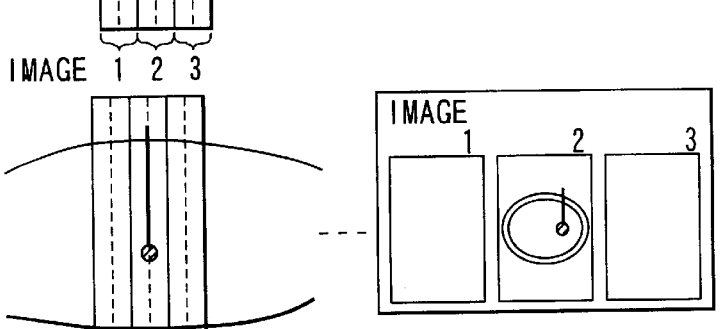
FIG. 34E is a view showing the first display example when a centesis is done using a multi-slice CT fluoroscopy system according to the fourth embodiment.

As described above, when the insertion direction of the centesis needle has deviated, as shown in FIG. 34C or 34D, the centesis operator can clearly recognize deviation of the insertion direction of the centesis needle on the basis of the differential image, and can appropriately correct that direction. Hence, the centesis needle can reliably reach a target such as a tumor or the like, as shown in FIG. 34E.

[Second Display Example in Centesis Procedure: Oblique Centesis]

FIG. 35 is a view showing the second display example in the centesis procedures using the multi-slice CT fluoroscopy system of this embodiment. This display example exemplifies a case wherein the centesis needle is obliquely inserted into the patient to avoid ribs or the like. The operator inserts the centesis needle with respect to a target displayed in image 3 via positions displayed in images 1 and 2.

Figure 35A:
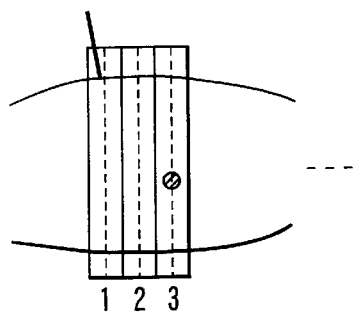
FIG. 35A is a view showing the second display example when a centesis is done using a multi-slice CT fluoroscopy system according to the fourth embodiment.
Figure 35A:
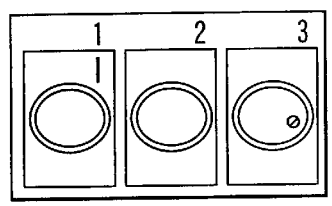

FIG. 35A shows a state immediately before insertion of the centesis needle. In this state, the operator confirms if the distal end of the centesis needle falls within image 1, and if the target falls within image 3.

Figure 35B:
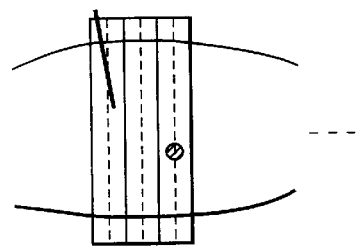
FIG. 35B is a view showing the second display example when a centesis is done using a multi-slice CT fluoroscopy system according to the fourth embodiment.
Figure 35B:
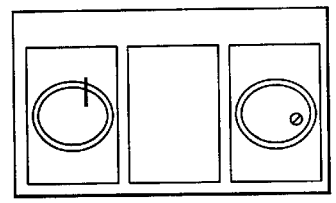

In order to clearly find that the distal end of the centesis needle has reached image 2, the operator begins the centesis procedures after he or she switches image 2 to the differential display mode (FIG. 35B). Note that image 3 does not undergo any differential display since it must display the target.

Figure 35C:
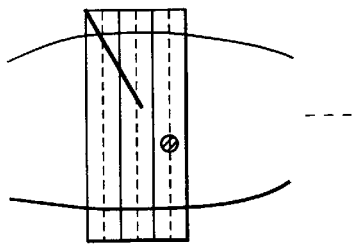
FIG. 35C is a view showing the second display example when a centesis is done using a multi-slice CT fluoroscopy system according to the fourth embodiment.
Figure 35C:
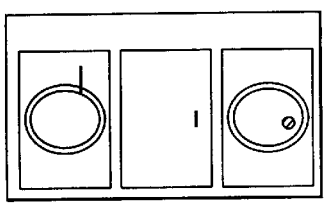

As shown in FIG. 35C, the operator can find that the distal end of the centesis needle has reached the position of image 2 by observing image 2 displayed in the differential display mode.

Figure 35D:
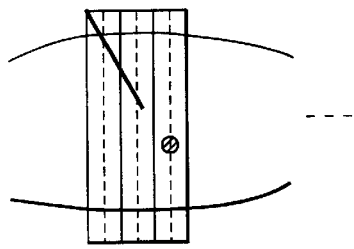
FIG. 35D is a view showing the second display example when a centesis is done using a multi-slice CT fluoroscopy system according to the fourth embodiment.
Figure 35D:
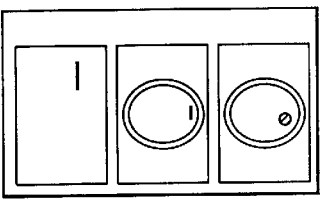

The operator then cancels the differential display mode of image 2 by operating input device 6 to observe image 2 in detail (FIG. 35D). Note that image 1 is switched to the differential display mode to confirm if the centesis needle returns again.

Figure 35E:
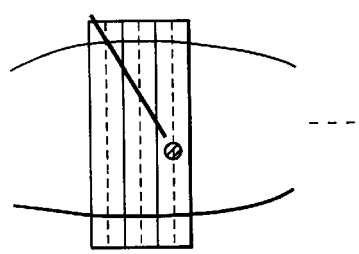
FIG. 35E is a view showing the second display example when a centesis is done using a multi-slice CT fluoroscopy system according to the fourth embodiment.
Figure 35E:
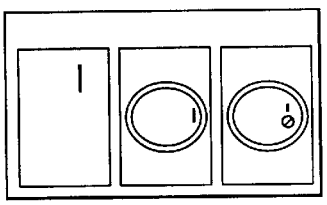

As shown in FIG. 35E, the operator finds that the distal end of the centesis needle has reached the position of image 3 by observing image 3 displayed in the differential display mode.

Figure 35F:
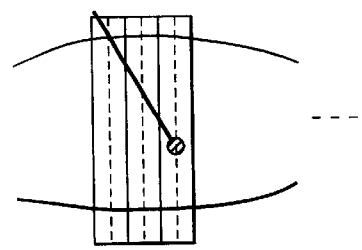
FIG. 35F is a view showing the second display example when a centesis is done using a multi-slice CT fluoroscopy system according to the fourth embodiment.
Figure 35F:
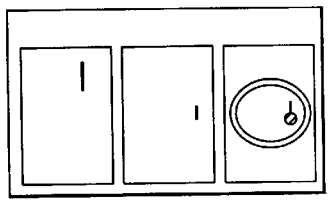

As described above, when the operator obliquely inserts the centesis needle into the patient to avoid ribs or the like, he or she can insert the centesis needle while clearly grasping the distal end of the needle by switching images located along the insertion route of the centesis needle to the differential display mode as needed. Therefore, the centesis needle can reliably reach a target such as a tumor or the like, as shown in FIG. 35F.

As described above, according to the fourth embodiment, the operator can proceed while clearly recognizing the position of an insertion such as a centesis needle in the centesis procedures on the basis of the differentially displayed reconstructed image. In this manner, any danger (e.g., a centesis needle pierces a wrong organ of the patient) can be easily avoided, and high-precision centesis procedures can be quickly done. Hence, the dose on the patient can be minimized.

Modifications of the fourth embodiment will be described below.

[Image to be Differentially Processed]

In the above embodiment, a difference from an image at an identical slice position, which was reconstructed first in image acquisition is computed. Alternatively, a difference from an immediately preceding image or an image reconstructed a predetermined period of time ago may be computed. As a result, influences resulting from peristalsis or shifts or the like of organs due to insertion of the centesis needle can be prevented from appearing in the differential image, and the differential image can be observed more easily.

[Alert Display]

Figure 36A:
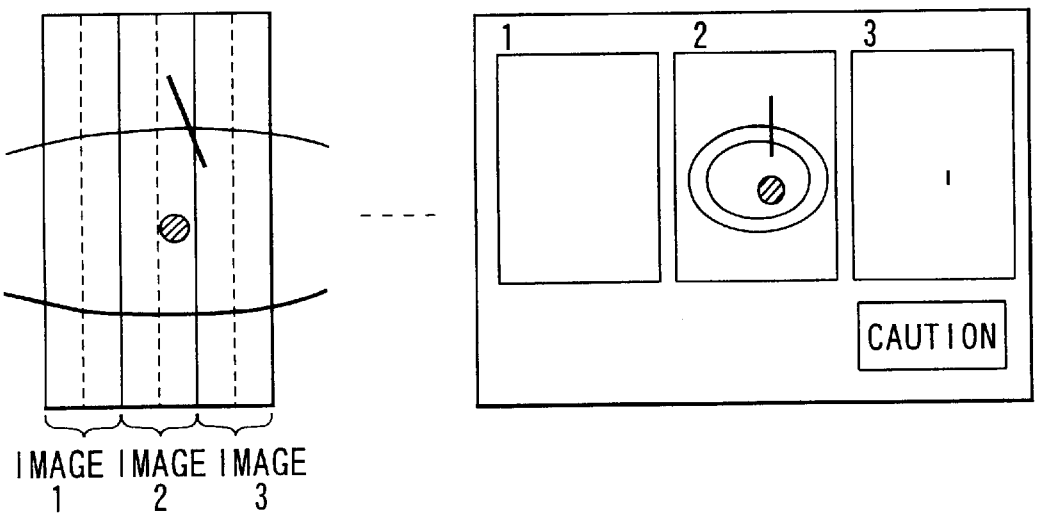
FIG. 36A is a view showing an example of alert display in the fourth embodiment.
Figure 36B:
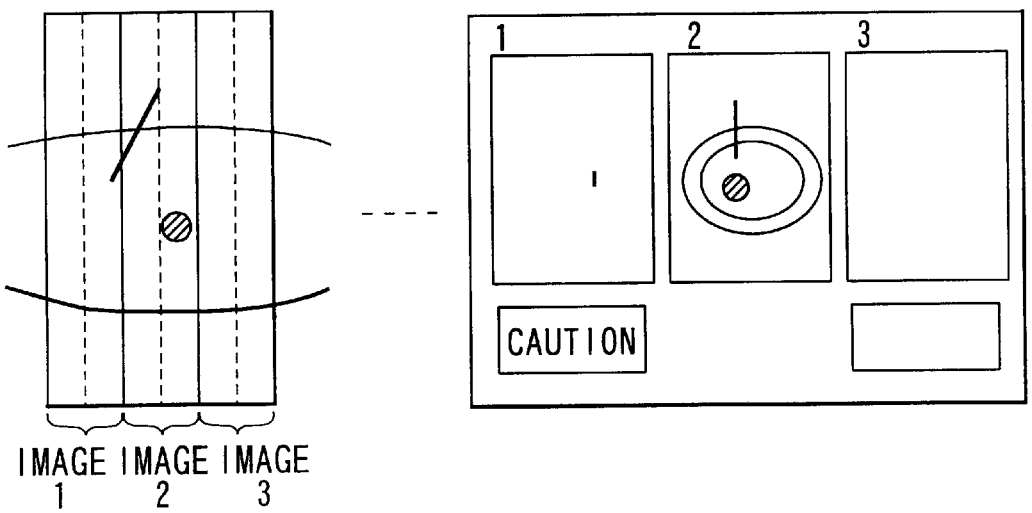
FIG. 36B is a view showing another example of alert display in the fourth embodiment.

When the differential value for an image designated in the differential display mode has exceeded a predetermined threshold value, an alert message ("caution" in an example in FIG. 36) may be displayed, as shown in FIG. 36. FIG. 36A shows a case wherein when the centesis needle has reached image 3, and the differential value of image 3 has exceeded a threshold value, a message is displayed below image 3, and FIG. 36B shows a case wherein when the centesis needle has reached image 1, and the differential value of image 1 has exceeded a threshold value, a message is displayed below image 1.

By positively informing the observer that the threshold value has been exceeded, for example, the observer can more reliably recognize entrance of an insertion such as a centesis needle or the like to a neighboring image.

The alert is not limited to such specific character display. For example, the background color of an image may be changed, the background of the screen may be flickered, or alert sound may be produced.

Furthermore, different alerts may be generated in units of images designated in the differential display mode. For example, when the background color of the screen is changed, different colors are assigned in units of differential images. On the other hand, when an alert is produced by means of sound, different sounds are assigned in units of differential images.

In this manner, since insertion of the centesis needle can be easily recognized not only by image display but also by other means, it can be efficiently done.

(Fifth Embodiment)

The fifth embodiment relates to multi-slice CT fluoroscopy that displays a threshold-processed image.

In a system of this embodiment, the number of images to be displayed corresponding to slice positions, and the slice thickness of each image can be arbitrarily set. In this system, data from the first and second arrays of the detector arrays are bundled to obtain a single image, data from the third and fourth arrays are bundled to obtain a single image, and data from the fifth and sixth arrays are bundled to obtain a single image, thus practicing a fluoroscopy mode of a total of three images.

[Input Device]

Figure 37:
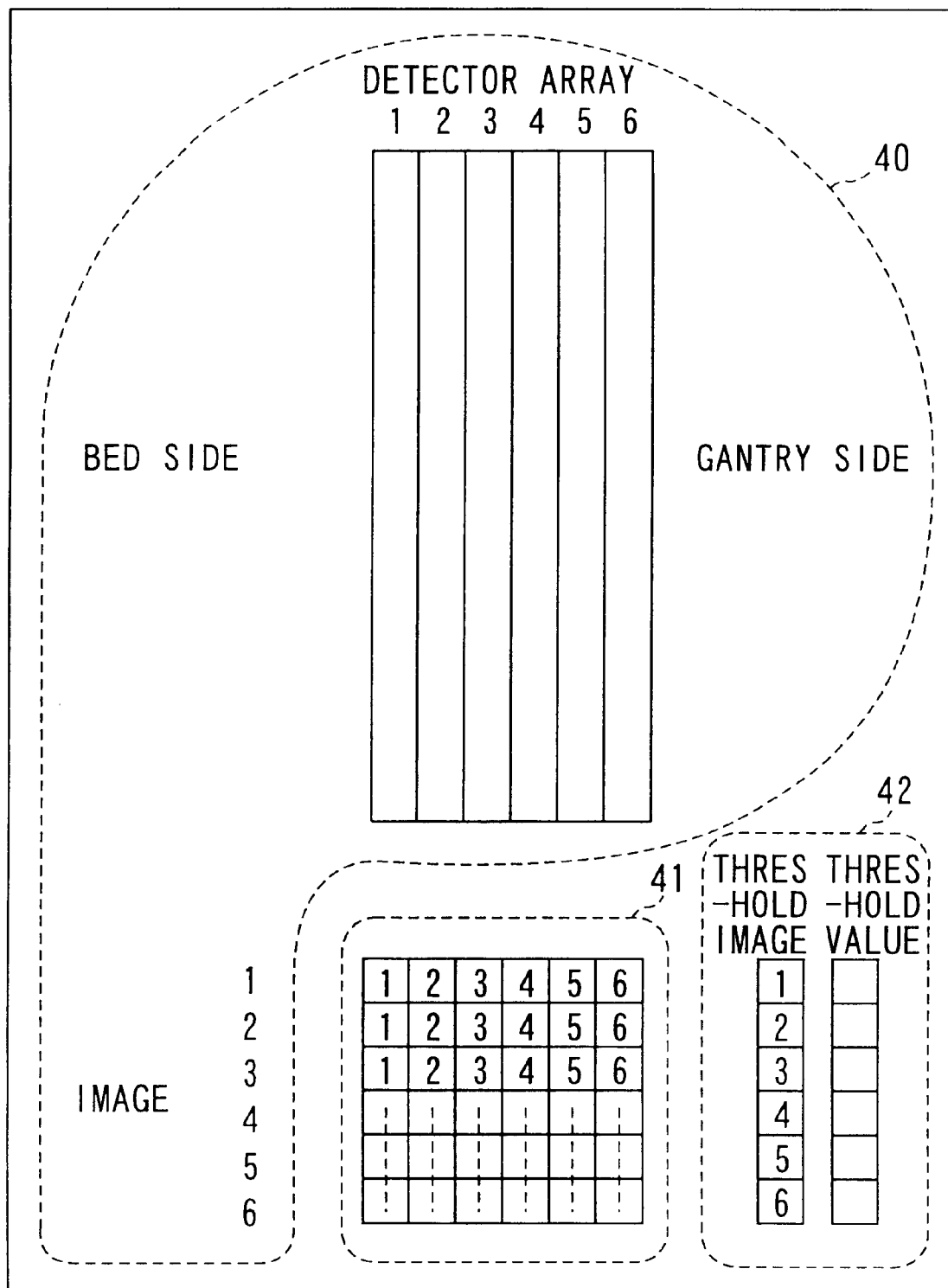
FIG. 37 is a view showing an input device according to the fifth embodiment.

FIG. 37 is a view showing an input device of this embodiment. This input device is a means for designating detector arrays to be used, image bundling, and threshold-processed images, and is provided in the input device 6. Note that the input device 6 is provided to the gantry 1 or bed 2, or on the control cabinet 3, as shown in FIG. 1.

Referring to FIG. 37, reference numeral 40 denotes icons (iconic symbols) indicating the numbers of detector arrays, the gantry side and bed side, and the numbers of images; 41, a plurality of buttons which include LEDs, and make the number of detector arrays correspond to those of images; and 42, a plurality of buttons which include LEDs like in the buttons 41, and are used to designate an image to be subjected to a threshold process by its image number, and a dial for setting a threshold value in units of threshold-processed images.

When the operator presses one of the buttons 41, the LED inside that button is turned on, and with this operation, a required detector array can be assigned to each image.

When a plurality of detector arrays are selected for a single image, acquired data from these detector arrays are bundled to form a single image (image bundling).

On the other hand, when the operator presses one of the buttons 42, the LED inside that button is turned on, and with this operation, an image to be differentially processed can be designated. Also, by operating the dial, a threshold value can be designated by a numerical value.

Figure 38:
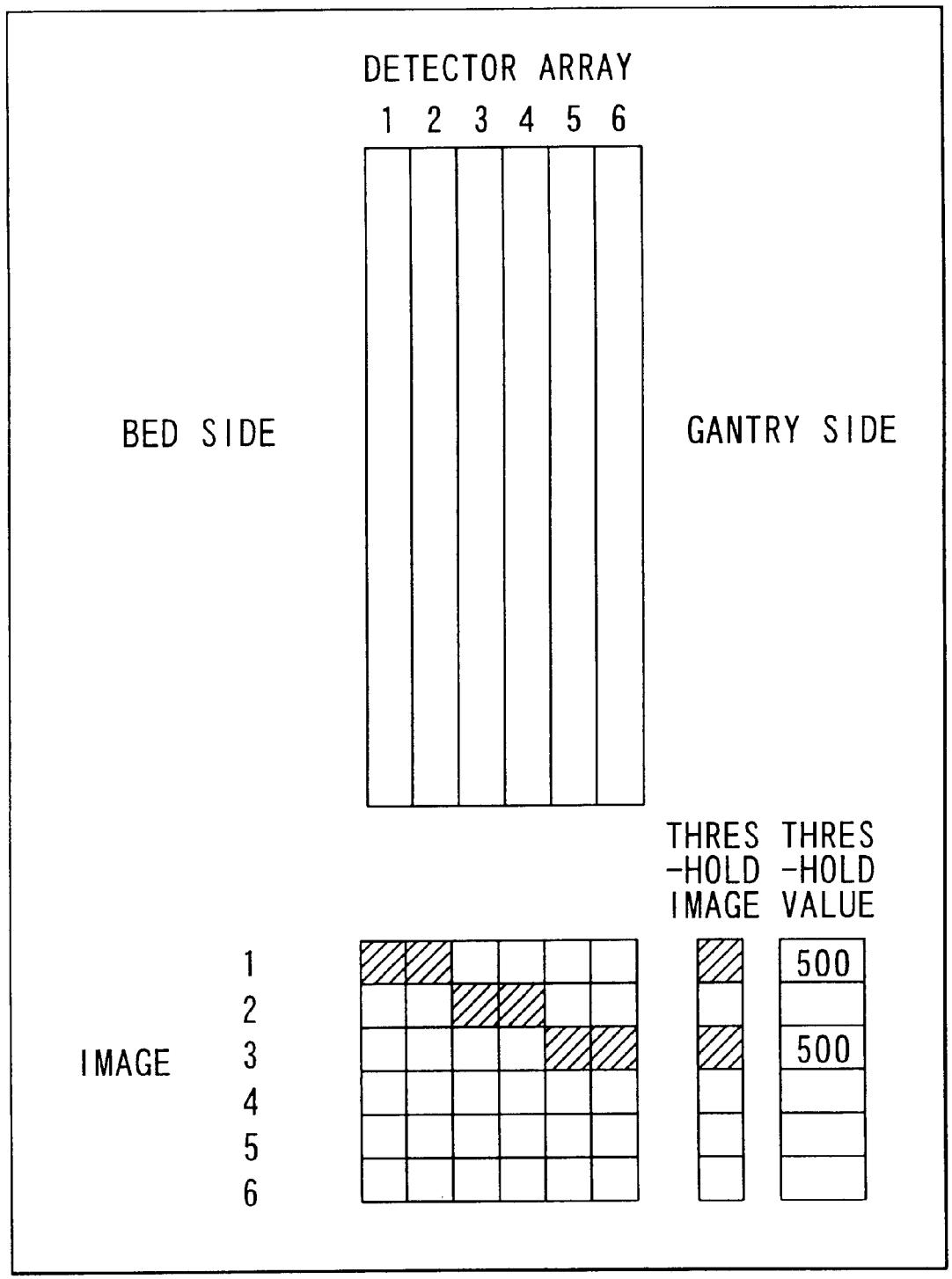
FIG. 38 is a view showing an example of designation by the input device according to the fifth embodiment.

FIG. 38 shows an example of designation by this input device 6.

ON buttons (indicated by hatching) mean that those buttons have been pressed by the operator. Note that the aforementioned conditions are designated by the buttons but such designation may be implemented by a display and touch panel, or a mouse cursor which is moved to a predetermined location on the display screen and is clicked may be used in place of the touch panel.

A signal that represents depression information of the buttons on the first input device is sent to the main controller 30. The main controller 30 operates as follows based on this depression information.

Figure 39:
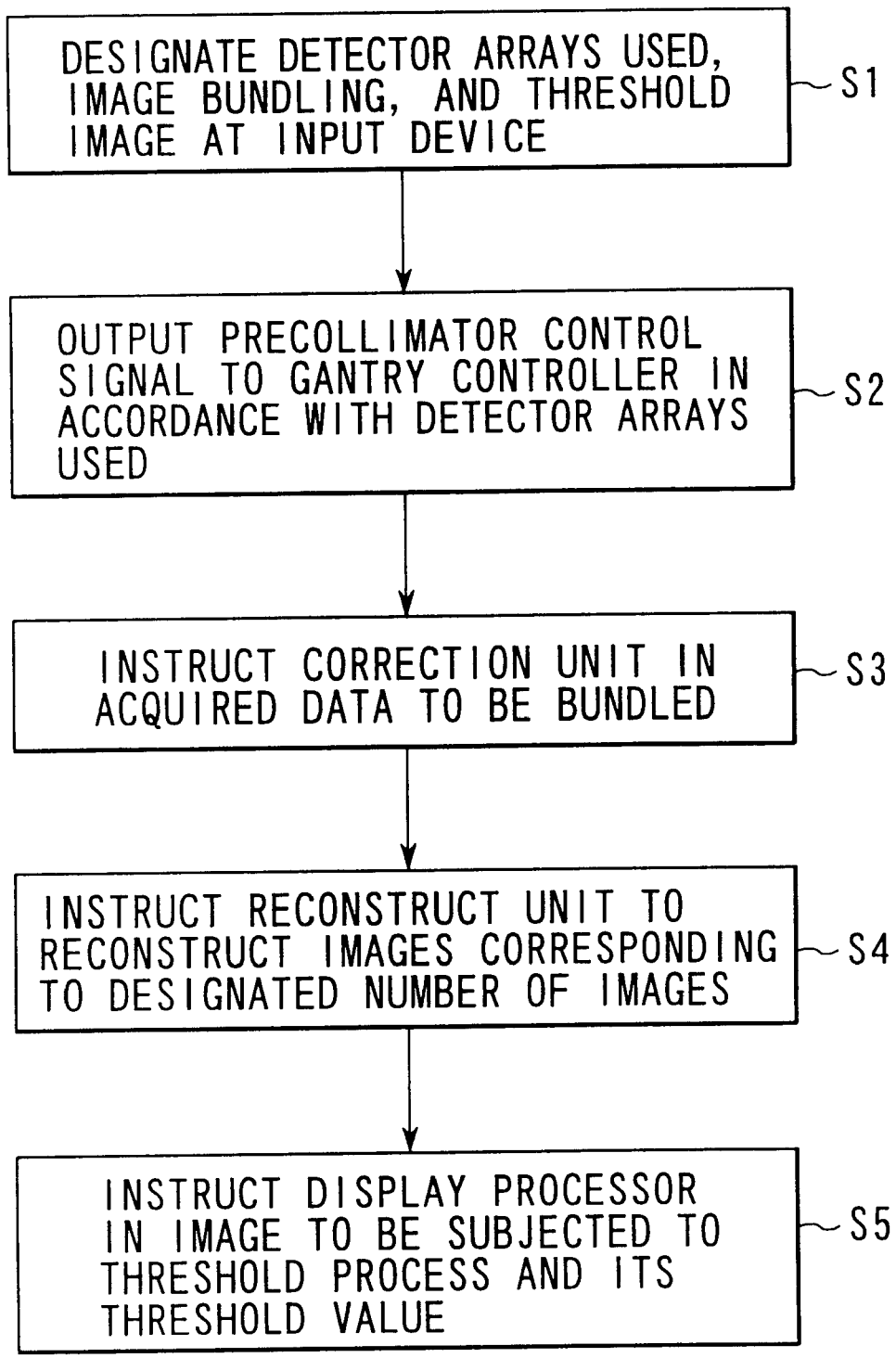
FIG. 39 is a flow chart showing the operation of a main controller according to the fifth embodiment.

FIG. 39 is a flow chart showing the operation of the main controller 30. This flow chart includes decision processes and the like implemented by the main controller 30 upon receiving the designation information from the input device 6.

In step S1, the operator designates the detector arrays used, image bundling, and an image to be differentially processed using the input device 6. In step S2, a precollimator control signal is output to the gantry controller 33 in accordance with the detector arrays used. In step S3, the main controller instructs the correction unit 34 in acquired data to be bundled. Subsequently, in step S4 the main controller instructs the reconstruction unit 36 to reconstruct images corresponding to the number of designated images. Then, the main controller instructs the display processor 37 in an image to be subjected to a threshold process.

[Threshold Process]

The "threshold process" in this embodiment compares the pixel values of at least one of a plurality of tomographic images reconstructed by the reconstruction unit 36 with a predetermined threshold value, and generates an image defined by only pixels that have exceeded the threshold value. The threshold value is a specific pixel value (e.g., a CT value) that can distinguish the patient and the insertion (centesis needle in this case) into the patient, and for example, a CT value=500 is set as the threshold value in this embodiment.

[Display on Display]

The display processor 37 displays three reconstructed images on the display 5 in accordance with an instruction from the main controller 30. The display example in this case is the same as that shown in FIG. 34 in the fourth embodiment, and images 1 and 3 correspond to threshold-processed images. In each threshold-processed image, only portions with CT values equal to or higher than 500 are displayed. For this reason, only the centesis needle having a CT value equal to or higher than 500 is displayed.

According to the fifth embodiment, the centesis needle with a high CT value is extracted by the threshold process and is displayed. That is, the same image as that obtained by the differential process in the fourth embodiment can be obtained. Hence, the same effect as in the fourth embodiment described above can be obtained.

Modifications of the fifth embodiment will be described below.

[Alert Display]

In the fifth embodiment, the alert display may be made as in the fourth embodiment.

[Coloring of Excess of Threshold Value]

In the fifth embodiment described above, a threshold-processed image consisting of pixel values that have exceeded the threshold value is obtained. Alternatively, the following image may be obtained.

That is, pixels that have exceeded the threshold value may be colored in specific color to obtain an image consisting of these colored pixels and pixels which do not exceed the threshold value. With this image, so-called highlight display is made.

Figure 40A:
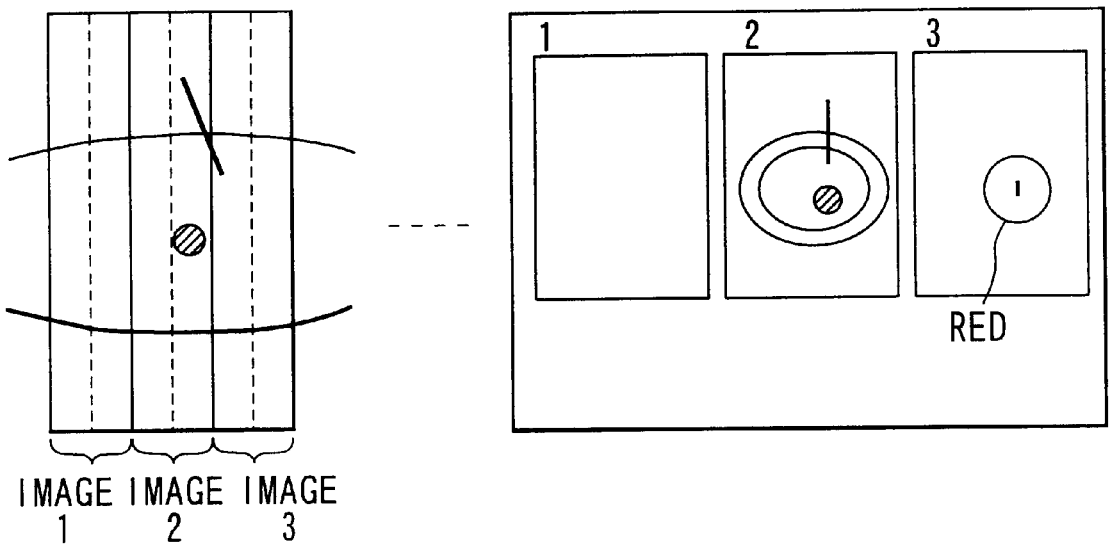
FIG. 40A is a view showing an example of highlight display according to the fifth embodiment.
Figure 40B:
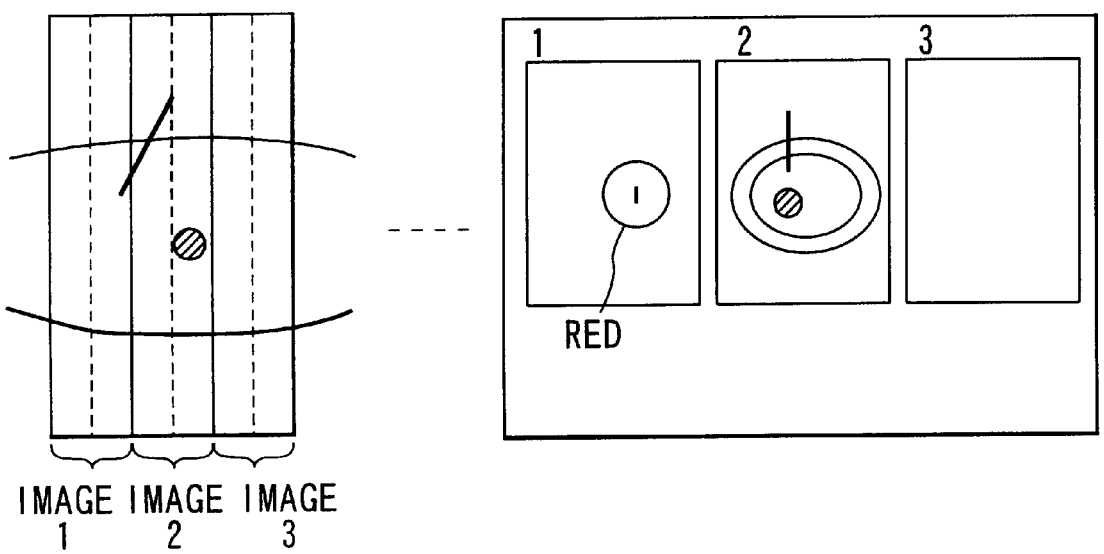
FIG. 40B is a view showing another example of highlight display according to the fifth embodiment.

FIG. 40 is a view showing an example of such highlight display. In this display example, the threshold value is set for two end images (images 1 and 3). In images 1 and 3, the centesis needle that has exceeded the threshold value is displayed in, e.g., red.

According to this arrangement, the image itself around the target can be observed, and the direction in which the centesis needle has deviated can be clearly recognized. Even when untouchable portions are present around the target (images 1 and 3 in this case), the centesis needle can be safely inserted.

Note that only images 1 and 3 may undergo such process. As a result, since an insertion such as a centesis needle or the like is always highlighted, the position of the centesis needle can be recognized more easily.

Various modifications associated with the first and fifth embodiments will be explained below.

[Superposed Display]

In the above embodiments, a plurality of images are displayed in a line. However, the present invention is not limited to such specific image display method. Three images having different slice positions may be generated in correspondence with R, G, and B, and may be superposed to display a single image.

Figure 41A:
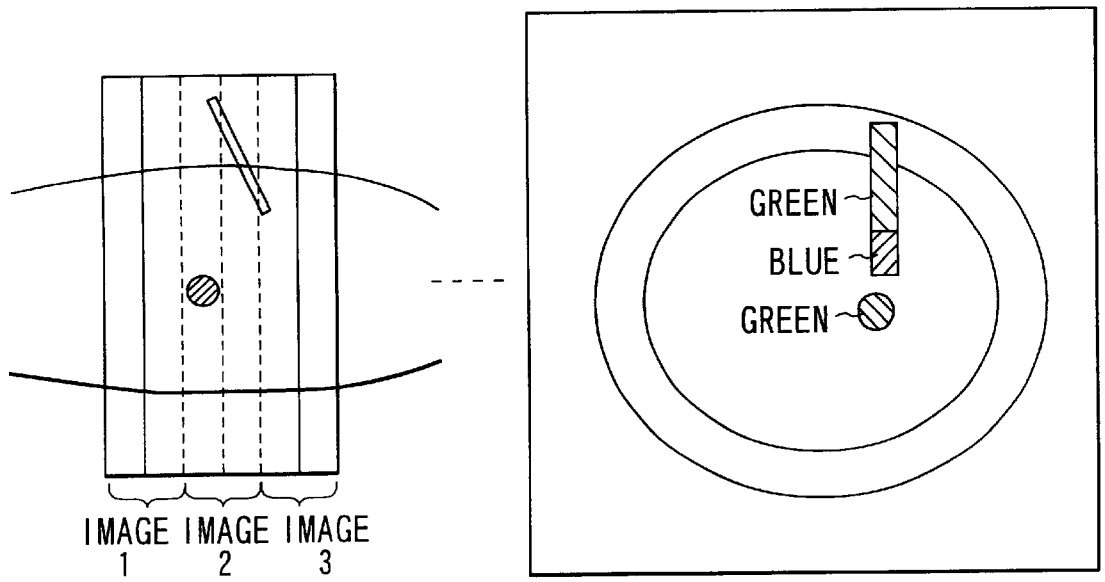
FIG. 41A is a view showing an example of RGB superposed display according to the fifth embodiment.
Figure 41B:
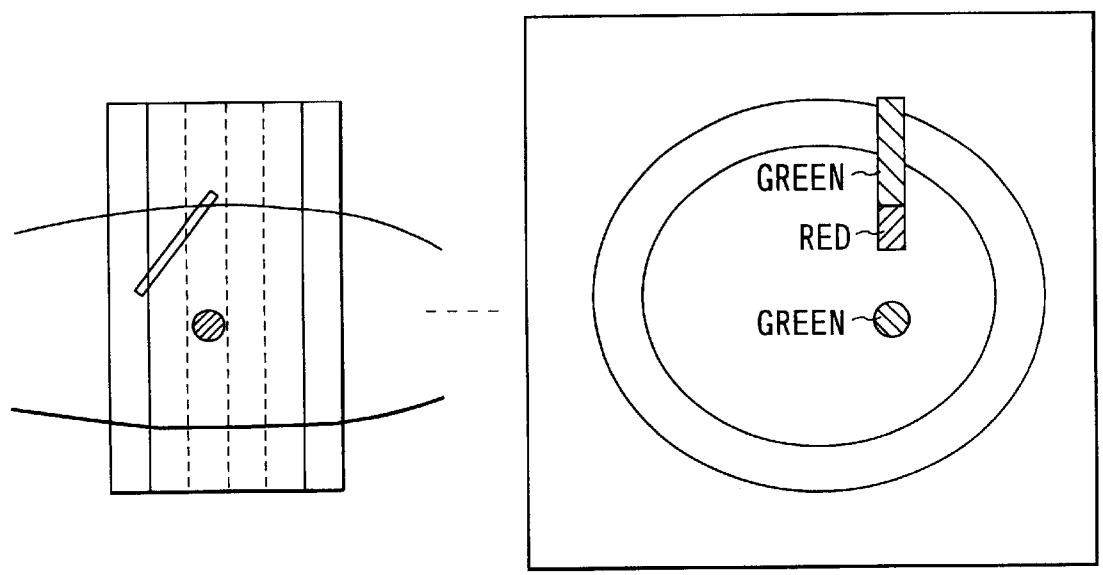
FIG. 41B is a view showing another example of RGB superposed display according to the fifth embodiment.

FIG. 41 is a view showing an example of such RGB superposed display.

Assume that image 1 is an R (red) image, image 2 a G (green) image, and image 3 a B (blue) image, and these images are set in correspondence with CT values by:

Image 1: CT value=MIN→MAX: RED=0→255

Image 2: CT value=MIN→MAX: GREEN=0→255

Image 3: CT value=MIN→MAX: BLUE=0→255      (1)

The image of interest is displayed in green. Note that MIN and MAX correspond to the window width of a CT value to be displayed, and can be arbitrarily set by the observer. As a result, the images are expressed by:

RED=CT value (image 1)

GREEN=CT value (image 2)

BLUE=CT value (image 3)      (2)

For example, when a needle deviates to a slice position corresponding to image 1 or 3, the color of the needle displayed changes to red or blue. That is, the operator can detect deviation of the needle on the basis of the change in color of the needle on the image.

In this case, three images are taken as an example, but the number of images is not limited to three. The present invention can be applied two images or four or more images. In this manner, since the observer need only observe only one image, and the position of the insertion (needle) can be clearly indicated by color, the insertion can be observed more easily.

(Sixth Embodiment)

The sixth embodiment relates to enlarged display of the image of interest in multi-slice CT fluoroscopy of a total of three images. That is, a multi-slice CT fluoroscopy of this embodiment displays at least one of a plurality of tomographic images reconstructed by the reconstruction unit in an enlarged scale compared to other images. In this case, the system of this embodiment displays an image whose slice position is nearly the center in an enlarged scale, and also detects the position of an insertion inserted into the patient and displays an image corresponding to the detected position in an enlarged scale.

As in the first and fifth embodiments described above, the multi-slice CT fluoroscopy system of this embodiment can arbitrarily set the number of images to be displayed corresponding to slice positions, and the slice thickness of each image. In this system, data from the first and second arrays of the detector arrays are bundled to obtain a single image, data from the third and fourth arrays are bundled to obtain a single image, and data from the fifth and sixth arrays are bundled to obtain a single image, thus practicing a fluoroscopy mode of a total of three images.

[Input Device]

Figure 42:
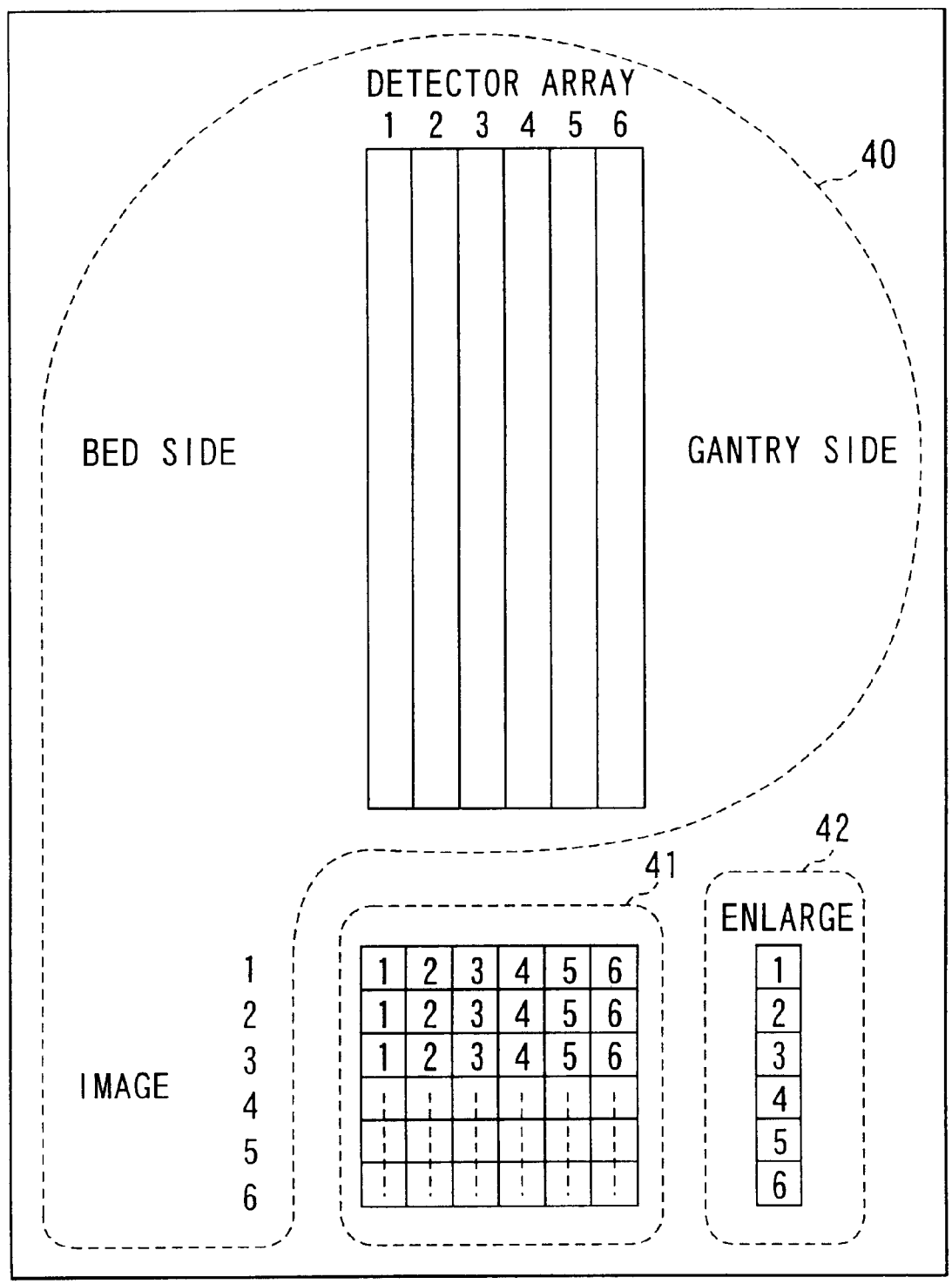
FIG. 42 is a view showing an input device according to the sixth embodiment.

FIG. 42 is a view showing the input device of this embodiment. This input device is a means for designating detector arrays to be used, image bundling, and an image to be displayed in an enlarged scale, and is provided in the input device 6. Note that the input device 6 is provided to the gantry 1 or bed 2, or on the control cabinet 3, as shown in FIG. 1.

Referring to FIG. 42, reference numeral 40 denotes icons (iconic symbols) indicating the numbers of detector arrays, the gantry side and bed side, and the numbers of images; 41, a plurality of buttons which include LEDs, and make the number of detector arrays correspond to those of images; and 42, a plurality of buttons which include LEDs like in the buttons 41, and are used to designate an image to be displayed in an enlarged scale by its image number.

When the operator presses one of the buttons 41, the LED inside that button is turned on, and with this operation, a required detector array can be assigned to each image.

When a plurality of detector arrays are selected for a single image, acquired data from these detector arrays are bundled to form a single image (image bundling).

On the other hand, when the operator presses one of the buttons 42, the LED inside that button is turned on, and with this operation, an image to be displayed in an enlarged scale can be designated.

Figure 43:
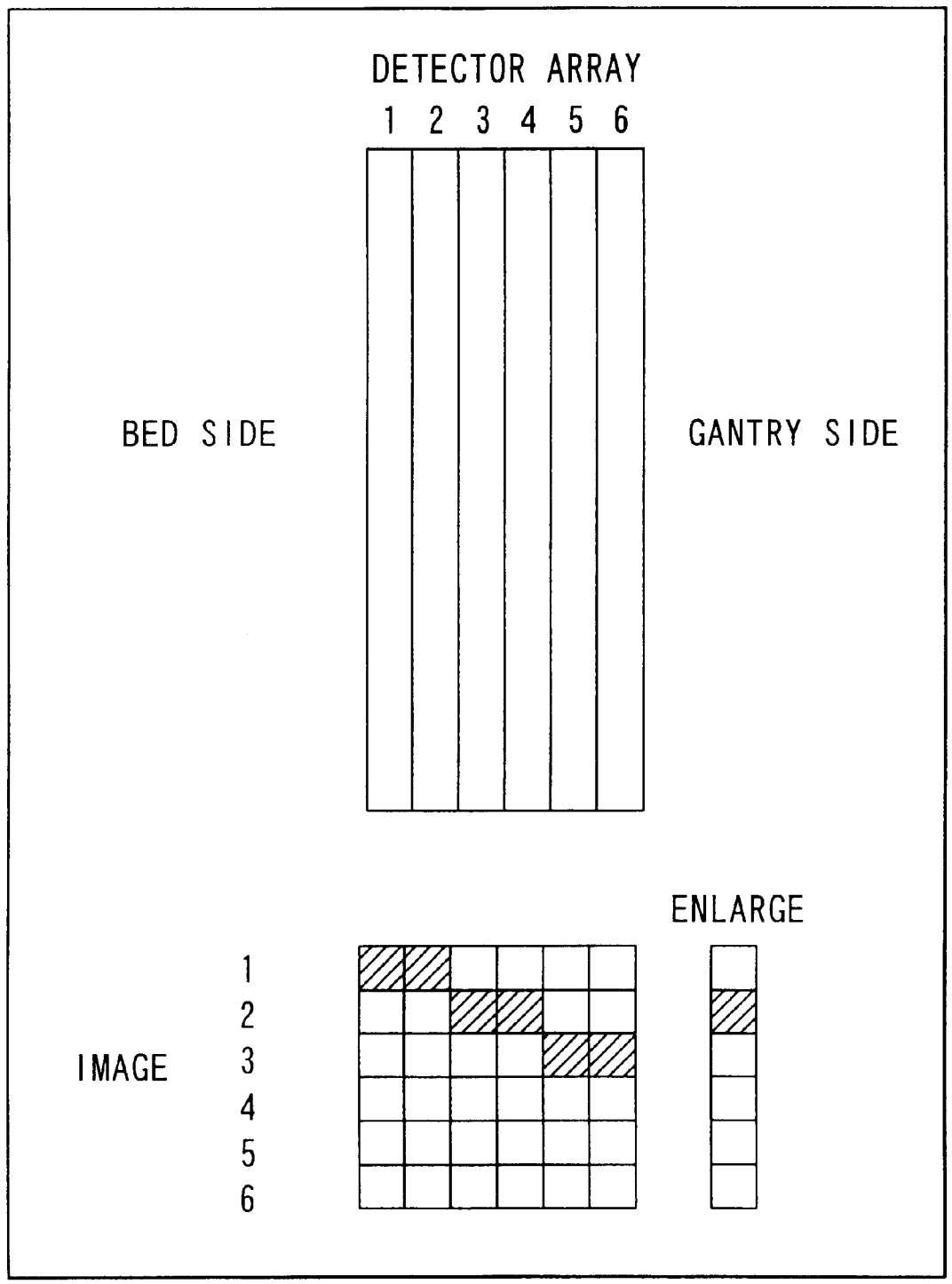
FIG. 43 is a view showing an example of designation by the input device according to the sixth embodiment.

FIG. 43 shows an example of designation by this input device 6.

ON buttons (indicated by hatching) mean that those buttons have been pressed by the operator. Note that the aforementioned conditions are designated by the buttons but such designation may be implemented by a display and touch panel, or a mouse cursor which is moved to a predetermined location on the display screen and is clicked may be used in place of the touch panel.

A signal that represents depression information of the buttons on the first input device is sent to the main controller 30. The main controller 30 operates as follows based on this depression information.

Figure 44:
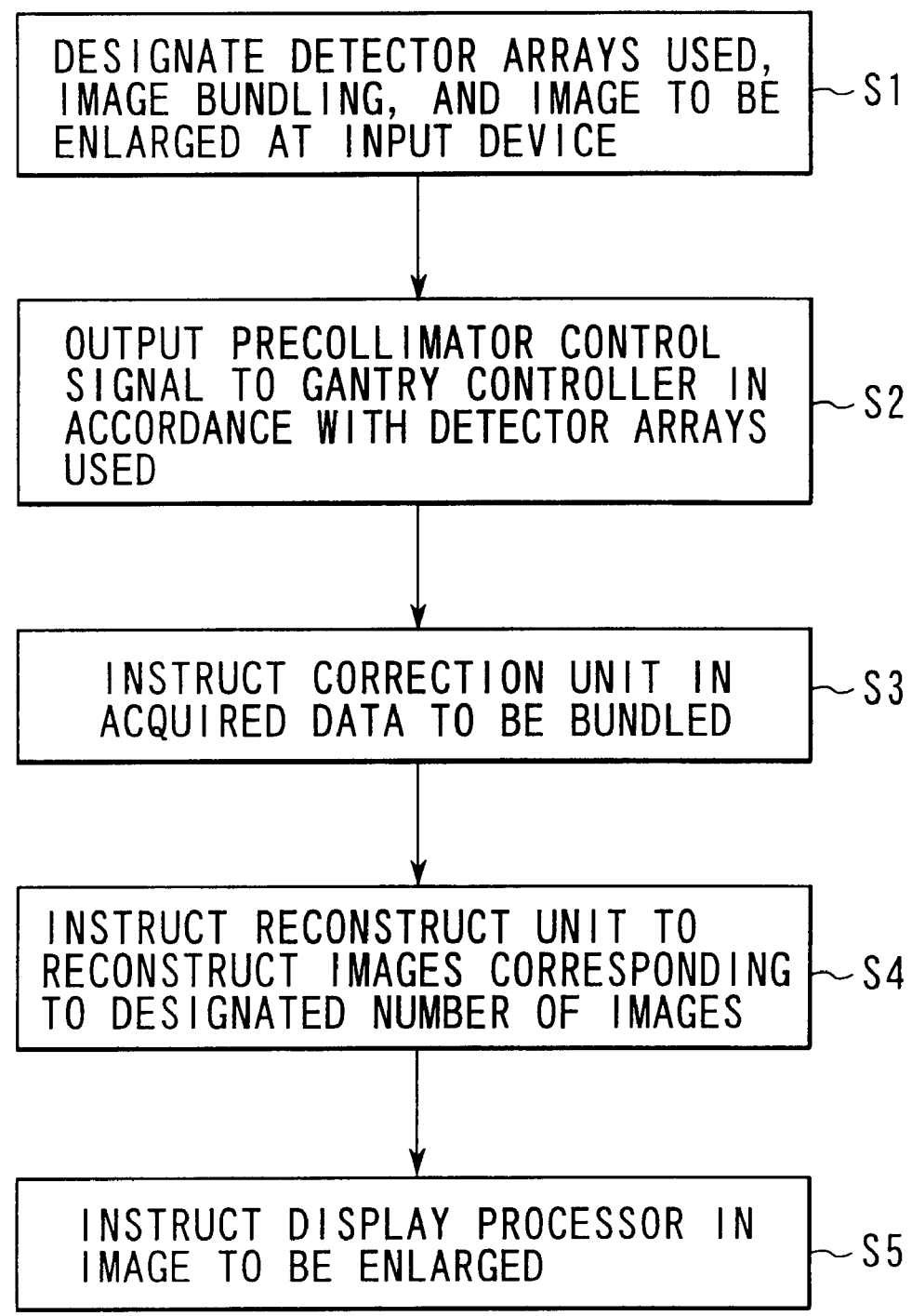
FIG. 44 is a flow chart showing the operation of a main controller according to the sixth embodiment.

FIG. 44 is a flow chart showing the operation of the main controller 30. This flow chart includes decision processes and the like implemented by the main controller 30 upon receiving the designation information from the input device 6.

In step S1, the operator designates the detector arrays used, image bundling, and an image to be enlarged using the input device 6. In step S2, a precollimator control signal is output to the gantry controller 33 in accordance with the detector arrays used. In step S3, the main controller instructs the correction unit 34 in acquired data to be bundled. Subsequently, in step S4 the main controller instructs the reconstruction unit 36 to reconstruct images corresponding to the number of designated images. Then, the main controller instructs the display processor 37 in an image to be enlarged.

[Display on Display]

FIG. 45 is a view showing an image display example by the multi-slice CT fluoroscopy system of this embodiment. FIG. 45A shows a case wherein image 1 is designated by the operator at the input device 6, and is displayed in an enlarged scale compared to images 2 and 3, FIG. 45B shows a case wherein image 2 is designated by the operator at the input device 6, and is displayed in an enlarged scale compared to images 1 and 3, and FIG. 45C shows a case wherein image 3 is designated by the operator at the input device 6, and is displayed in an enlarged scale compared to images 1 and 2.

According to the sixth embodiment described above, since an image designated by the operator is displayed in an enlarged scale compared to other images, a problem of small display size of individual images, which are not easy to observe, upon merely displaying reconstructed images parallel to each other, can be avoided.

Since the image of interest can be displayed in an enlarged scale and other images can also be observed, the present invention is particularly effective for centesis and biopsy procedures. That is, detailed observation can be easily made in the vicinity of a target portion, and the operator is free from any recognition errors of arrival of the centesis needle to the target portion. In biopsies, the target portion can be accurately recognized, and target tissue can be extracted. As described above, according to the present invention, diagnosis performance and operability in multi-slice CT fluoroscopy can be improved.

Modifications of the sixth embodiment will be described below.

[Image Layout Method]

Figure 45A:
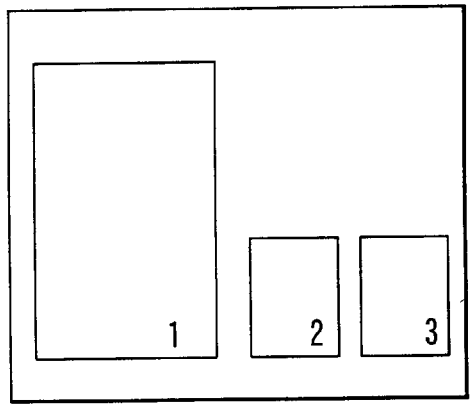
FIG. 45A is a view showing an example of image display by a multi-slice CT fluoroscopy system of the sixth embodiment.
Figure 45D:
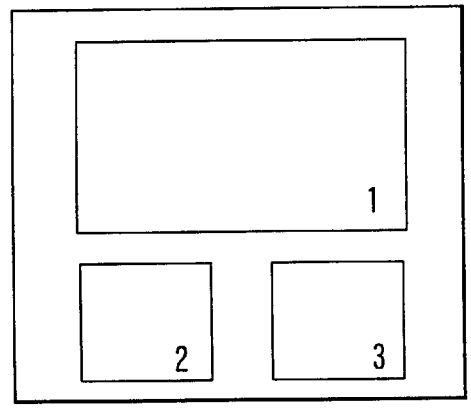
FIG. 45D is a view showing still another example of image display by the multi-slice CT fluoroscopy system of the sixth embodiment.
Figure 45B:
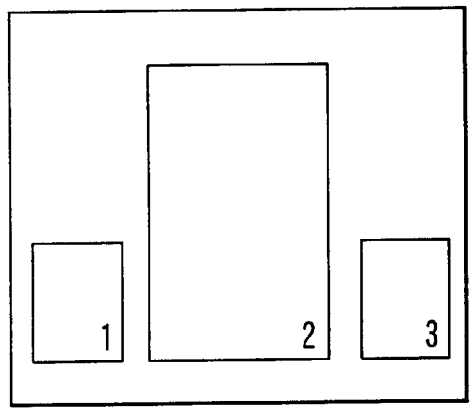
FIG. 45B is a view showing another example of image display by the multi-slice CT fluoroscopy system of the sixth embodiment.
Figure 45E:
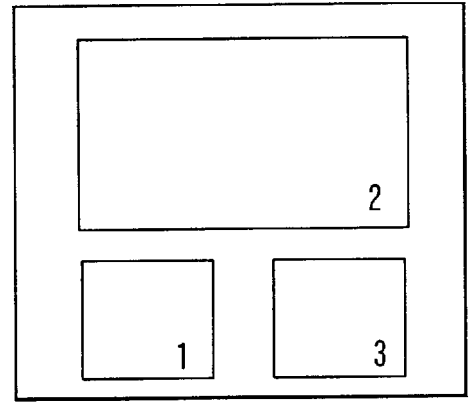
FIG. 45E is a view showing still another example of image display by the multi-slice CT fluoroscopy system of the sixth embodiment.
Figure 45C:
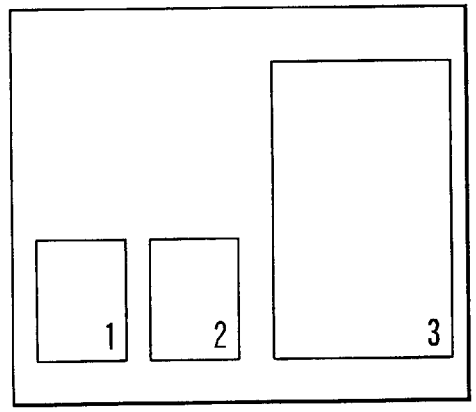
FIG. 45C is a view showing still another example of image display by the multi-slice CT fluoroscopy system of the sixth embodiment.
Figure 45F:
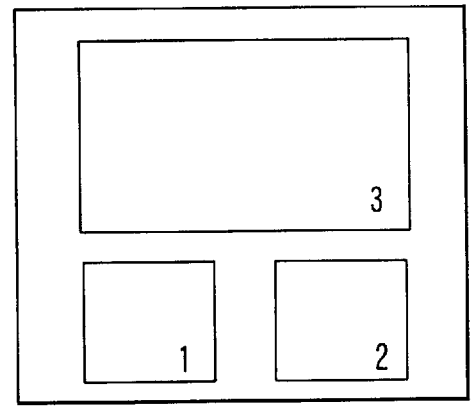
FIG. 45F is a view showing still another example of image display by the multi-slice CT fluoroscopy system of the sixth embodiment.

The image layout method is not limited to those shown in FIGS. 45A, 45B, and 45C. For example, as shown in FIGS. 45D, 45E, and 45F, an enlarged image may be displayed on the upper half at nearly the center of the screen, and other images may be displayed in a line on the lower half of the screen along the slice direction.

[Automatic Detection of Insertion]

In the sixth embodiment, the operator designates an image to be displayed in an enlarged scale using the input device. Alternatively, the following arrangement that automatically selects an enlarged image may be used.

An image to be displayed in an enlarged scale is often an image that shows the distal end of an insertion (centesis needle in this case) into the patient. Thus, an image including the distal end of the centesis needle may be specified by a predetermined image process, and that image may be automatically displayed in an enlarged scale. Since an image process that pertains to extraction of an insertion on an image is known to those who are skilled in the art (threshold value method, edge extraction method, and the like), a detailed description thereof will be omitted.

[Combination with First and Fifth Embodiments]

Figure 46A:
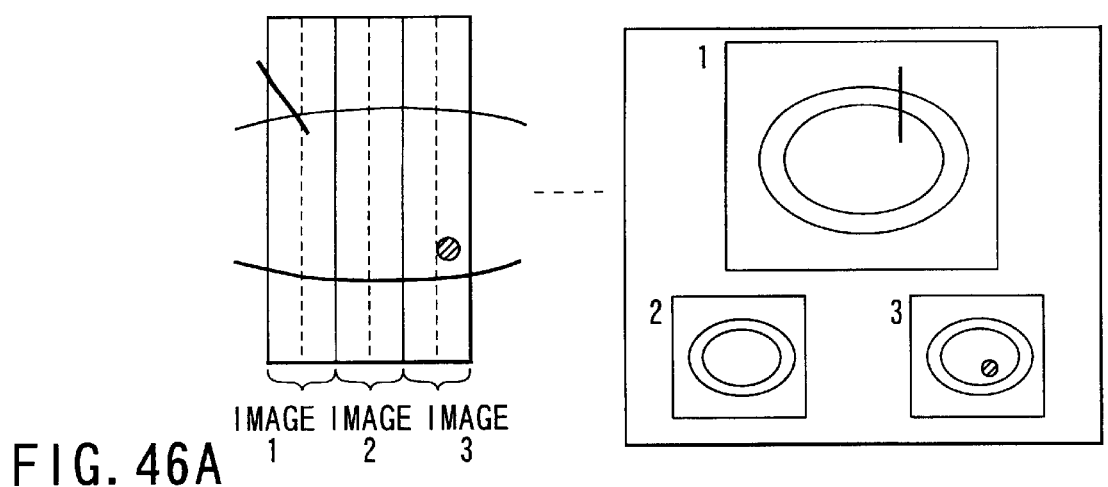
FIG. 46A is a view showing the first state upon switching an image to be displayed in an enlarged scale.
Figure 46B:
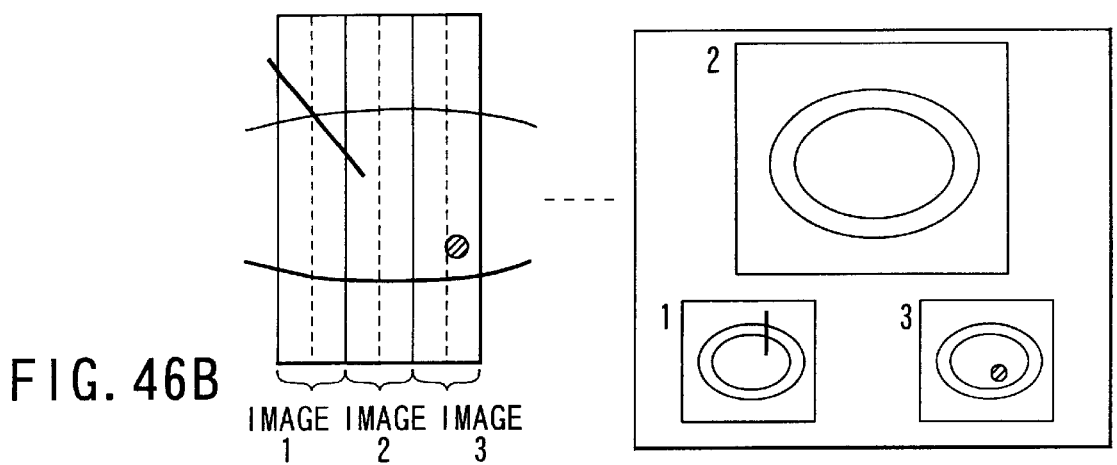
FIG. 46B is a view showing the second state upon switching an image to be displayed in an enlarged scale.

The sixth embodiment can be practiced in combination with the first or fifth embodiment described above. For example, the image of interest may be designated and displayed in an enlarged scale, and other images may undergo the aforementioned differential or threshold process and be displayed in the reduced scale. For example, in FIG. 46B, image 2 may be selected as the image of interest and be displayed in an enlarged scale, and image 1 or 3 may undergo the differential or threshold process and be displayed in a reduced scale, as shown in that figure.

When image 2 displays the target and the centesis needle which is being inserted toward the target, the operator can easily recognize that the centesis needle is accurately inserted toward the target. For this reason, any danger (e.g., insertion of the centesis needle into a wrong organ or the like) can be prevented. Even if such danger is likely to take place, the insertion direction of the centesis needle can be quickly corrected by confirming images 1 and 3, thus shortening the time required for the centesis procedures. Also, arrival of the centesis needle to the target can be easily confirmed on the basis of image 2 which is displayed in the enlarged scale.

Various modifications associated with the first to sixth embodiments described above will be described below.

[Number of Images to be Displayed]

The number of images to be displayed and their slice thicknesses can be arbitrarily set. For example, the present invention can be applied to a case wherein a fluoroscopy mode of a total of five images is set by forming a single image by bundling data from the two central arrays (detector arrays 3 and 4) in addition to four images formed based on data from two end arrays each (detector arrays 1 and 2, and 5 and 6). FIG. 47 shows an example in this case.

Also, for example, the present invention can also be applied to a case wherein a fluoroscopy mode of a total of two images is set by bundling data from three end arrays each (detector examples 1 to 3, and 4 to 6) to form two images. FIG. 48 shows an example in this case.

[Display Method]

In the above embodiments, all images are displayed on a single display. However, the present invention is not limited to such specific image display method. For example, a plurality of images may be respectively displayed on independent displays. In this manner, the individual images can be displayed in an enlarged scale.

Or a projector type large-scale display may be used. In such case, images can be displayed in an enlarged scale and can be observed more easily.

Furthermore, images may be displayed on a head-mounted display. Since images are displayed within the range of the field of view independently of the direction in which the operator faces, the operator need not look back to observe the display during, e.g., the centesis procedures, thus improving operability.

[Type of CT]

In the above embodiments, third-generation CT (the X-ray source and detector synchronously move around the patient) has been exemplified, but the present invention is not limited to such specific CT. The present invention can also be applied to fourth-generation CT (the detector is laid out in a cylindrical pattern, and the X-ray generation source rotates), and to fifth-generation CT (an electron beam impinges against a fixed target laid out in a ring or cylindrical pattern to generate X-rays, which are received by a fixed detector).

[Type of Detector (50 Arrays, Surface Detector)]

In the above embodiments, CT having six detector arrays has been exemplified. However, the number of detector arrays is not limited to six. For example, the present invention can be applied to CT having a multi-slice CT having 50 arrays, and can also be applied to that using a surface detector represented by an image intensifier.

[Reconstruction Condition]

Figure 46C:
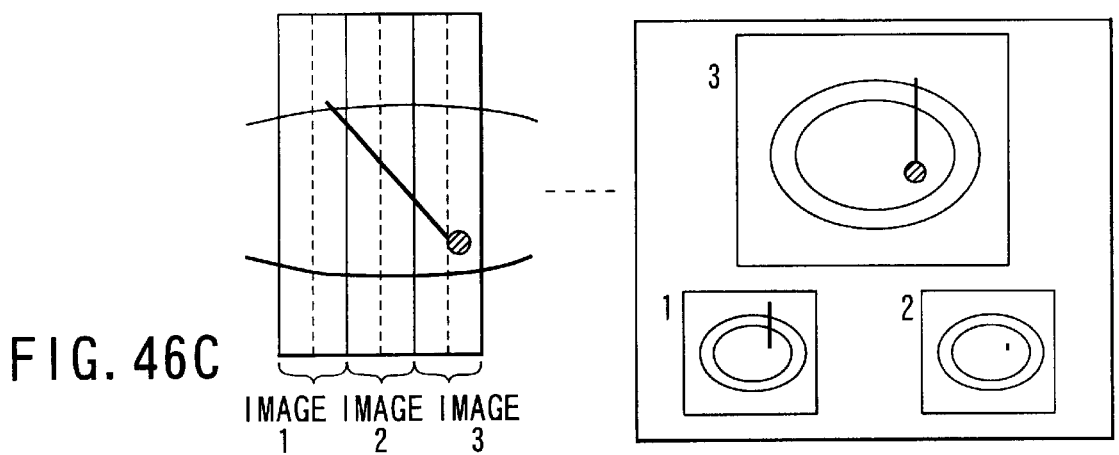
FIG. 46C is a view showing the third state upon switching an image to be displayed in an enlarged scale.

The reconstruction conditions for only some images may be set to be superior to or different from those for other images. For example, like the image of interest shown in FIG. 45 or 46, different reconstruction conditions may be set among images by setting a 512×512 reconstruction matrix for only the image to be displayed in the enlarged scale, and a 256×256 reconstruction matrix for other images. Alternatively, longer image updating intervals other than that of the image of interest may be set to positively lower the temporal resolution. As a result, the reconstruction conditions of images other than the designated image are relaxed, and computation power of the reconstruction unit can be reduced. Hence, cost of the reconstruction device can be reduced.

[Reconstruction Method]

The present invention does not depend on any specific image reconstruction method. For example, a reconstruction method that makes normal filter back-projection regardless of the angle of a beam (cone angle) in the rotation axis direction may be used, or a reconstruction method that reconstructs by back-projecting acquired data in accordance with their acquisition route in accordance with the angle of the beam in the rotation axis direction (proposed by Feldkamp et al.) may be used. Upon executing this Feldkamp reconstruction, acquired data of the respective arrays are not bundled by the aforementioned correction unit, but an image with a slice thickness designated upon reconstruction is reconstructed. According to this reconstruction method, image quality of reconstructed images using a larger number of detector arrays can be improved.

[Location of Bundling]

In the above embodiments, a unit for bundling data is the correction unit. However, the unit for bundling data is not limited to the correction unit. For example, the data acquisition system (DAS) 24 may bundle data, the reconstruction unit 36 may bundle data before reconstructing an image, or images may be bundled after the reconstruction unit 36 reconstructs individual images. Even with these modifications, the same effect can be obtained by the apparatus as a whole.

As described above, according to the fourth to sixth embodiments of the present invention, a surgical procedure can be done while accurately recognizing the position of an insertion such as a centesis needle in the centesis procedure on the basis of differential display or threshold display of a reconstructed image. In this manner, any danger (e.g., a centesis needle pierces a wrong organ of the patient) can be easily avoided, and high-precision centesis procedures can be quickly done. Hence, the dose on the patient can be minimized.

Since an image designated by the operator is displayed in an enlarged scale compared to other images, a problem of small display size of individual images, which are not easy to observe, upon merely displaying reconstructed images parallel to each other, can be avoided. Since the image of interest can be displayed in an enlarged scale and other images can also be observed, the present invention is particularly effective for centesis and biopsy procedures. That is, detailed observation can be easily made in the vicinity of a target portion, and the operator is free from any recognition errors of arrival of the centesis needle to the target portion. In biopsies, the target portion can be accurately recognized, and target tissue can be extracted. As described above, according to the present invention, diagnosis performance and operability in multi-slice CT fluoroscopy can be improved.

(Seventh Embodiment)

The seventh embodiment of the present invention will be described below.

The plurality of embodiments described above relate to an apparatus for multi-slice CT fluoroscopy. That is, image acquisition with X-ray radiation and display of acquired images (reconstructed images) are done nearly in real time.

Meanwhile, this embodiment applies the principle of the present invention to image re-display executed after image acquisition.

In this embodiment, a set of a plurality of tomographic images having different positions in the slice direction are acquired, and a plurality of sets of images of different timings are obtained by repeating acquisition and are stored. The plurality of sets of stored images are read out as needed and are re-displayed.

Figure 49:
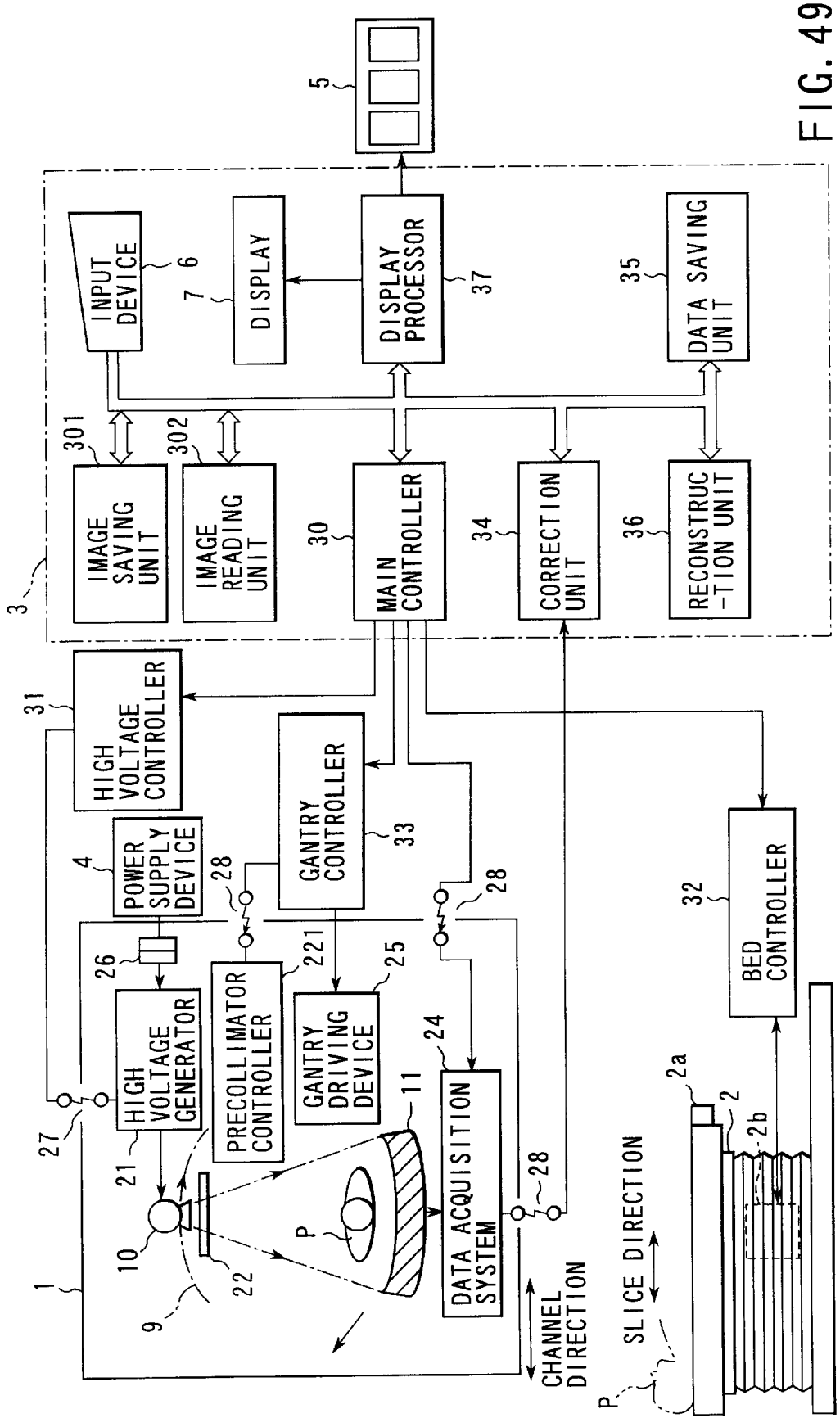
FIG. 49 is a block diagram showing a schematic arrangement of a multi-slice CT system according to the seventh embodiment of the present invention.
Figure 50:
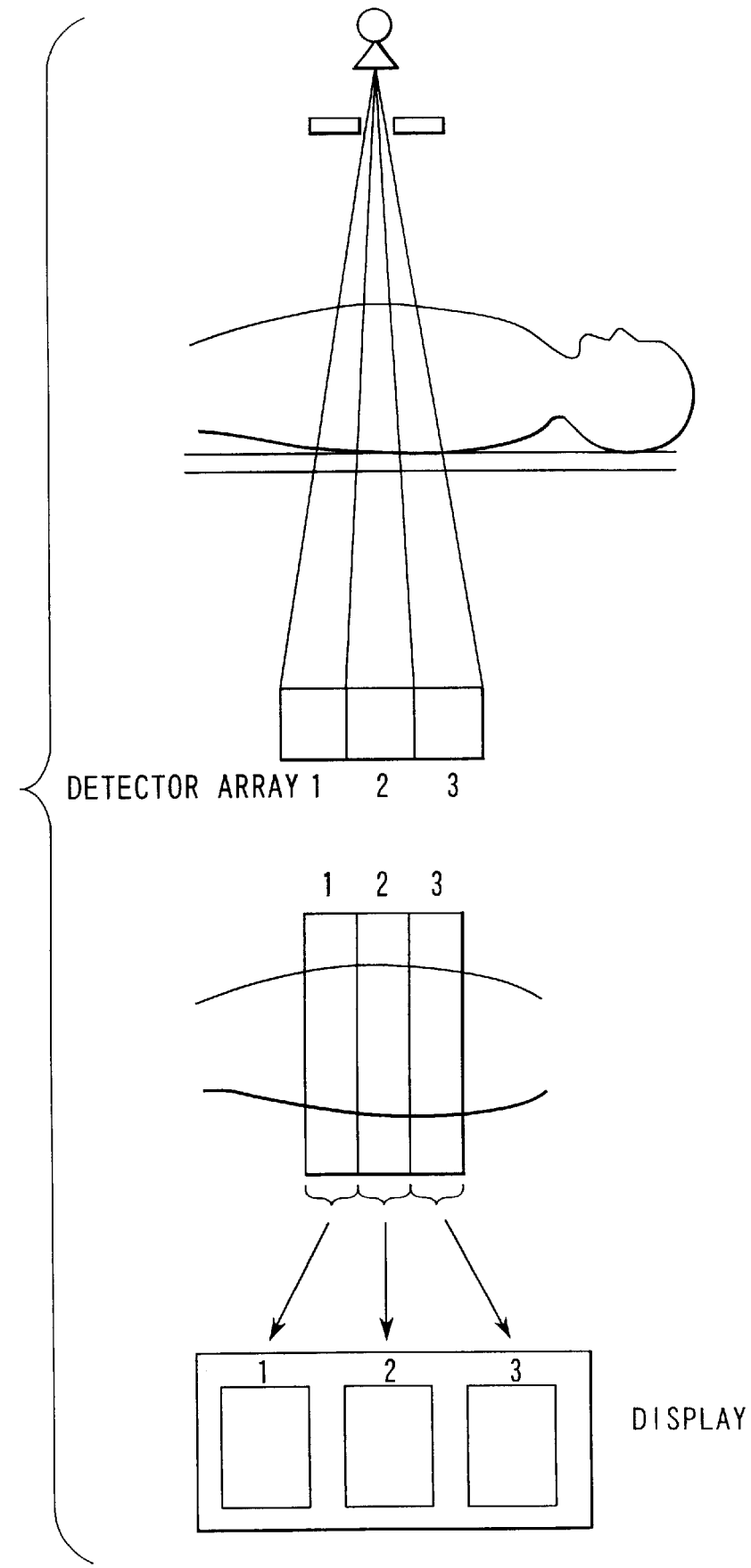
FIG. 50 is a view showing multi-slice CT fluoroscopy according to the prior art of the present invention.
Figure 51:
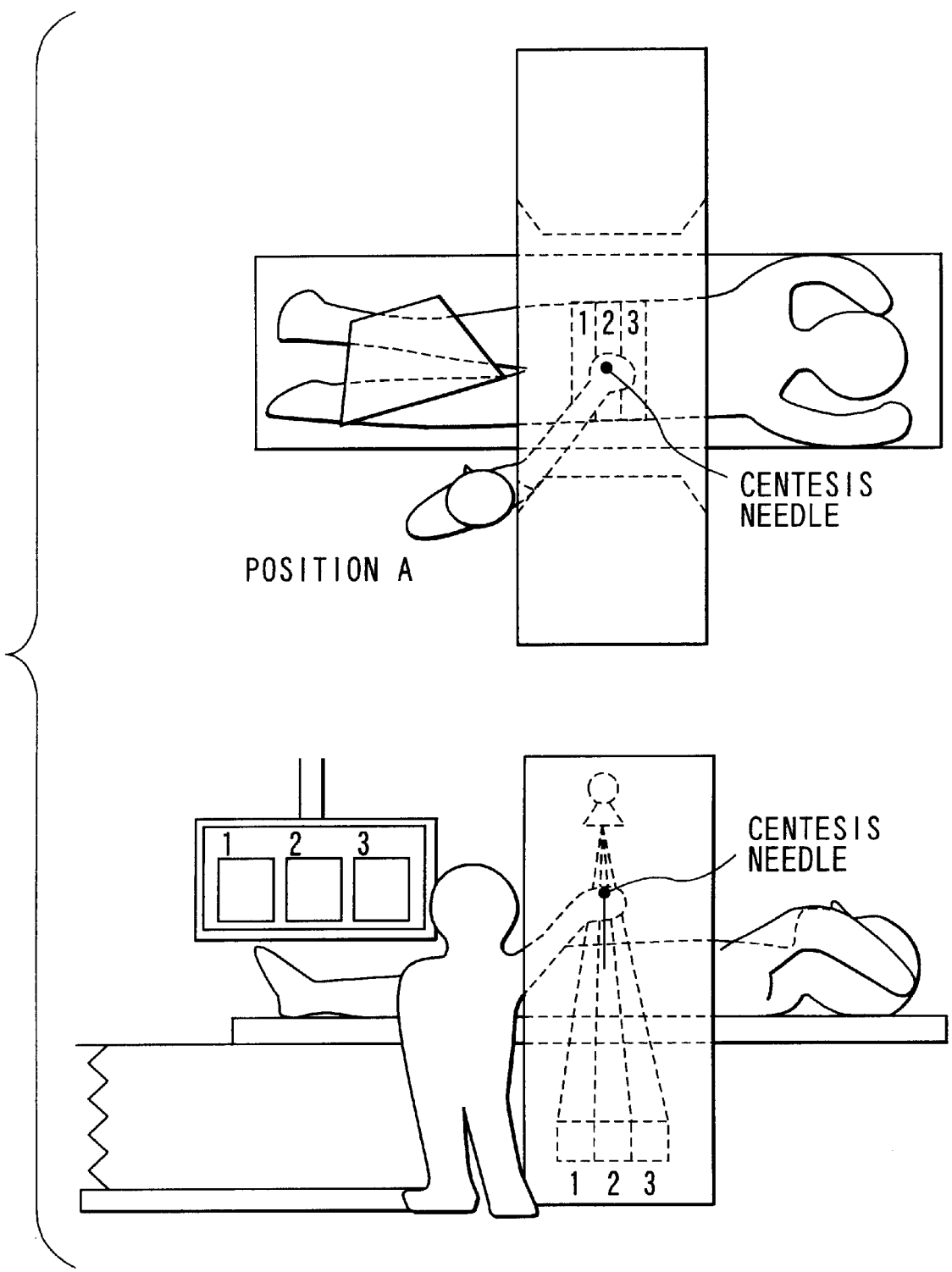
FIG. 51 is a view showing a standing position of the observer in multi-slice CT fluoroscopy according to the prior art of the present invention.
Figure 52:
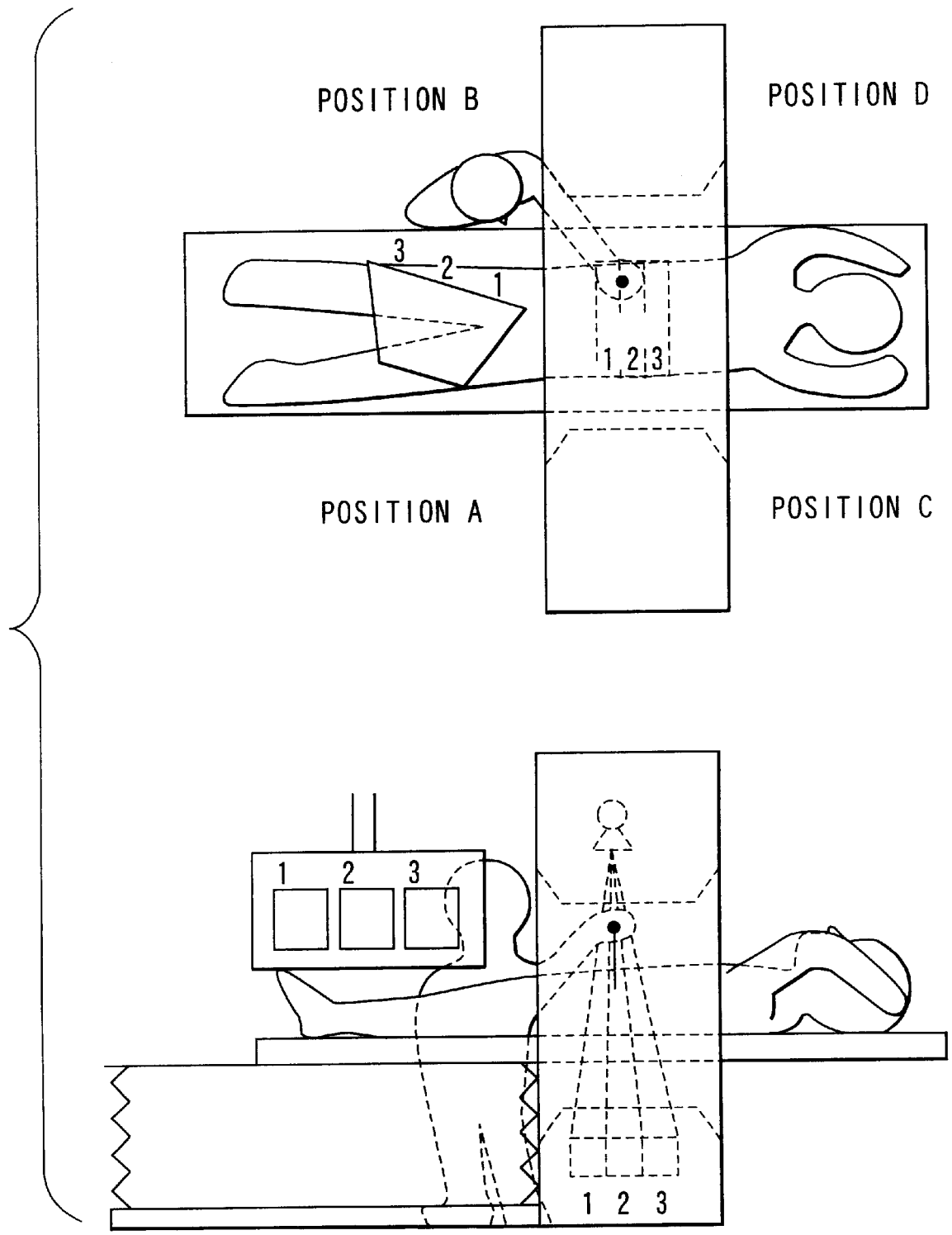
FIG. 52 is a view showing another standing position of the observer in multi-slice CT fluoroscopy according to the prior art of the present invention.
Figure 53:
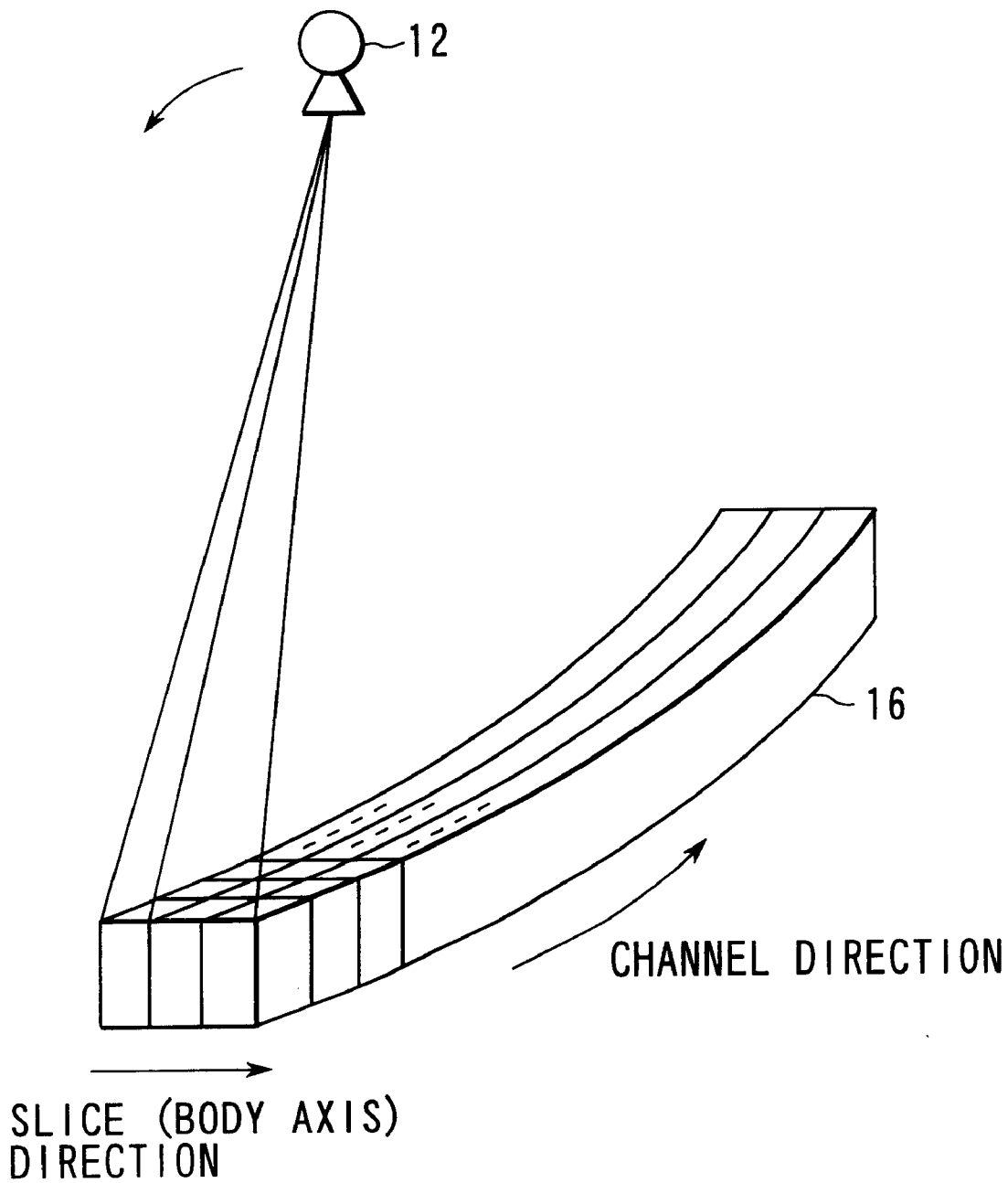
FIG. 53 is a perspective view showing the arrangement of a multi-slice detector according to the prior art of the present invention.

FIG. 49 is a block diagram showing a schematic arrangement of a multi-slice CT system according to the seventh embodiment. This system is different from those in the first to sixth embodiment in that an image saving unit 301 and image reading unit 302 are added.

The correction unit 34 performs various correction processes of acquired digital data sent from the DAS 24 in accordance with a process command from the main controller 30. The acquired data that has undergone the correction processes is temporarily stored and saved in the data saving unit 35 in response to a write command from the main controller 30. The saved data is read out from the data saving unit 35 in accordance with a read command from the main controller 30 at a desired timing, and is transferred to the reconstruction unit 36. The reconstruction unit 36 executes a reconstruction process in units of slices on the basis of, e.g., a convolution back-projection method when it receives acquired data to be reconstructed under the control of the main controller 30, thus generating tomographic images.

Tomographic image data is saved in the image saving unit 301 under the control of the main controller 30. With the aforementioned operations, a plurality of sets of tomographic images at different timings are obtained, and can be used permanently. Note that raw data may be saved in the image saving unit 301 in place of reconstructed tomographic image data.

When the operator inputs a predetermined re-display command at the input device 6, the image reading unit 302 reads out a plurality of sets of tomographic image data from the image saving unit 301, and supply them to the display processor 37. After that, the display order control according to the standing position of the observer, enlarged display of the image of interest, or the like is executed, as has been described in the above embodiments.

Needless to say, since this embodiment relates to re-display, but does not display in real time, no examinations such as biopsies or the like are done during re-display.

For example, this embodiment is effective for image re-display after contrast examination. More specifically, this embodiment is effective for a case wherein the progress of osmosis of a contrast medium injected into the patient is observed again after contrast examination. Image data saved in the image saving unit 301 can be read out anytime by the image reading unit, and contribute to implementation of medical diagnosis over a broad range.

Also, in this embodiment, the aforementioned effects can be obtained by applying the principle of the present invention to a non-real time CT system which does not comprise any real-time reconstruction unit (corresponding to the reconstruction unit 36 in the first to sixth embodiments described above).

To restate, according to the present invention, an X-ray computed tomography apparatus which displays a plurality of tomographic images by appropriately setting the display order or obverse/reverse side of images can be provided.

Also, an X-ray computer tomography apparatus which allows an appropriate and quick surgical procedure such as a centesis or the like under multi-slice CT fluoroscopy can be provided.

Furthermore, an X-ray computer tomography apparatus which can reduce the dose on a patient upon multi-slice CT fluoroscopy can be provided.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An X-ray computed tomography apparatus comprising:
an X-ray generation unit for generating X-rays;
a detection unit which is constructed by a plurality of detection element arrays each having a plurality of detection channels in a slice direction, and in which the respective detection channels detect X-rays emitted by said X-ray generation unit;
generation means for generating a tomographic image of an object to be examined by bundling data from the detection element arrays; and
changing means for changing at least one of an incident width of an X-ray beam that hits the detection element arrays and the bundle of data during a scan period.

2. An X-ray computed tomography apparatus comprising:
a detection unit for detecting a transmitted X-ray beam which is emitted by an X-ray generation unit and transmitted through an object to be examined;
a reconstruction unit for reconstructing a tomographic image of the object to be examined on the basis of detection data obtained by said detection unit;
a display unit for displaying a plurality of tomographic images reconstructed by said reconstruction unit in a line; and
changing means for changing the way the plurality of tomographic images line up in said display unit in accordance with a standing position of an observer with respect to the object to be examined.

3. An apparatus according to claim 2, wherein said reconstruction unit reconstructs at least one tomographic image within a time shorter than a time required per scan.

4. An apparatus according to claim 2, wherein said detection unit includes a two-dimensional detection unit constructed by a plurality of detection element arrays each having a plurality of detection channels in a slice direction.

5. An apparatus according to claim 2, 3, or 4, wherein said changing means changes display positions of a plurality of tomographic images displayed on said display unit.

6. An apparatus according to claim 5, wherein when said display unit displays a plurality of tomographic images to be parallel to each other, said changing means reverses an order of the images horizontally.

7. An apparatus according to claim 4, wherein at least one of the plurality of tomographic images is formed based on bundling data from at least a plurality of detection element arrays.

8. An apparatus according to claim 2, 3, or 4, wherein said changing means includes a conversion unit for converting an obverse/reverse side of a tomographic image reconstructed by said reconstruction unit in accordance with a position of the observer.

9. An apparatus according to claim 2, 3, or 4, wherein said changing means changes an order of a plurality of tomographic images reconstructed by said reconstruction unit to match an order of slices of the object to be examined viewed from the observer.

10. An apparatus according to claim 2, 3, or 4, further comprising a designation unit for designating a position of the observer, and wherein said changing means changes an order of a plurality of tomographic images displayed on said display unit in accordance with the position of the observer designated by said designation unit.

11. An apparatus according to claim 2, 3, or 4, further comprising a position detection unit for detecting a position of the observer, and wherein said changing means changes an order of a plurality of tomographic images displayed on said display unit in accordance with the position of the observer detected by said position detection unit.

12. An apparatus according to claim 10, wherein said designation unit designates the position of the observer with respect to at least the object to be examined and the X-ray generation unit.

13. An apparatus according to claim 11, wherein said position detection unit detects at least a position of said display unit with respect to a gantry that mounts the X-ray generation unit, and a direction of a display screen of said display unit.

14. An apparatus according to claim 2, 3, or 4, wherein said changing means changes a display size of a specific one of a plurality of tomographic images displayed on said display unit to be different from other tomographic images.

15. An X-ray computed tomography apparatus comprising:
 a detection unit which is constructed by a plurality of detection element arrays each having a plurality of detection channels in a slice direction, and in which the respective detection channels detect X-rays;
 a reconstruction unit for reconstructing first tomographic images corresponding to different times on the basis of detection data detected by first detection element arrays of said detection unit, and for reconstructing second tomographic images which correspond in time to the first tomographic images on the basis of detection data detected by second detection element arrays, which are different from the first detection element arrays;
 a display unit for displaying the first and second tomographic images side by side; and
 a display control unit for controlling said display unit to display the first tomographic images correspond to different times in a display mode different from that of the second tomographic image.

16. An apparatus according to claim 15, further comprising a selection unit for selecting the first tomographic image from a plurality of tomographic images displayed on said display unit.

17. An apparatus according to claim 15, wherein said display control unit controls said display unit to display the first tomographic image in a scale larger than the second tomographic image.

18. An apparatus according to claim 15, 16, or 17, wherein said display control unit controls said display unit to display the first tomographic image at a higher resolving power or resolution than the second tomographic image.

19. An apparatus according to claim 15, 16, or 17, wherein said display control unit controls said display unit to display the first tomographic image at an upper position than the second tomographic image on a display screen.

20. An apparatus according to claim 15, 16, or 17, further comprising a needle detection unit for detecting a distal end of a needle inserted into the object to be examined, and wherein said display control unit sets a display mode of a first tomographic image from which the distal end of the needle is detected by said needle detection unit to be different from a display mode of a second tomographic image from which no distal end of the needle is detected by said needle detection unit.

21. An X-ray computed tomography apparatus comprising:
 an X-ray generating unit;
 a detection unit which is constructed by a plurality of detection element arrays each having a plurality of detection channels in a slice direction, and in which the respective detection channels detect X-rays emitted by said X-ray generation unit;
 a reconstruction unit for reconstructing first tomographic images corresponding to different times on the basis of detection data detected by first detection element arrays of said detection unit, and for reconstructing second tomographic images which correspond in time to the first tomographic images on the basis of detection data detected by second detection element arrays, which are different from the first detection element arrays;
 slice thickness changing means for setting a slice thickness of the first tomographic images to be larger than a slice thickness of the second tomographic images; and
 a display unit for displaying the first and second tomographic images, the slice thicknesses of which have been changed by said slice thickness control means, said first and second tomographic images being displayed according to time.

22. An apparatus according to claim 21, wherein said reconstruction unit reconstructs the first and second tomographic image within a time shorter than a time required per scan.

23. An apparatus according to claim 21, further comprising a collimator which is inserted between said X-ray generation unit and the object to be examined, and has a variable aperture for defining a beam width of X-rays emitted by said X-ray generation means in a slice direction, and wherein said slice thickness changing means controls the variable aperture to set the slice thickness of the image of interest to be larger than the slice thickness of the image of non-interest.

24. An apparatus according to claim 21, 22, or 23, wherein said slice thickness changing means controls said reconstruction unit to reconstruct the image of interest by bundling data from a plurality of detection element arrays, and to reconstruct the image of non-interest on the basis of data from a single detection element array.

25. An apparatus according to claim 21, 22, or 23, wherein said slice thickness changing means controls said reconstruction unit to reconstruct the image of interest by bundling data from the detection element arrays based on the first number of data to be bundled, and to reconstruct the image of non-interest on the basis of data by bundling data from the detection element arrays based on the number of data to be bundled smaller than the first number of data to be bundled.

26. An apparatus according to claim 21, 22, or 23, wherein said reconstruction unit controls said reconstruction unit to reconstruct the image of interest on the basis of data from a predetermined detection element array, and to reconstruct the image of non-interest on the basis of data from one of at least a neighboring detection element array of the predetermined detection element array and a nearby detection element array.

27. An apparatus according to claim 26, wherein said slice thickness changing means controls an aperture width of the variable aperture of said collimator to decrease a width of an X-ray beam in the slice direction, which enters the neighboring detection element array of the predetermined detection element array by a predetermined amount along a direction of the predetermined detection element array.

28. An apparatus according to claim 21, 22, or 23, further comprising:
   a designation unit for designating a detection element array for obtaining the image of interest; and
   a determination unit for determining the detection element array for obtaining the image of interest on the basis of designation contents of said designation unit.

29. An apparatus according to claim 28, wherein said slice thickness changing means controls an aperture width of the variable aperture of said collimator in accordance with the designation contents of said designation unit and determination contents by said determination unit.

30. An apparatus according to claim 21, 22, or 23, further comprising a changing unit for changing a position of the detection element array for obtaining the image of interest along a slice direction.

31. An X-ray computed tomography apparatus comprising:
   a detection unit for detecting a transmitted X-ray beam which is emitted by an X-ray generation unit and transmitted through an object to be examined;
   a reconstruction unit for reconstructing first tomographic images corresponding to different times on the basis of detection data detected by first detection element arrays of said detection unit, and for reconstructing second tomographic images which correspond in time to the first tomographic images on the basis of detection data detected by second detection element arrays, which are different from the first detection element arrays;
   a display unit for displaying the first and second tomographic images side by side; and
   a display control unit for displaying the first tomographic images having a first slice thickness at a substantially center of said display unit, and displaying the second tomographic images having a second slice thickness smaller than the first slice thickness at an end portion of the first tomographic images according to time.

32. An X-ray computed tomography apparatus comprising:
   an X-ray generation unit for generating X-rays;
   a detection unit which is constructed by a plurality of detection element arrays each having a plurality of detection channels in a slice direction, and in which the respective detection channels detect X-rays emitted by said X-ray generation unit;
   a reconstruction unit for reconstructing first tomographic images corresponding to different times on the basis of detection data detected by first detection element arrays of said detection unit, and for reconstructing second tomographic images which correspond in time to the first tomographic images on the basis of detection data detected by second detection element arrays, which are different from the first detection element arrays; and
   an image processing unit for generating a differential images corresponding to different times by differentially processing a specific image and at least the first tomographic images.

33. An apparatus according to claim 32, wherein said reconstruction unit reconstructs at least one tomographic image within a time shorter than a time required per scan.

34. An apparatus according to claim 32, further comprising a display unit for displaying the tomographic image which does not undergo the differential process of said image processing unit, and the differential image side by side.

35. An apparatus according to claim 32, further comprising a switching unit for switching an image to be subjected to the differential process by said image processing unit among a plurality of tomographic images reconstructed by said reconstruction means.

36. An apparatus according to claim 32, 33, 34, or 35 wherein the specific image is an image at an identical slice position reconstructed by said reconstruction unit.

37. An apparatus according to claim 32, 33, 34, or 35, wherein the specific image is a designated tomographic image.

38. An apparatus according to claim 32, 33, 34, or 35, wherein said image processing unit executes the differential process using a tomographic image reconstructed based on detection data from an end detection element array or detection element array near the end detection element array of the plurality of detection element arrays that receive the X-ray beam.

39. An apparatus according to claim 32, 33, 34, or 35, further comprising:
   a comparison unit for comparing a pixel value of the differential image with a predetermined threshold value; and
   an alert unit for producing an alert on the basis of a comparison result of said comparison unit.

40. An apparatus according to claim 39, wherein said alert unit produces different alerts in units of tomographic images to be subjected to the differential process.

41. An apparatus according to claim 39 or 35, wherein said display unit displays at least one of the tomographic image which does not undergo the differential process, and the differential image in color to be able to distinguish the two images from each other, and displays the two images superposed on each other.

42. An X-ray computed tomography apparatus comprising:
   an X-ray generation unit for generating X-rays;
   a detection unit which is constructed by a plurality of detection element arrays each having a plurality of detection channels in a slice direction, and in which the respective detection channels detect X-rays emitted by said X-ray generation unit;
   a reconstruction unit for reconstructing first tomographic images corresponding to different times on the basis of detection data detected by first detection element arrays of said detection unit, and for reconstructing second tomographic images which correspond in time to the first tomographic images on the basis of detection data detected by second detection element arrays, which are different from the first detection element arrays; and
   a threshold process unit for comparing a pixel value of at least the first tomographic images with a predetermined threshold value, and generating a threshold image consisting of pixel values that have exceeded the threshold value according to time.

43. An apparatus according to claim 42, wherein said reconstruction unit reconstructs at least one tomographic image within a time shorter than a time required per scan.

44. An apparatus according to claim 42 or 43, further comprising a display unit for displaying the tomographic image which does not undergo the threshold process of said threshold process unit, and the threshold image side by side.

45. An X-ray computed tomography apparatus comprising:

an X-ray generation unit for generating X-rays;

a detection unit which is constructed by a plurality of detection element arrays each having a plurality of detection channels in a slice direction, and in which the respective detection channels detect X-rays emitted by said X-ray generation unit;

a reconstruction unit for reconstructing first tomographic images corresponding to different times on the basis of detection data detected by first detection element arrays of said detection unit, and for reconstructing second tomographic images which correspond in time to the first tomographic images on the basis of detection data detected by second detection element arrays, which are different from the first detection element arrays; and a threshold process unit for comparing a pixel value of at least the first tomographic images with a predetermined threshold value, and generating a threshold image consisting of pixel values that have exceeded the threshold value according to time, wherein the threshold value is a pixel value which distinguishes the object to be examined and an insertion into the object to be examined.

46. An apparatus according to claim 45, wherein said display unit displays at least one of the tomographic image which does not undergo the threshold process, and the threshold image in color to be able to distinguish the two images from each other, and displays the two images superposed on each other.

47. An apparatus according to claim 42 or 45, wherein said threshold process unit executes the threshold process using a tomographic image reconstructed based on detection data from an end detection element array or detection element array near the end detection element array of the plurality of detection element arrays that receive the X-ray beam.

48. An apparatus according to claim 42 or 45, further comprising an alert unit for producing an alert when the pixel value of the tomographic image has exceeded the threshold value.

49. An apparatus according to claim 48, wherein said alert unit produces different alerts in units of tomographic images to be subjected to the threshold process.

* * * * *